United States Patent
Powell et al.

(10) Patent No.: US 11,377,481 B2
(45) Date of Patent: Jul. 5, 2022

(54) SPYCATCHER AND SPYTAG: UNIVERSAL IMMUNE RECEPTORS FOR T CELLS

(71) Applicant: THE TRUSTEES OF THE UNIVERSITY OF PENNSYLVANIA, Philadelphia, PA (US)

(72) Inventors: Daniel Powell, Bala Cynwyd, PA (US); Andrew Tsourkas, Bryn Mawr, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 748 days.

(21) Appl. No.: 16/064,875

(22) PCT Filed: Dec. 21, 2016

(86) PCT No.: PCT/US2016/068055
§ 371 (c)(1),
(2) Date: Jun. 21, 2018

(87) PCT Pub. No.: WO2017/112784
PCT Pub. Date: Jun. 29, 2017

(65) Prior Publication Data
US 2019/0389925 A1   Dec. 26, 2019

Related U.S. Application Data

(60) Provisional application No. 62/271,071, filed on Dec. 22, 2015.

(51) Int. Cl.
*C07K 14/725* (2006.01)
*C07K 14/705* (2006.01)
*A61K 35/17* (2015.01)

(52) U.S. Cl.
CPC .......... *C07K 14/7051* (2013.01); *A61K 35/17* (2013.01); *C07K 14/70521* (2013.01); *C07K 2319/02* (2013.01); *C07K 2319/03* (2013.01); *C07K 2319/20* (2013.01); *C07K 2319/60* (2013.01)

(58) Field of Classification Search
CPC ................. A61K 35/17; C07K 14/7051; C07K 14/70521; C07K 2319/02; C07K 2319/03; C07K 2319/20
See application file for complete search history.

(56) References Cited

U.S. PATENT DOCUMENTS

2013/0287752 A1* 10/2013 Davila ............... A61K 39/0011
424/93.71
2015/0125429 A1   5/2015 Perlingeiro et al.
2015/0306212 A1* 10/2015 Kahvejian ............ A61K 9/5068
424/134.1

OTHER PUBLICATIONS

Hinrichs et al., "IL-2 and IL-21 confer opposing differentiation programs to CD8+ T cells for adoptive immunotherapy", 2008, Blood 111(11), p. 5326-5333.*
Song et al., "In Vivo Persistence, Tumor Localization, and Antitumor Activity of CAR-Engineered T Cells Is Enhanced by Costimulatory Signaling through CD137 (4-1BB)", 2011, American Association for Cancer Research 73(13), p. 4617-4627.*
Urbanska et al., OncoImmunology 2012, 1(5): 777-779 (Year: 2012).*
Urbanska et al. Cancer Res. 2012, 72 (7): 1844-1852 (Year: 2012).*
International Search Report and Written Opinion for PCT International Application No. PCT/US2016/068055 dated May 4, 2018.

* cited by examiner

*Primary Examiner* — James D Schultz
(74) *Attorney, Agent, or Firm* — Saul Ewing Arnstein & Lehr LLP; Kathryn Doyle; Jacque Young

(57) ABSTRACT

The invention provides compositions and methods for adoptive T cell therapy in treating a variety of disorders including cancer, infections, and autoimmune disorders. In one embodiment, the invention provides a universal immune receptor that comprises a protein or peptide tag, such as a SpyCatcher or a SpyTag moiety, bound to an extracellular hinge region, a transmembrane domain, and an intracellular domain for T cell activation.

20 Claims, 29 Drawing Sheets

Specification includes a Sequence Listing.

Lists of SpyTag and Spycatcher constructs

| GFP/Non-GFP | Insert | Constructs |
|---|---|---|
| Non-GFP construct | SpyTag | pELNS(SpeI)-SpyTag-CD28-Zeta |
| Non-GFP construct | SpyTag-GGS | pELNS(SpeI)-SpyTag-GGS-CD28-Zeta |
| Non-GFP construct | SpyCatcher | pELNS(SpeI)-SpyCatcher-CD28-Zeta |
| Non-GFP construct | SpyCatcher-GGS | pELNS(SpeI)-SpyCatcher-GGS-CD28-Zeta |
| GFP Construct | SpyTag | pELNS(Spe1)_GFP_2A_SpyTag_CD28_Zeta |
| GFP Construct | SpyTag-GGS | pELNS(Spe1)_GFP_2A_SpyTag-GGS repeat_CD28_Zeta |
| GFP Construct | SpyCatcher | pELNS(Spe1)_GFP_2A_SpyCatcher_CD28_Zeta |
| GFP Construct | SpyCatcher-GGS | pELNS(Spe1)_GFP_2A_SpyCatcher_CD28_Zeta |

FIG. 2

B) Sequence of pELNS(SpeI)-SpyTag-CD28-Zeta

Nucleotide sequence (SEQ ID NO: 9)
ATGGCCTTACCAGTGACCGCCTTGCTCCTGCCGCTGGCCTTGCTGCTCCACGCCGCCAGGCCGGGAT
CCGCCCACATTGTGATGGTGGACGCCTACAAGCCCACCAAGGCTAGCACCACGACGCCAGCGCCGC
GACCACCAACACCGGCGCCCACCATCGCGTCGCAGCCCCTGTCCCTGCGCCCAGAGGCGTGCCGGC
CAGCGGCGGGGGGCGCAGTGCACACGAGGGGGCTGGACTTCGCCTGTGATTTTTGGGTGCTGGTG
GTGGTTGGTGGAGTCCTGGCTTGCTATAGCTTGCTAGTAACAGTGGCCTTTATTATTTTCTGGGTGA
GGAGTAAGAGGAGCAGGCTCCTGCACAGTGACTACATGAACATGACTCCCCGCCGCCCCGGGCCCA
CCCGCAAGCATTACCAGCCCTATGCCCCACCACGCGACTTCGCAGCCTATCGCTCCATCGATAGAGT
GAAGTTCAGCAGGAGCGCAGACGCCCCCGCGTACCAGCAGGGCCAGAACCAGCTCTATAACGAGCT
CAATCTAGGACGAAGAGAGGAGTACGATGTTTTGGACAAGAGACGTGGCCGGGACCCTGAGATGG
GGGGAAAGCCGAGAAGGAAGAACCCTCAGGAAGGCCTGTACAATGAACTGCAGAAAGATAAGATG
GCGGAGGCCTACAGTGAGATTGGGATGAAAGGCGAGCGCCGGAGGGGCAAGGGGCACGATGGCC
TTTACCAGGGTCTCAGTACAGCCACCAAGGACACCTACGACGCCCTTCACATGCAGGCCCTGCCCCC
TCGCTAA

Amino acid sequence (SEQ ID NO: 10)
MALPVTALLLPLALLLHAARPGSAHIVMVDAYKPTKASTTTPAPRPPTPAPTIASQPLSLRPEACRPAAGG
AVHTRGLDFACDFWVLVVVGGVLACYSLLVTVAFIIFWVRSKRSRLLHSDYMNMTPRRPGPTRKHYQPY
APPRDFAAYRSIDRVKFSRSADAPAYQQGQNQLYNELNLGRREEYDVLDKRRGRDPEMGGKPRRKNPQ
EGLYNELQKDKMAEAYSEIGMKGERRRGKGHDGLYQGLSTATKDTYDALHMQALPPR*

FIG. 3B

B) Sequence of pELNS(SpeI)-SpyTag-GGS-CD28-Zeta

Nucleotide sequence (SEQ ID NO: 11)
ATGGCCTTACCAGTGACCGCCTTGCTCCTGCCGCTGGCCTTGCTGCTCCACGCCGCCAGGCCGGGAT
CCGCCCACATCGTGATGGTGGACGCCTACAAGCCCACCAAGGGCGGCAGCGGCGGCAGCGGCGGC
AGCGGCGGCAGCGGCGGCAGCGGCGGCAGCGGCGGCAGCGCTAGCACCACGACGCCAGCGCCGC
GACCACCAACACCGGCGCCCACCATCGCGTCGCAGCCCCTGTCCCTGCGCCCAGAGGCGTGCCGGC
CAGCGGCGGGGGGCGCAGTGCACACGAGGGGGCTGGACTTCGCCTGTGATTTTTGGGTGCTGGTG
GTGGTTGGTGGAGTCCTGGCTTGCTATAGCTTGCTAGTAACAGTGGCCTTTATTATTTTCTGGGTGA
GGAGTAAGAGGAGCAGGCTCCTGCACAGTGACTACATGAACATGACTCCCCGCCGCCCCGGGCCCA
CCCGCAAGCATTACCAGCCCTATGCCCCACCACGCGACTTCGCAGCCTATCGCTCCATCGATAGAGT
GAAGTTCAGCAGGAGCGCAGACGCCCCCGCGTACCAGCAGGGCCAGAACCAGCTCTATAACGAGCT
CAATCTAGGACGAAGAGAGGAGTACGATGTTTTGGACAAGAGACGTGGCCGGGACCCTGAGATGG
GGGGAAAGCCGAGAAGGAAGAACCCTCAGGAAGGCCTGTACAATGAACTGCAGAAAGATAAGATG
GCGGAGGCCTACAGTGAGATTGGGATGAAAGGCGAGCGCCGGAGGGGCAAGGGGCACGATGGCC
TTTACCAGGGTCTCAGTACAGCCACCAAGGACACCTACGACGCCCTTCACATGCAGGCCCTGCCCCC
TCGCTAA Amino acid sequence (SEQ ID NO: 12)
MALPVTALLLPLALLLHAARPGSAHIVMVDAYKPTKGGSGGSGGSGGSGGSGGSGGSASTTTPAPRPPT
PAPTIASQPLSLRPEACRPAAGGAVHTRGLDFACDFWVLVVVGGVLACYSLLVTVAFIIFWVRSKRSRLLH
SDYMNMTPRRPGPTRKHYQPYAPPRDFAAYRSIDRVKFSRSADAPAYQQGQNQLYNELNLGRREEYDV
LDKRRGRDPEMGGKPRRKNPQEGLYNELQKDKMAEAYSEIGMKGERRRGKGHDGLYQGLSTATKDTY
DALHMQALPPR*

FIG. 4B

B) Sequence of pELNS(SpeI)-SpyCatcher-CD28-Zeta

Nucleotide sequence (SEQ ID NO: 5)
ATGGCCTTACCAGTGACCGCCTTGCTCCTGCCGCTGGCCTTGCTGCTCCACGCCGCCAGGCCGGGAT
CCGGAAGCGGAGATAGCGCCACCCACATCAAGTTCAGCAAGCGGGACGAGGACGGCAAAGAGCTG
GCTGGCGCCACCATGGAACTGCGGGATAGCAGCGGCAAGACCATCAGCACCTGGATCAGCGACGG
CCAGGTCAAAGACTTCTACCTGTACCCCGGCAAGTACACCTTCGTGGAAACAGCCGCCCCTGACGGC
TATGAGGTGGCCACAGCCATCACCTTCACCGTGAACGAGCAGGGACAGGTCACAGTGAACGGCGCT
AGCACCACGACGCCAGCGCCGCGACCACCAACACCGGCGCCCACCATCGCGTCGCAGCCCCTGTCCC
TGCGCCCAGAGGCGTGCCGGCCAGCGGCGGGGGGCGCAGTGCACACGAGGGGGCTGGACTTCGC
CTGTGATTTTTGGGTGCTGGTGGTGGTTGGTGGAGTCCTGGCTTGCTATAGCTTGCTAGTAACAGTG
GCCTTTATTATTTTCTGGGTGAGGAGTAAGAGGAGCAGGCTCCTGCACAGTGACTACATGAACATGA
CTCCCCGCCGCCCGGGCCCACCCGCAAGCATTACCAGCCCTATGCCCCACCACGCGACTTCGCAGC
CTATCGCTCCATCGATAGAGTGAAGTTCAGCAGGAGCGCAGACGCCCCCGCGTACCAGCAGGGCCA
GAACCAGCTCTATAACGAGCTCAATCTAGGACGAAGAGAGGAGTACGATGTTTTGGACAAGAGACG
TGGCCGGGACCCTGAGATGGGGGGAAAGCCGAGAAGGAAGAACCCTCAGGAAGGCCTGTACAAT
GAACTGCAGAAAGATAAGATGGCGGAGGCCTACAGTGAGATTGGGATGAAAGGCGAGCGCCGGA
GGGGCAAGGGGCACGATGGCCTTTACCAGGGTCTCAGTACAGCCACCAAGGACACCTACGACGCCC
TTCACATGCAGGCCCTGCCCCCTCGCTAA

Amino acid sequence (SEQ ID NO: 6)
MALPVTALLLPLALLLHAARPGSGSGDSATHIKFSKRDEDGKELAGATMELRDSSGKTISTWISDGQVKD
FYLYPGKYTFVETAAPDGYEVATAITFTVNEQGQVTVNGASTTTPAPRPPTPAPTIASQPLSLRPEACRPA
AGGAVHTRGLDFACDFWVLVVVGGVLACYSLLVTVAFIIFWVRSKRSRLLHSDYMNMTPRRPGPTRKH
YQPYAPPRDFAAYRSIDRVKFSRSADAPAYQQGQNQLYNELNLGRREEYDVLDKRRGRDPEMGGKPRR
KNPQEGLYNELQKDKMAEAYSEIGMKGERRRGKGHDGLYQGLSTATKDTYDALHMQALPPR

FIG. 5B

B) Sequence of pELNS(SpeI)-SpyCatcher-GGS-CD28-Zeta

Nucleotide sequence (SEQ ID NO: 7)
ATGGCCTTACCAGTGACCGCCTTGCTCCTGCCGCTGGCCTTGCTGCTCCACGCCGCCAGGCCGGGAT
CCGGAAGCGGCGATAGCGCCACCCACATCAAGTTCAGCAAGCGGGACGAGGACGGCAAAGAGCTG
GCTGGCGCCACCATGGAACTGCGGGACAGCAGCGGCAAGACCATCAGCACCTGGATCAGCGACGG
CCAGGTCAAAGACTTCTACCTGTACCCCGGCAAGTACACCTTCGTGGAAACAGCCGCCCCTGACGGC
TACGAGGTGGCCACAGCCATCACCTTCACCGTGAACGAGCAGGGACAGGTCACAGTGAACGGCGG
CGGCAGCGGCGGCAGCGGCGGCAGCGGCGGCAGCGGCGGCAGCGGCGGCAGCGGCGGCAGCGC
TAGCACCACGACGCCAGCGCCGCGACCACCAACACCGGCGCCCACCATCGCGTCGCAGCCCTGTCC
CTGCGCCCAGAGGCGTGCCGGCCAGCGGCGGGGGCGCAGTGCACACGAGGGGGCTGGACTTCG
CCTGTGATTTTTGGGTGCTGGTGGTGGTTGGTGGAGTCCTGGCTTGCTATAGCTTGCTAGTAACAGT
GGCCTTTATTATTTTCTGGGTGAGGAGTAAGAGGAGCAGGCTCCTGCACAGTGACTACATGAACAT
GACTCCCCGCCGCCCCGGGCCCACCCGCAAGCATTACCAGCCCTATGCCCCACCACGCGACTTCGCA
GCCTATCGCTCCATCGATAGAGTGAAGTTCAGCAGGAGCGCAGACGCCCCCGCGTACCAGCAGGGC
CAGAACCAGCTCTATAACGAGCTCAATCTAGGACGAAGAGAGGAGTACGATGTTTTGGACAAGAGA
CGTGGCCGGGACCCTGAGATGGGGGGAAAGCCGAGAAGGAAGAACCCTCAGGAAGGCCTGTACA
ATGAACTGCAGAAAGATAAGATGGCGGAGGCCTACAGTGAGATTGGGATGAAAGGCGAGCGCCG
GAGGGGCAAGGGGCACGATGGCCTTTACCAGGGTCTCAGTACAGCCACCAAGGACACCTACGACG
CCCTTCACATGCAGGCCCTGCCCCCTCGCTAA

Amino acid sequence (SEQ ID NO: 8)
MALPVTALLLPLALLLHAARPGSGSGDSATHIKFSKRDEDGKELAGATMELRDSSGKTISTWISDGQVKD
FYLYPGKYTFVETAAPDGYEVATAITFTVNEQGQVTVNGGGSGGSGGSGGSGGSGGSGGSASTTTPAPR
PPTPAPTIASQPLSLRPEACRPAAGGAVHTRGLDFACDFWVLVVVGGVLACYSLLVTVAFIIFWVRSKRSR
LLHSDYMNMTPRRPGPTRKHYQPYAPPRDFAAYRSIDRVKFSRSADAPAYQQGQNQLYNELNLGRREE
YDVLDKRRGRDPEMGGKPRRKNPQEGLYNELQKDKMAEAYSEIGMKGERRRGKHDGLYQGLSTATK
DTYDALHMQALPPR

FIG. 6B

B) Sequence of pELNS(SpeI)-eGFP-SpyTag-CD28-Zeta

Nucleotide sequence (SEQ ID NO: 1)
ATGGTGAGCAAGGGCGAGGAGCTGTTCACCGGGGTGGTGCCCATCCTGGTCGAGCTGGACGGCGA
CGTAAACGGCCACAAGTTCAGCGTGTCCGGCGAGGGCGAGGGCGATGCCACCTACGGCAAGCTGA
CCCTGAAGTTCATCTGCACCACCGGCAAGCTGCCCGTGCCCTGGCCCACCCTCGTGACCACCCTGAC
CTACGGCGTGCAGTGCTTCAGCCGCTACCCCGACCACATGAAGCAGCACGACTTCTTCAAGTCCGCC
ATGCCCGAAGGCTACGTCCAGGAGCGCACCATCTTCTTCAAGGACGACGGCAACTACAAGACCCGC
GCCGAGGTGAAGTTCGAGGGCGACACCCTGGTGAACCGCATCGAGCTGAAGGGCATCGACTTCAA
GGAGGACGGCAACATCCTGGGGCACAAGCTGGAGTACAACTACAACAGCCACAACGTCTATATCAT
GGCCGACAAGCAGAAGAACGGCATCAAGGTGAACTTCAAGATCCGCCACAACATCGAGGACGGCA
GCGTGCAGCTCGCCGACCACTACCAGCAGAACACCCCCATCGGCGACGGCCCCGTGCTGCTGCCCG
ACAACCACTACCTGAGCACCCAGTCCGCCCTGAGCAAAGACCCCAACGAGAAGCGCGATCACATGG
TCCTGCTGGAGTTCGTGACCGCCGCCGGGATCACTCTCGGCATGGACGAGCTGTACAAGAGATCTG
GCAGCGGAGAGGGCAGAGGAAGTCTTCTAACATGCGGTGACGTGGAGGAGAATCCCGGCCCTAGA
ATGGCCTTACCAGTGACCGCCTTGCTCCTGCCGCTGGCCTTGCTGCTCCACGCCGCCAGGCCGGGAT
CCGCCCACATTGTGATGGTGGACGCCTACAAGCCCACCAAGGCTAGCACCACGACGCCAGCGCCGC
GACCACCAACACCGGCGCCCACCATCGCGTCGCAGCCCCTGTCCCTGCGCCCAGAGGCGTGCCGGC
CAGCGGCGGGGGGCGCAGTGCACACGAGGGGGCTGGACTTCGCCTGTGATTTTTGGGTGCTGGTG
GTGGTTGGTGGAGTCCTGGCTTGCTATAGCTTGCTAGTAACAGTGGCCTTTATTATTTTCTGGGTGA
GGAGTAAGAGGAGCAGGCTCCTGCACAGTGACTACATGAACATGACTCCCCGCCGCCCCGGGCCCA
CCCGCAAGCATTACCAGCCCTATGCCCCACCACGCGACTTCGCAGCCTATCGCTCCATCGATAGAGT
GAAGTTCAGCAGGAGCGCAGACGCCCCCGCGTACCAGCAGGGCCAGAACCAGCTCTATAACGAGCT
CAATCTAGGACGAAGAGAGGAGTACGATGTTTTGGACAAGAGACGTGGCCGGGACCCTGAGATGG
GGGGAAAGCCGAGAAGGAAGAACCCTCAGGAAGGCCTGTACAATGAACTGCAGAAAGATAAGATG
GCGGAGGCCTACAGTGAGATTGGGATGAAAGGCGAGCGCCGGAGGGGCAAGGGGCACGATGGCC
TTTACCAGGGTCTCAGTACAGCCACCAAGGACACCTACGACGCCCTTCACATGCAGGCCCTGCCCCC
TCGCTAA

Amino acid sequence (SEQ ID NO: 2)
MVSKGEELFTGVVPILVELDGDVNGHKFSVSGEGEGDATYGKLTLKFICTTGKLPVPWPTLVTTLTYGVQ
CFSRYPDHMKQHDFFKSAMPEGYVQERTIFFKDDGNYKTRAEVKFEGDTLVNRIELKGIDFKEDGNILGH
KLEYNYNSHNVYIMADKQKNGIKVNFKIRHNIEDGSVQLADHYQQNTPIGDGPVLLPDNHYLSTQSALS
KDPNEKRDHMVLLEFVTAAGITLGMDELYKRSGSGEGRGSLLTCGDVEENPGPRMALPVTALLLPLALLL
HAARPGSAHIVMVDAYKPTKASTTTPAPRPPTPAPTIASQPLSLRPEACRPAAGGAVHTRGLDFACDFW
VLVVVGGVLACYSLLVTVAFIIFWVRSKRSRLLHSDYMNMTPRRPGPTRKHYQPYAPPRDFAAYRSIDRV
KFSRSADAPAYQQGQNQLYNELNLGRREEYDVLDKRRGRDPEMGGKPRRKNPQEGLYNELQKDKMAE
AYSEIGMKGERRRGKGHDGLYQGLSTATKDTYDALHMQALPPR*

FIG. 7B

B) Sequence of pELNS(SpeI)-eGFP- SpyTag-GGS-CD28-Zeta

Nucleotide sequence (SEQ ID NO: 3)

ATGGTGAGCAAGGGCGAGGAGCTGTTCACCGGGGTGGTGCCCATCCTGGTCGAGCTGGACGGCGA
CGTAAACGGCCACAAGTTCAGCGTGTCCGGCGAGGGCGAGGGCGATGCCACCTACGGCAAGCTGA
CCCTGAAGTTCATCTGCACCACCGGCAAGCTGCCCGTGCCCTGGCCCACCCTCGTGACCACCCTGAC
CTACGGCGTGCAGTGCTTCAGCCGCTACCCCGACCACATGAAGCAGCACGACTTCTTCAAGTCCGCC
ATGCCCGAAGGCTACGTCCAGGAGCGCACCATCTTCTTCAAGGACGACGGCAACTACAAGACCCGC
GCCGAGGTGAAGTTCGAGGGCGACACCCTGGTGAACCGCATCGAGCTGAAGGGCATCGACTTCAA
GGAGGACGGCAACATCCTGGGGCACAAGCTGGAGTACAACTACAACAGCCACAACGTCTATATCAT
GGCCGACAAGCAGAAGAACGGCATCAAGGTGAACTTCAAGATCCGCCACAACATCGAGGACGGCA
GCGTGCAGCTCGCCGACCACTACCAGCAGAACACCCCCATCGGCGACGGCCCCGTGCTGCTGCCCG
ACAACCACTACCTGAGCACCCAGTCCGCCCTGAGCAAAGACCCCAACGAGAAGCGCGATCACATGG
TCCTGCTGGAGTTCGTGACCGCCGCCGGGATCACTCTCGGCATGGACGAGCTGTACAAGAGATCTG
GCAGCGGAGAGGGCAGAGGAAGTCTTCTAACATGCGGTGACGTGGAGGAGAATCCCGGCCCTAGA
ATGGCCTTACCAGTGACCGCCTTGCTCCTGCCGCTGGCCTTGCTGCTCCACGCCGCCAGGCCGGGAT
CCGCCCACATCGTGATGGTGGACGCCTACAAGCCCACCAAGGGCGGCAGCGGCGGCAGCGGCGGC
AGCGGCGGCAGCGGCGGCAGCGGCGGCAGCGGCGGCAGCGCTAGCACCACGACGCCAGCGCCGC
GACCACCAACACCGGCGCCCACCATCGCGTCGCAGCCCCTGTCCCTGCGCCCAGAGGCGTGCCGGC
CAGCGGCGGGGGCGCAGTGCACACGAGGGGGCTGGACTTCGCCTGTGATTTTGGGTGCTGGTG
GTGGTTGGTGGAGTCCTGGCTTGCTATAGCTTGCTAGTAACAGTGGCCTTTATTATTTTCTGGGTGA
GGAGTAAGAGGAGCAGGCTCCTGCACAGTGACTACATGAACATGACTCCCCGCCGCCCCGGGCCCA
CCCGCAAGCATTACCAGCCCTATGCCCCACCACGCGACTTCGCAGCCTATCGCTCCATCGATAGAGT
GAAGTTCAGCAGGAGCGCAGACGCCCCCGCGTACCAGCAGGGCCAGAACCAGCTCTATAACGAGCT
CAATCTAGGACGAAGAGAGGAGTACGATGTTTTGGACAAGAGACGTGGCCGGGACCCTGAGATGG
GGGGAAAGCCGAGAAGGAAGAACCCTCAGGAAGGCCTGTACAATGAACTGCAGAAAGATAAGATG
GCGGAGGCCTACAGTGAGATTGGGATGAAAGGCGAGCGCCGGAGGGGCAAGGGGCACGATGGCC
TTTACCAGGGTCTCAGTACAGCCACCAAGGACACCTACGACGCCCTTCACATGCAGGCCCTGCCCCC
TCGCTAA

Amino acid sequence (SEQ ID NO: 4)

MVSKGEELFTGVVPILVELDGDVNGHKFSVSGEGEGDATYGKLTLKFICTTGKLPVPWPTLVTTLTYGVQ
CFSRYPDHMKQHDFFKSAMPEGYVQERTIFFKDDGNYKTRAEVKFEGDTLVNRIELKGIDFKEDGNILGH
KLEYNYNSHNVYIMADKQKNGIKVNFKIRHNIEDGSVQLADHYQQNTPIGDPVLLPDNHYLSTQSALS
KDPNEKRDHMVLLEFVTAAGITLGMDELYKRSGSGEGRGSLLTCGDVEENPGPRMALPVTALLLPLALLL
HAARPGSAHIVMVDAYKPTKGGSGGSGGSGGSGGSGGSGGSASTTTPAPRPPTPAPTIASQPLSLRPEA
CRPAAGGAVHTRGLDFACDFWVLVVVGGVLACYSLLVTVAFIIFWVRSKRSLLHSDYMNMTPRRPGP
TRKHYQPYAPPRDFAAYRSIDRVKFSRSADAPAYQQGQNQLYNELNLGRREEYDVLDKRRGRDPEMGG
KPRRKNPQEGLYNELQKDKMAEAYSEIGMKGERRRGKGHDGLYQGLSTATKDTYDALHMQALPPR

FIG. 8B

B) Sequence of pELNS(SpeI)-GFP-SpyCatcher-CD28-Zeta

Nucleotide sequence (SEQ ID NO: 13)

ATGGTGAGCAAGGGCGAGGAGCTGTTCACCGGGGTGGTGCCCATCCTGGTCGAGCTGGACGGCGA
CGTAAACGGCCACAAGTTCAGCGTGTCCGGCGAGGGCGAGGGCGATGCCACCTACGGCAAGCTGA
CCCTGAAGTTCATCTGCACCACCGGCAAGCTGCCCGTGCCCTGGCCCACCCTCGTGACCACCCTGAC
CTACGGCGTGCAGTGCTTCAGCCGCTACCCCGACCACATGAAGCAGCACGACTTCTTCAAGTCCGCC
ATGCCCGAAGGCTACGTCCAGGAGCGCACCATCTTCTTCAAGGACGACGGCAACTACAAGACCCGC
GCCGAGGTGAAGTTCGAGGGCGACACCCTGGTGAACCGCATCGAGCTGAAGGGCATCGACTTCAA
GGAGGACGGCAACATCCTGGGGCACAAGCTGGAGTACAACTACAACAGCCACAACGTCTATATCAT
GGCCGACAAGCAGAAGAACGGCATCAAGGTGAACTTCAAGATCCGCCACAACATCGAGGACGGCA
GCGTGCAGCTCGCCGACCACTACCAGCAGAACACCCCCATCGGCGACGGCCCCGTGCTGCTGCCCG
ACAACCACTACCTGAGCACCCAGTCCGCCCTGAGCAAAGACCCCAACGAGAAGCGCGATCACATGG
TCCTGCTGGAGTTCGTGACCGCCGCCGGGATCACTCTCGGCATGGACGAGCTGTACAAGAGATCTG
GCAGCGGAGAGGGCAGAGGAAGTCTTCTAACATGCGGTGACGTGGAGGAGAATCCCGGCCCTAGA
ATGGCCTTACCAGTGACCGCCTTGCTCCTGCCGCTGGCCTTGCTGCTCCACGCCGCCAGGCCGGGAT
CCGGAAGCGGAGATAGCGCCACCCACATCAAGTTCAGCAAGCGGGACGAGGACGGCAAAGAGCTG
GCTGGCGCCACCATGGAACTGCGGGATAGCAGCGGCAAGACCATCAGCACCTGGATCAGCGACGG
CCAGGTCAAAGACTTCTACCTGTACCCCGGCAAGTACACCTTCGTGGAAACAGCCGCCCCTGACGGC
TATGAGGTGGCCACAGCCATCACCTTCACCGTGAACGAGCAGGGACAGGTCACAGTGAACGGCGCT
AGCACCACGACGCCAGCGCCGCGACCACCAACACCGGCGCCCACCATCGCGTCGCAGCCCCTGTCCC
TGCGCCCAGAGGCGTGCCGGCCAGCGGCGGGGGCGCAGTGCACACGAGGGGGCTGGACTTCGC
CTGTGATTTTTGGGTGCTGGTGGTGGTTGGTGGAGTCCTGGCTTGCTATAGCTTGCTAGTAACAGTG
GCCTTTATTATTTTCTGGGTGAGGAGTAAGAGGAGCAGGCTCCTGCACAGTGACTACATGAACATGA
CTCCCCGCCGCCCCGGGCCCACCCGCAAGCATTACCAGCCCTATGCCCCACCACGCGACTTCGCAGC
CTATCGCTCCATCGATAGAGTGAAGTTCAGCAGGAGCGCAGACGCCCCCGCGTACCAGCAGGGCCA
GAACCAGCTCTATAACGAGCTCAATCTAGGACGAAGAGAGGAGTACGATGTTTTGGACAAGAGACG
TGGCCGGGACCCTGAGATGGGGGGAAAGCCGAGAAGGAAGAACCCTCAGGAAGGCCTGTACAAT
GAACTGCAGAAGATAAGATGGCGGAGGCCTACAGTGAGATTGGGATGAAAGGCGAGCGCCGGA
GGGGCAAGGGGCACGATGGCCTTTACCAGGGTCTCAGTACAGCCACCAAGGACACCTACGACGCCC
TTCACATGCAGGCCCTGCCCCCTCGCTAA

Amino acid sequence (SEQ ID NO: 14)

MVSKGEELFTGVVPILVELDGDVNGHKFSVSGEGEGDATYGKLTLKFICTTGKLPVPWPTLVTTLTYGVQ
CFSRYPDHMKQHDFFKSAMPEGYVQERTIFFKDDGNYKTRAEVKFEGDTLVNRIELKGIDFKEDGNILGH
KLEYNYNSHNVYIMADKQKNGIKVNFKIRHNIEDGSVQLADHYQQNTPIGDPVLLPDNHYLSTQSALS
KDPNEKRDHMVLLEFVTAAGITLGMDELYKRSGSGEGRGSLLTCGDVEENPGPRMALPVTALLLPLALLL
HAARPGSGSGDSATHIKFSKRDEDGKELAGATMELRDSSGKTISTWISDGQVKDFYLYPGKYTFVETAAP
DGYEVATAITFTVNEQGQVTVNGASTTTPAPRPPTPAPTIASQPLSLRPEACRPAAGGAVHTRGLDFACD
FWVLVVVGGVLACYSLLVTVAFIIFWVRSKRSLLHSDYMNMTPRRPGPTRKHYQPYAPPRDFAAYRSID
RVKFSRSADAPAYQQGQNQLYNELNLGRREEYDVLDKRRGRDPEMGGKPRRKNPQEGLYNELQKDKM
AEAYSEIGMKGERRRGKGHDGLYQGLSTATKDTYDALHMQALPPR

FIG. 9B

B) Sequence of pELNS(SpeI)-GFP-SpyCatcher-GGS-CD28-Zeta

Nucleotide sequence (SEQ ID NO: 15)
ATGGTGAGCAAGGGCGAGGAGCTGTTCACCGGGGTGGTGCCCATCCTGGTCGAGCTGGACGGCGA
CGTAAACGGCCACAAGTTCAGCGTGTCCGGCGAGGGCGAGGGCGATGCCACCTACGGCAAGCTGA
CCCTGAAGTTCATCTGCACCACCGGCAAGCTGCCCGTGCCCTGGCCCACCCTCGTGACCACCCTGAC
CTACGGCGTGCAGTGCTTCAGCCGCTACCCCGACCACATGAAGCAGCACGACTTCTTCAAGTCCGCC
ATGCCCGAAGGCTACGTCCAGGAGCGCACCATCTTCTTCAAGGACGACGGCAACTACAAGACCCGC
GCCGAGGTGAAGTTCGAGGGCGACACCCTGGTGAACCGCATCGAGCTGAAGGGCATCGACTTCAA
GGAGGACGGCAACATCCTGGGGCACAAGCTGGAGTACAACTACAACAGCCACAACGTCTATATCAT
GGCCGACAAGCAGAAGAACGGCATCAAGGTGAACTTCAAGATCCGCCACAACATCGAGGACGGCA
GCGTGCAGCTCGCCGACCACTACCAGCAGAACACCCCCATCGGCGACGGCCCCGTGCTGCTGCCCG
ACAACCACTACCTGAGCACCCAGTCCGCCCTGAGCAAAGACCCCAACGAGAAGCGCGATCACATGG
TCCTGCTGGAGTTCGTGACCGCCGCCGGGATCACTCTCGGCATGGACGAGCTGTACAAGAGATCTG
GCAGCGGAGAGGGCAGAGGAAGTCTTCTAACATGCGGTGACGTGGAGGAGAATCCCGGCCCTAGA
ATGGCCTTACCAGTGACCGCCTTGCTCCTGCCGCTGGCCTTGCTGCTCCACGCCGCCAGGCCGGGAT
CCGGAAGCGGCGATAGCGCCACCCACATCAAGTTCAGCAAGCGGGACGAGGACGGCAAAGAGCTG
GCTGGCGCCACCATGGAACTGCGGGACAGCAGCGGCAAGACCATCAGCACCTGGATCAGCGACGG
CCAGGTCAAAGACTTCTACCTGTACCCCGGCAAGTACACCTTCGTGGAAACAGCCGCCCCTGACGGC
TACGAGGTGGCCACAGCCATCACCTTCACCGTGAACGAGCAGGGACAGGTCACAGTGAACGGCGG
CGGCAGCGGCGGCAGCGGCGGCAGCGGCGGCAGCGGCGGCAGCGGCGGCAGCGGCGGCAGCGC
TAGCACCACGACGCCAGCGCCGCGACCACCAACACCGGCGCCCACCATCGCGTCGCAGCCCCTGTCC
CTGCGCCCAGAGGCGTGCCGGCCAGCGGCGGGGGCGCAGTGCACACGAGGGGGCTGGACTTCG
CCTGTGATTTTTGGGTGCTGGTGGTGGTTGGTGGAGTCCTGGCTTGCTATAGCTTGCTAGTAACAGT
GGCCTTTATTATTTTCTGGGTGAGGAGTAAGAGGAGCAGGCTCCTGCACAGTGACTACATGAACAT
GACTCCCCGCCGCCCCGGGCCCACCCGCAAGCATTACCAGCCCTATGCCCCACCACGCGACTTCGCA
GCCTATCGCTCCATCGATAGAGTGAAGTTCAGCAGGAGCGCAGACGCCCCCGCGTACCAGCAGGGC
CAGAACCAGCTCTATAACGAGCTCAATCTAGGACGAAGAGAGGAGTACGATGTTTTGGACAAGAGA
CGTGGCCGGGACCCTGAGATGGGGGGAAAGCCGAGAAGGAAGAACCCTCAGGAAGGCCTGTACA
ATGAACTGCAGAAAGATAAGATGGCGGAGGCCTACAGTGAGATTGGGATGAAAGGCGAGCGCCG
GAGGGGCAAGGGGCACGATGGCCTTTACCAGGGTCTCAGTACAGCCACCAAGGACACCTACGACG
CCCTTCACATGCAGGCCCTGCCCCCTCGCTAA

Amino acid sequence (SEQ ID NO: 16)
MVSKGEELFTGVVPILVELDGDVNGHKFSVSGEGEGDATYGKLTLKFICTTGKLPVPWPTLVTTLTYGVQ
CFSRYPDHMKQHDFFKSAMPEGYVQERTIFFKDDGNYKTRAEVKFEGDTLVNRIELKGIDFKEDGNILGH
KLEYNYNSHNVYIMADKQKNGIKVNFKIRHNIEDGSVQLADHYQQNTPIGDGPVLLPDNHYLSTQSALS
KDPNEKRDHMVLLEFVTAAGITLGMDELYKRSGSGEGRGSLLTCGDVEENPGPRMALPVTALLLPLALLL
HAARPGSGSGDSATHIKFSKRDEDGKELAGATMELRDSSGKTISTWISDGQVKDFYLYPGKYTFVETAAP
DGYEVATAITFTVNEQGQVTVNGGSGGSGGSGGSGGSGGSGGSASTTTPAPRPPTPAPTIASQPLSLR
PEACRPAAGGAVHTRGLDFACDFWVLVVVGGVLACYSLLVTVAFIIFWVRSKRSRLLHSDYMNMTPRRP
GPTRKHYQPYAPPRDFAAYRSIDRVKFSRSADAPAYQQGQNQLYNELNLGRREEYDVLDKRRGRDPEM
GGKPRRKNPQEGLYNELQKDKMAEAYSEIGMKGERRRGKGHDGLYQGLSTATKDTYDALHMQALPPR

FIG. 10B

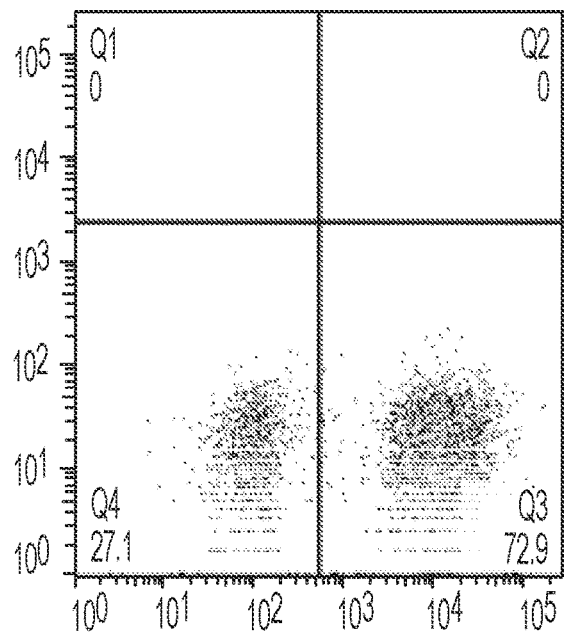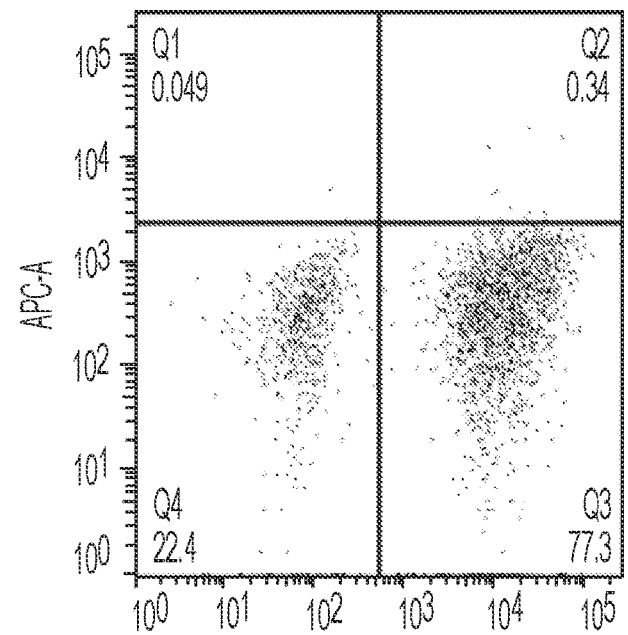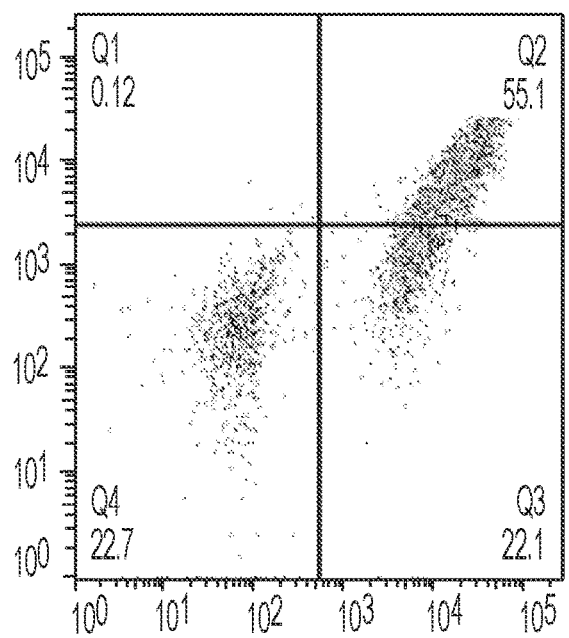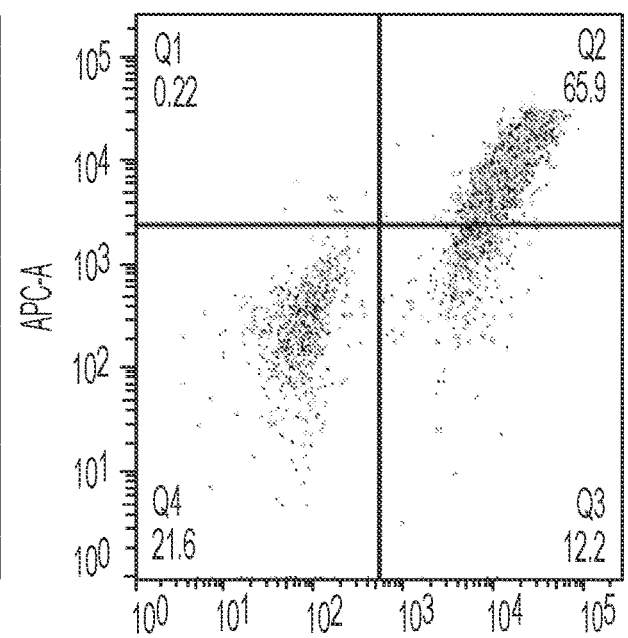
FIG. 16A

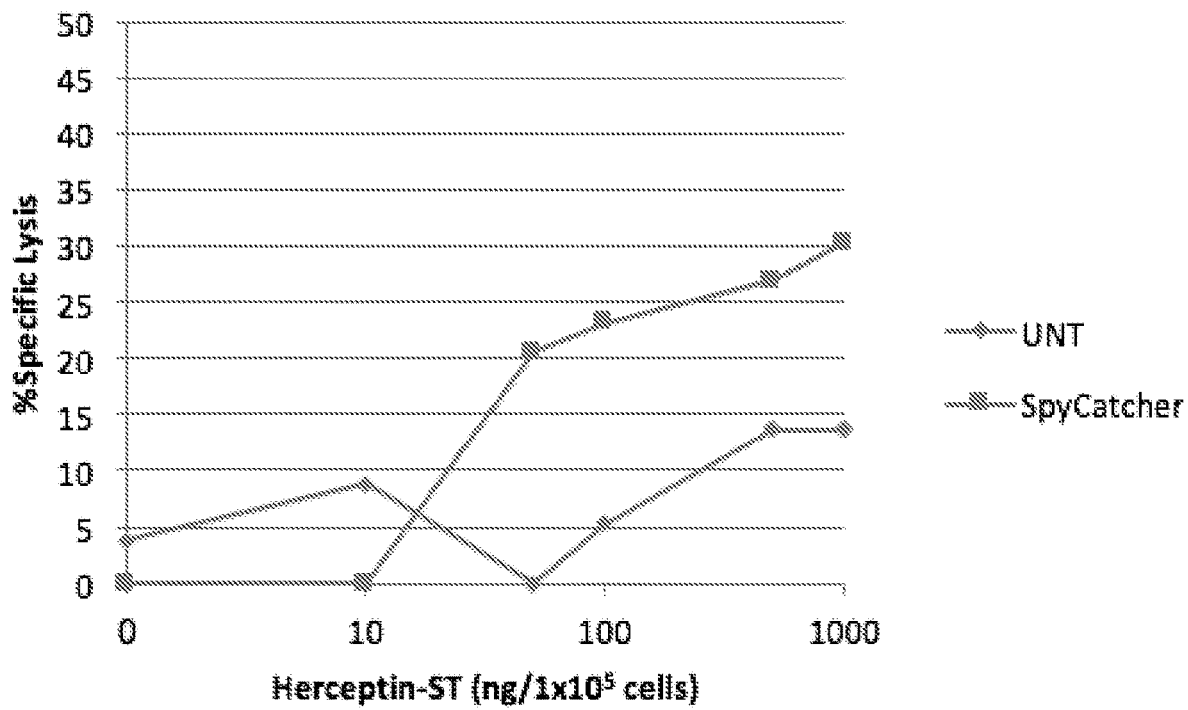
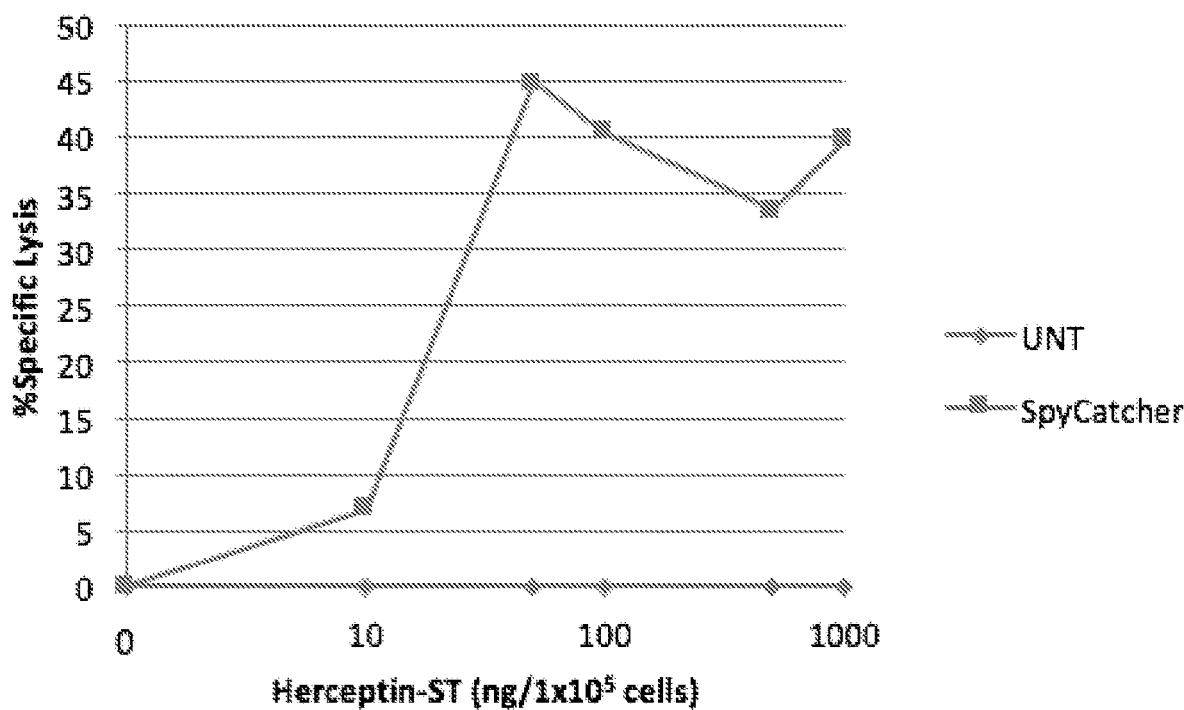
FIG. 17

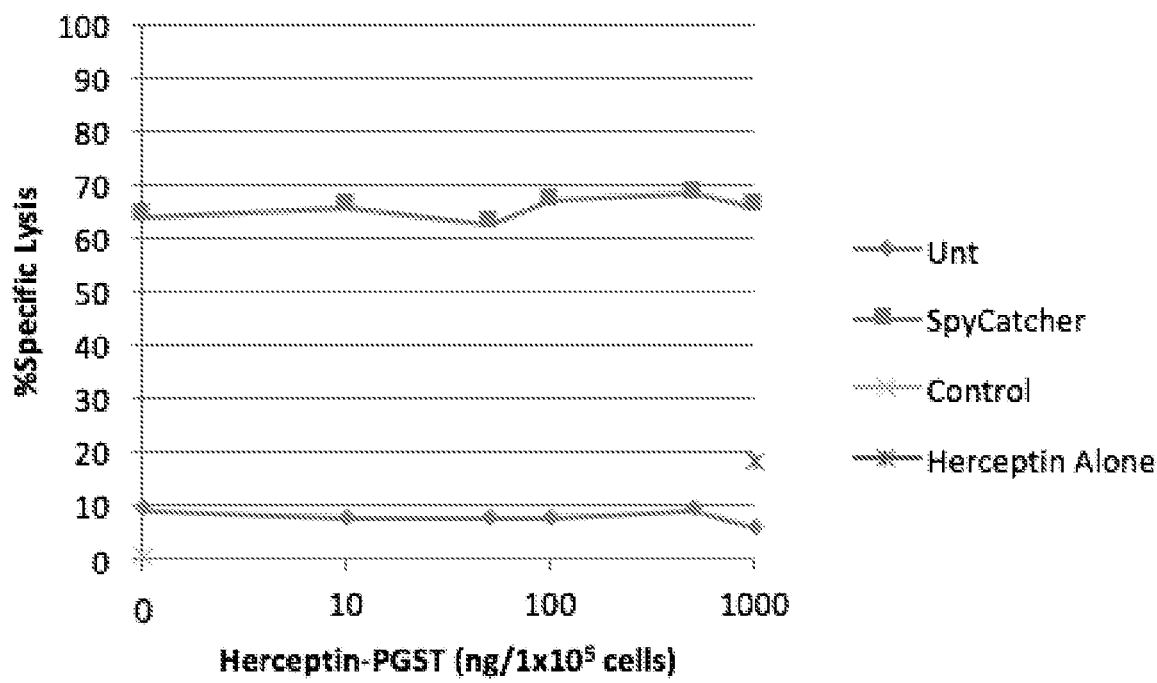
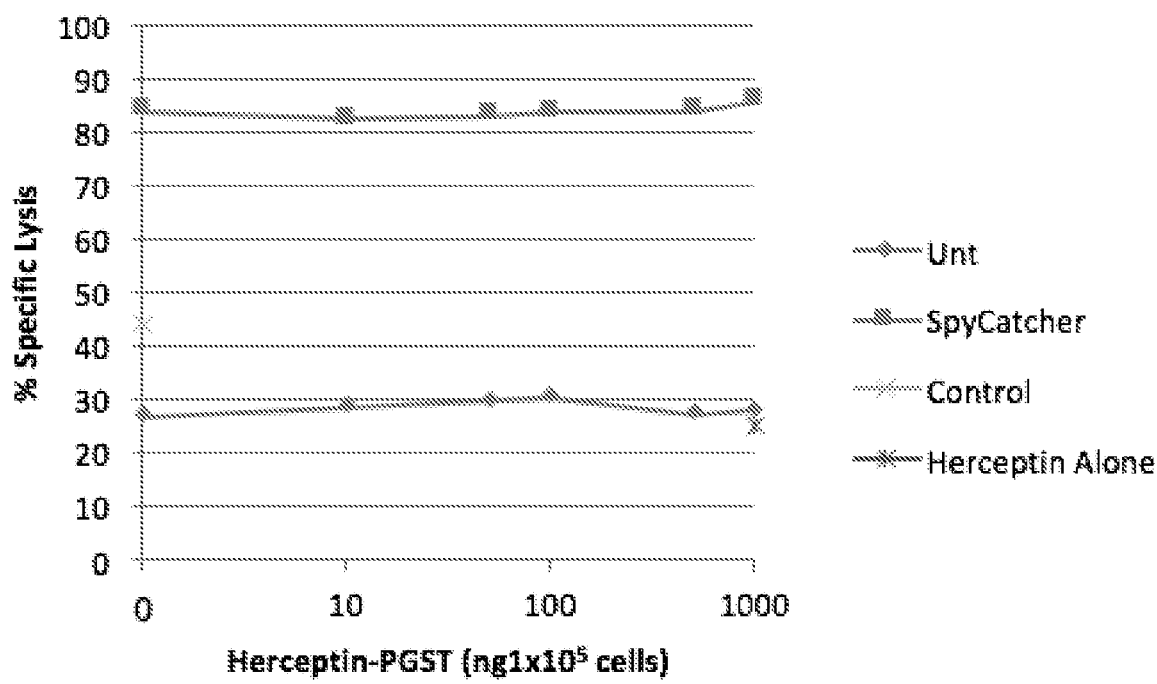
FIG. 19

SPYCATCHER AND SPYTAG: UNIVERSAL IMMUNE RECEPTORS FOR T CELLS

CROSS-REFERENCE TO RELATED APPLICATIONS

The present application is a 35 U.S.C. § 371 national phase application from, and claims priority to, International Application No. PCT/US2016/068055, filed Dec. 21, 2016 and published under PCT Article 21(2) in English, which claims priority under 35 U.S.C. § 119(e) to U.S. Provisional Patent Application No. 62/271,071, filed Dec. 22, 2015, which are hereby incorporated by reference in their entirety herein.

STATEMENT REGARDING FEDERALLY SPONSORED RESEARCH OR DEVELOPMENT

This invention was made with government support under grant CA168900 and CA187657 awarded by the National Institute of Health. The government has certain rights in the invention.

BACKGROUND OF THE INVENTION

Adoptive cell transfer (ACT) therapy using bioengineered T cells continues to show significant promise in the treatment of various diseases such as cancer, viral infections or auto-immune diseases. T cells can be engineered to express a synthetic immunoreceptor comprised of an extracellular targeted antibody and intracellular signaling domain, known as chimeric antigen receptor (CAR). Despite encouraging results, significant challenges still exist to widespread CAR application. For instance, some tumors are heterogeneous in antigen expression, differing among individuals, but also in the same patient. Additionally, tumor cells commonly lose cell surface antigen expression during malignant disease progression. Antigen loss is one major factor contributing to tumor relapse following specific therapy that had been initially effective. Alternatively, targeting of tumor-associated antigens (TAAs) expressed at low levels on normal tissue cells can result in specific toxicity, leading to the retirement of costly vectors. However, many CARs have a fixed antigen specificity such that only one TAA can be targeted, limiting the efficacy that can be achieved due to heterogeneous TAA expression. Broad application and improved success of CARs in the clinic would necessitate a panel of bioengineered T cells with different specificities, custom-made for each individual. For this reason, a more generalized and effective application of CAR therapy would benefit from the capability to produce large panels of CARs against many known TAAs. However, practically speaking, this approach is technically and economically challenging (Kohn et al., 2011, Mol. Ther. 19:432-438).

The use of peptides and peptide-like molecules as tags for attaching to proteins and other entities is a key tool for basic and applied medical research. Peptide tags can allow the detection, purification and analysis of a particular protein or entity or can be used for the specific targeting of the tagged protein or entity. Thus, the use of peptide tags which are capable of associating with a binding partner can provide a means for manipulating or analyzing a target protein or entity; this analysis can be used to determine the size, abundance, location in the cell or organism, and the interactions of the tagged protein. One major problem with the use of most peptide or protein tags known in the art is the instability of the interactions with their binding partners, due to the non-covalent nature of this interaction.

There is a clear need in the art for compositions and methods for immune therapies targeting any antigen with a high and strong binding affinity. The present invention addresses this unmet need in the art.

SUMMARY OF THE INVENTION

The invention includes an isolated nucleic acid sequence encoding a universal immune receptor, wherein the universal immune receptor comprises either a SpyCatcher or a SpyTag extracellular binding domain bound to an extracellular hinge region, which is in turn bound to a transmembrane domain which is in turn bound to a T cell receptor intracellular signaling domain. In certain embodiments, a SpyCatcher extracellular binding domain is bound to the extracellular hinge domain. In other embodiments, a SpyTag extracellular binding domain is bound to the extracellular hinge domain. In yet other embodiments, the universal immune receptor comprises a nucleic acid sequence selected from the group consisting of SEQ ID Nos: 1, 3, 5, 7, 9, 11, 13 and 15, or selected from the group consisting of SEQ ID Nos: 5, 7, 13 and 15, or selected from the group consisting of SEQ ID Nos: 1, 3, 9 and 11. In yet other embodiments, the T cell receptor intracellular signaling domain further comprises a costimulatory molecule. In additional embodiments, the T cell receptor intracellular signaling domain substantially lacks signaling capacity. In other embodiments, the intracellular domain of the costimulatory molecule is selected from the group consisting of CD27, CD28, CD2, CD3, 4-1BB, OX40, CD30, CD40, PD-1, ICOS, lymphocyte function-associated antigen-1 (LFA-1), CD7, LIGHT, NKG2C, B7-H3, a ligand that specifically binds with CD83, and any combination thereof.

Further included in the invention is an isolated nucleic acid sequence encoding either a SpyCatcher or a SpyTag linked to a molecule comprising at least one selected from the group consisting of an oligonucleotide, an antibody, an antibody fragment, a scFv, a protein scaffold, a peptide, a ligand, an aptamer, a labelling agent, a tumor antigen, a self-antigen, a viral antigen, and any combination thereof. In some embodiments, the labelling agent is selected from the group consisting of myc-tag, FLAG-tag, His-tag, HA-tag, a fluorescent protein (e.g. green fluorescent protein (GFP)), a fluorophore (e.g. tetramethylrhodamine (TRITC), fluorescein isothiocyanate (FITC)), dinitrophenol, peridinin chlorophyll protein complex, green fluorescent protein, phycoerythrin (PE), histidine, biotin, streptavidin, avidin, horse radish peroxidase, palmitoylation, nitrosylation, alkalanine phosphatase, glucose oxidase, Glutathione S-transferase (GST), maltose binding protein, a radioisotope, and any types of compounds used for radioisotope labeling including, 1,4,7,10-tetraazacyclododecane-1,4,7,10-tetraacetic acid (DOTA), diethylene triamine pentaacetic acid (DTPA), and 1,4,7-triazacyclononane-1,4,7-triacetic acid (NOTA).

Also included in the invention is an isolated universal immune receptor comprising either a SpyCatcher or a SpyTag extracellular binding domain bound to an extracellular hinge region, which is in turn bound to a transmembrane domain which is in turn bound to a T cell receptor intracellular signaling domain. In some embodiments, a SpyCatcher extracellular binding domain is bound to the extracellular hinge domain. In other embodiments, a SpyTag extracellular binding domain is bound to the extracellular hinge domain. In yet further embodiments, the universal immune receptor comprises an amino acid sequence selected from the group consisting of SEQ ID Nos: 2, 4, 6, 8, 10, 12, 14 and 16, or selected from the group consisting of SEQ ID Nos: 6, 8, 14 and 16, or selected from the group consisting of SEQ ID Nos: 2, 4, 10 and 12. In additional embodiments, the T cell receptor intracellular signaling domain further comprises a costimulatory molecule. In other embodiments, the intracellular domain of the costimulatory molecule is selected from the group consisting of CD27, CD28, CD2, CD3, 4-1BB, OX40, CD30, CD40, PD-1, ICOS, lymphocyte function-associated antigen-1 (LFA-1), CD7, LIGHT, NKG2C, B7-H3, a ligand that specifically binds with CD83, and any combination thereof. In yet other embodiments, the isolated universal immune receptor is bound to a composition comprising either a SpyTag- or a SpyCatcher-bound molecule. In certain embodiments, the SpyTag- or SpyCatcher-bound molecule comprises at least one selected from the group consisting of an oligonucleotide, an antibody, an antibody fragment, a scFv, a protein scaffold, a peptide, a ligand, an aptamer, a labelling agent, a tumor antigen, a self-antigen, a viral antigen, and any combination thereof. In some embodiments, the labelling agent is selected from the group consisting of myc-tag, FLAG-tag, His-tag, HA-tag, a fluorescent protein (e.g. green fluorescent protein (GFP)), a fluorophore (e.g. tetramethylrhodamine (TRITC), fluorescein isothiocyanate (FITC)), dinitrophenol, peridinin chlorophyll protein complex, phycoerythrin (PE), histidine, biotin, streptavidin, avidin, horse radish peroxidase, palmitoylation, nitrosylation, alkalanine phosphatase, glucose oxidase, Glutathione S-transferase (GST), maltose binding protein, a radioisotope, and any types of compounds used for radioisotope labeling including, 1,4,7,10-tetraazacyclododecane-1,4,7,10-tetraacetic acid (DOTA), diethylene triamine pentaacetic acid (DTPA), and 1,4,7-triazacyclononane-1,4,7-triacetic acid (NOTA).

Also included in the invention is a cell comprising a nucleic acid sequence of sequence encoding a universal immune receptor, wherein the universal immune receptor comprises either a SpyCatcher or a SpyTag extracellular binding domain bound to an extracellular hinge region, which is in turn bound to a transmembrane domain which is in turn bound to a T cell receptor intracellular signaling domain. In certain embodiments, a SpyCatcher extracellular binding domain is bound to the extracellular hinge domain. In other embodiments, a SpyTag extracellular binding domain is bound to the extracellular hinge domain. In yet additional embodiments, the cell is selected from the group consisting of a T cell, a Natural Killer (NK) cell, a cytotoxic T lymphocyte (CTL), a macrophage, a stem cell, and a regulatory T cell. In other embodiments, the cell is activated when the encoded isolated universal immune receptor binds to a composition comprising either a SpyTag- or a SpyCatcher-bound molecule. In additional embodiments, the SpyTag- or SpyCatcher-bound molecule comprises at least one selected from the group consisting of an oligonucleotide, an antibody, an antibody fragment, a scFv, a protein scaffold, a peptide, a receptor, a ligand, an aptamer, a labelling agent, a tumor antigen, a self-antigen, a viral antigen, and any combination thereof. In yet other embodiments, the labelling agent is selected from the group consisting of myc-tag, FLAG-tag, His-tag, HA-tag, a fluorescent protein (e.g. green fluorescent protein (GFP)), a fluorophore (e.g. tetramethylrhodamine (TRITC), fluorescein isothiocyanate (FITC)), dinitrophenol, peridinin chlorophyll protein complex, phycoerythrin (PE), histidine, biotin, streptavidin, avidin, horse radish peroxidase, palmitoylation, nitrosylation, alkalanine phosphatase, glucose oxidase, Glutathione S-transferase (GST), maltose binding protein, a radioisotope, and any types of compounds used for radioisotope labeling including, 1,4,7,10-tetraazacyclododecane-1,4,7,10-tetraacetic acid (DOTA), diethylene triamine pentaacetic acid (DTPA), and 1,4,7-triazacyclononane-1,4,7-triacetic acid (NOTA).

Also included in the invention is a vector comprising a nucleic acid sequence encoding a universal immune receptor, wherein the universal immune receptor comprises either a SpyCatcher or a SpyTag extracellular binding domain bound to an extracellular hinge region, which is in turn bound to a transmembrane domain which is in turn bound to a T cell receptor intracellular signaling domain. In some embodiments, a SpyCatcher extracellular binding domain is bound to the extracellular hinge domain. In other embodiments, a SpyTag extracellular binding domain is bound to the extracellular hinge domain. In yet further embodiments, the encoded isolated universal immune receptor can bind to a composition comprising either a SpyTag- or a SpyCatcher-bound molecule. In additional embodiments, the SpyTag- or SpyCatcher-bound molecule comprises at least one selected from the group consisting of an oligonucleotide, an antibody, an antibody fragment, a scFv, a protein scaffold, a peptide, a receptor, a ligand, an aptamer, a labelling agent, a tumor antigen, a self-antigen, a viral antigen, and any combination thereof. In yet other embodiments, the labelling agent is selected from the group consisting of myc-tag, FLAG-tag, His-tag, HA-tag, fluorescent protein (e.g. green fluorescent protein (GFP)), a fluorophore (e.g. tetramethylrhodamine (TRITC), fluorescein isothiocyanate (FITC)), dinitrophenol, peridinin chlorophyll protein complex, green fluorescent protein, phycoerythrin (PE), histidine, biotin, streptavidin, avidin, horse radish peroxidase, palmitoylation, nitrosylation, alkalanine phosphatase, glucose oxidase, Glutathione S-transferase (GST), maltose binding protein, a radioisotope, and any types of compounds used for radioisotope labeling including, 1,4,7,10-tetraazacyclododecane-1,4,7,10-tetraacetic acid (DOTA), diethylene triamine pentaacetic acid (DTPA), and 1,4,7-triazacyclononane-1,4,7-triacetic acid (NOTA).

Also included in the invention is a method for stimulating a universal immune receptor-mediated immune response in a mammal, the method comprising administering to a mammal an effective amount of a cell genetically modified to express a universal immune receptor, wherein the universal immune receptor comprises either a SpyCatcher or a SpyTag extracellular binding domain bound to an extracellular hinge region, which is in turn bound to a transmembrane domain which is in turn bound to a T cell receptor intracellular signaling domain. In certain embodiments, a SpyCatcher extracellular binding domain is bound to the extracellular hinge domain. In other embodiments, a SpyTag extracellular binding domain is bound to the extracellular hinge domain. In other embodiments, the universal immune receptor comprises an amino acid sequence selected from the group consisting of SEQ ID Nos: 2, 4, 6, 8, 10, 12, 14 and 16, or selected from the group consisting of SEQ ID Nos: 6, 8, 14 and 16, or selected from the group consisting of SEQ ID Nos: 2, 4, 10 and 12. In additional embodiments, the universal immune receptor further comprises an intracellular domain of a costimulatory molecule. In further embodiments, the intracellular domain of a costimulatory molecule is selected from the group consisting of CD27, CD28, CD2, CD3, 4-1BB, OX40, CD30, CD40, PD-1, ICOS, lymphocyte function-associated antigen-1 (LFA-1), CD7, LIGHT, NKG2C, B7-H3, a ligand that specifically binds with CD83, and any combination thereof. In other embodiments, the universal immune receptor-mediated immune response is stimulated when the isolated universal immune receptor binds to a composition comprising either a SpyTag- or a SpyCatcher-bound molecule. In yet other embodiments, the SpyTag- or SpyCatcher-bound molecule comprises at least one selected from the group consisting of an oligonucleotide, an antibody, an antibody fragment, a scFv, a protein scaffold, a peptide, a receptor, a ligand, an aptamer, a labelling agent, a tumor antigen, a self-antigen, a viral antigen, and any combination thereof. In further embodiments, the labelling agent is selected from the group consisting of myc-tag, FLAG-tag, His-tag, HA-tag, a fluorescent protein (e.g. green fluorescent protein (GFP)), a fluorophore (e.g. tetramethylrhodamine (TRITC), fluorescein isothiocyanate (FITC)), dinitrophenol, peridinin chlorophyll protein complex, green fluorescent protein, phycoerythrin (PE), histidine, biotin, streptavidin, avidin, horse radish peroxidase, palmitoylation, nitrosylation, alkalanine phosphatase, glucose oxidase, Glutathione S-transferase (GST), maltose binding protein, a radioisotope, and any types of compounds used for radioisotope labeling including, 1,4,7,10-tetraazacyclododecane-1,4,7,10-tetraacetic acid (DOTA), diethylene triamine pentaacetic acid (DTPA), and 1,4,7-triazacyclononane-1,4,7-triacetic acid (NOTA). In yet additional embodiments, the method comprises administering either a SpyTag- or a SpyCatcher-bound molecule to the mammal prior to administering the genetically modified cell to the mammal. In other embodiments, the method comprises administering a plurality of SpyTag- or SpyCatcher-bound molecules to the mammal prior to administering the genetically modified cell to the mammal. In yet other embodiments, the method comprises sequentially administering a plurality of SpyTag- or SpyCatcher-bound molecules to the mammal prior to administering the genetically modified cell to the mammal. In additional embodiments, the method comprises binding the universal immune receptor with either a SpyTag- or a SpyCatcher-bound molecule prior to administering the genetically modified cell to the mammal. In further embodiments, the method comprises binding the universal immune receptor with a plurality of SpyTag- or SpyCatcher-bound molecules prior to administering the genetically modified cell to the mammal. In yet other embodiments, the method comprises sequentially binding the universal immune receptor with a plurality of SpyTag- or SpyCatcher-bound molecules prior to administering the genetically modified cell to the mammal. In other embodiments, the cell is an autologous cell and in additional embodiments, the cell is selected from the group consisting of a T cell, a Natural Killer (NK) cell, a cytotoxic T lymphocyte (CTL), a macrophage, a stem cell, and a regulatory T cell.

In further embodiments, there is provided a method of treating a mammal in need thereof, the method comprising administering to the mammal an effective amount of the cell as disclosed and claimed herein. In additional embodiments, the mammal is treated for a disorder selected from the group consisting of a viral, a bacterial and a parasitic infection, an autoimmune disease and a cancer.

BRIEF DESCRIPTION OF THE DRAWINGS

The following detailed description of preferred embodiments of the invention will be better understood when read in conjunction with the appended drawings. For the purpose of illustrating the invention, there are examples shown in the drawings embodiments which are presently preferred. It should be understood, however, that the invention is not limited to the precise arrangements and instrumentalities of the embodiments shown in the drawings.

FIG. 1A: Schematic representation of SpyCatcher and SpyTag immune receptor constructs. FIG. 1B: All Spy immune receptor constructs were constructed in the same manner, with the only changes being the Spy insert between the CD8 leader and CD8 hinge.

FIG. 2 is a table listing the SpyTag and SpyCatcher constructs tested in the present invention.

FIGS. 3A-3B are a series of schematic representations of the map of the construct pELNS(SpeI)-SpyTag-CD28-Zeta (FIG. 3A) and its nucleotide (SEQ ID NO: 9) and amino acid (SEQ ID NO: 10) sequences (FIG. 3B).

FIGS. 4A-4B are a series of schematic representations of the map of the construct: pELNS(SpeI)-SpyTag-GGS-CD28-Zeta and its nucleotide (SEQ ID NO: 11) and amino acid (SEQ ID NO: 12) sequences (FIG. 4B).

FIGS. 5A-5B are a series of schematic representations of the map of the construct: pELNS(SpeI)-SpyCatcher-CD28-Zeta (FIG. 5A) and its nucleotide (SEQ ID NO: 5) and amino acid (SEQ ID NO: 6) sequences (FIG. 5B).

FIGS. 6A-6B are a series of schematic representations of the map of the construct: pELNS(SpeI)-SpyCatcher-GGS-CD28-Zeta (FIG. 6A) and its nucleotide (SEQ ID NO: 7) and amino acid (SEQ ID NO: 8) sequences (FIG. 6B).

FIGS. 7A-7B are a series of schematic representations of the map of the construct: pELNS(SpeI)-GFP-SpyTag-CD28-Zeta (FIG. 7A) and its nucleotide (SEQ ID NO: 1) and amino acid (SEQ ID NO: 2) sequences (FIG. 7B).

FIGS. 8A-8B are a series of schematic representations of the map of the construct: pELNS(SpeI)-GFP-SpyTag-GGS-CD28-Zeta (FIG. 8A) and its nucleotide (SEQ ID NO: 3) and amino acid (SEQ ID NO: 4) sequences (FIG. 8B).

FIGS. 9A-9B are a series of schematic representations of the map of the construct: pELNS(SpeI)-GFP-SpyCatcher-CD28-Zeta (FIG. 9A) and its nucleotide (SEQ ID NO: 13) and amino acid (SEQ ID NO: 14) sequences (FIG. 9B).

FIGS. 10A-10B are a series of schematic representations of the map of the construct: pELNS(SpeI)-GFP-SpyCatcher-GGS-CD28-Zeta (FIG. 10A) and its nucleotide (SEQ ID NO: 15) and amino acid (SEQ ID NO: 16) sequences (FIG. 10B).

FIG. 15A: SpyCatcher expressing T cells secrete IFNγ in response to plate bound A24-Protein G-SpyTag. SpyTag expressing T cells do not secrete IFNγ in response to plate bound L17-Protein Z-SpyCatcher. FIG. 15B: SpyCatcher expressing T cells secrete IFNγ in response to a broad range of A24-Protein G-SpyTag plate coating concentrations.

FIGS. 16A-16B are a series of graphs depicting the labeling of SpyCatcher T cells with Protein G-SpyTag and Biotin-Herceptin. Staining of cells was determined by flow cytometric analysis gating on live cells.

FIG. 17 is a series of graphs showing that pre-targeting Her2+ tumor cells with Herceptin-SpyTag leads to lysis by SpyCatcher T cells.

FIG. 18A: Specific lysis (%) 17 hours post T cell addition. FIG. 18B: Specific lysis (%) over the course of 4 days post T cell addition.

FIG. 19 is a series of graphs illustrating the combined arming and targeting with Herceptin-SpyTag.

DETAILED DESCRIPTION

Figure 1A:
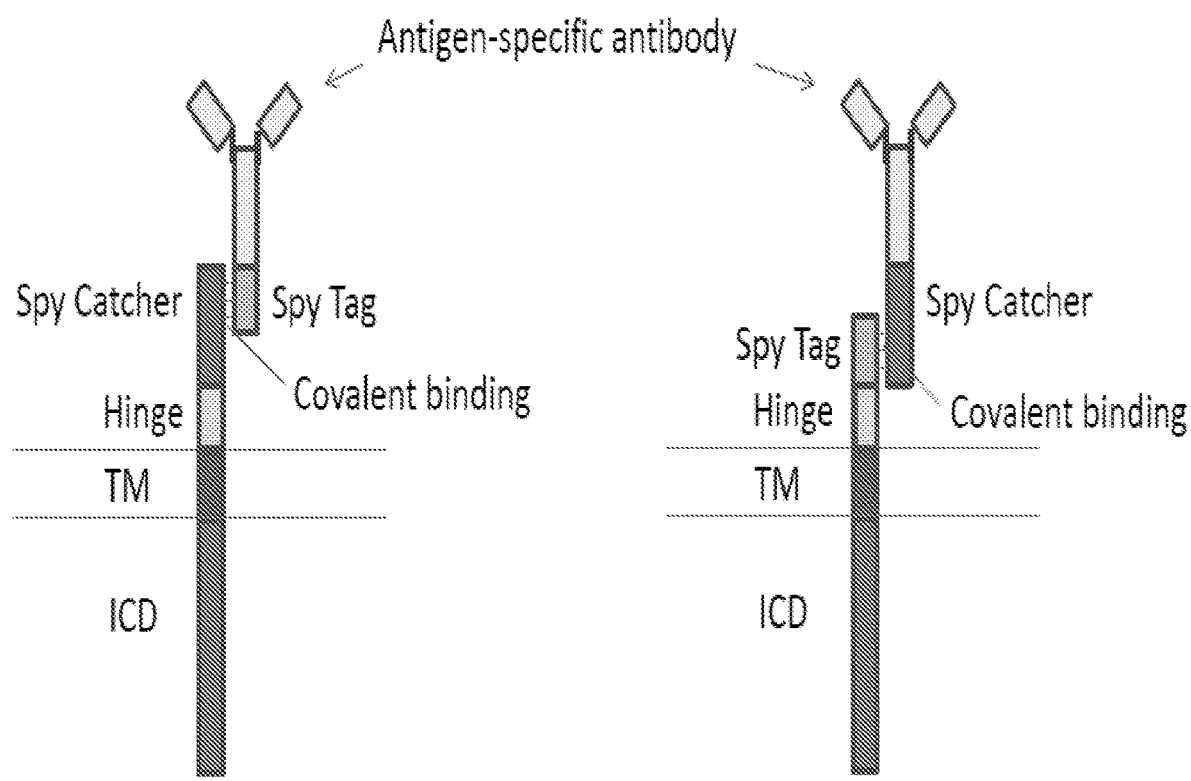
FIGS. 1A-1B are a series of schematic representations of the SpyCatcher and SpyTag constructs.
Figure 1B:
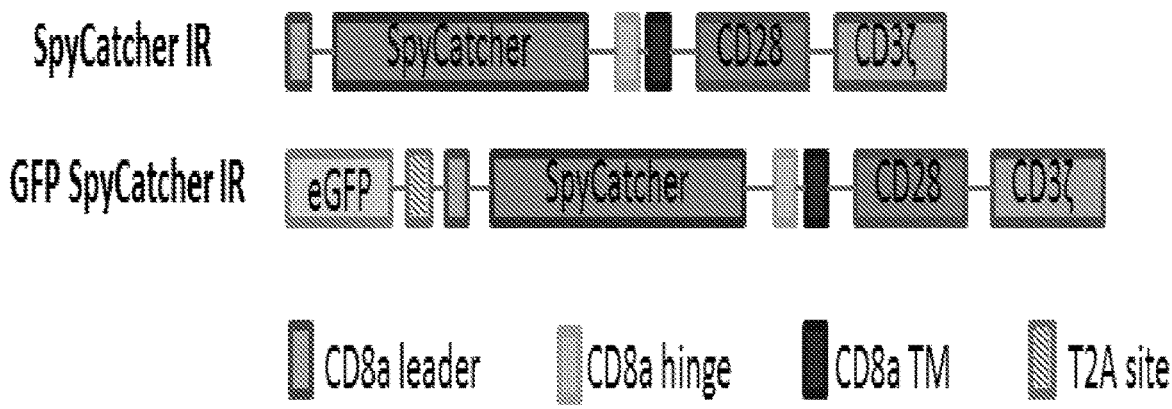
Figure 3A:
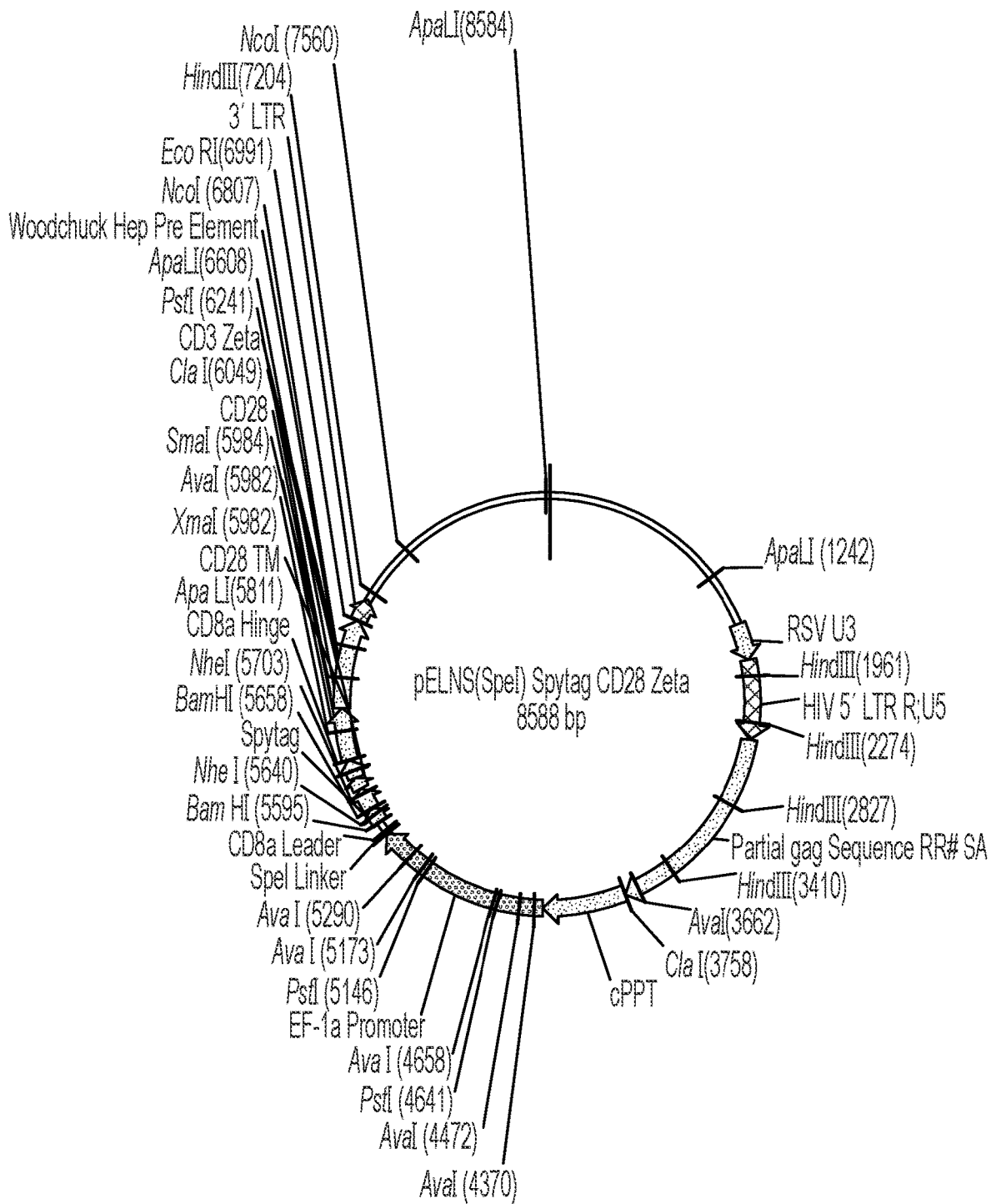
Figure 4A:
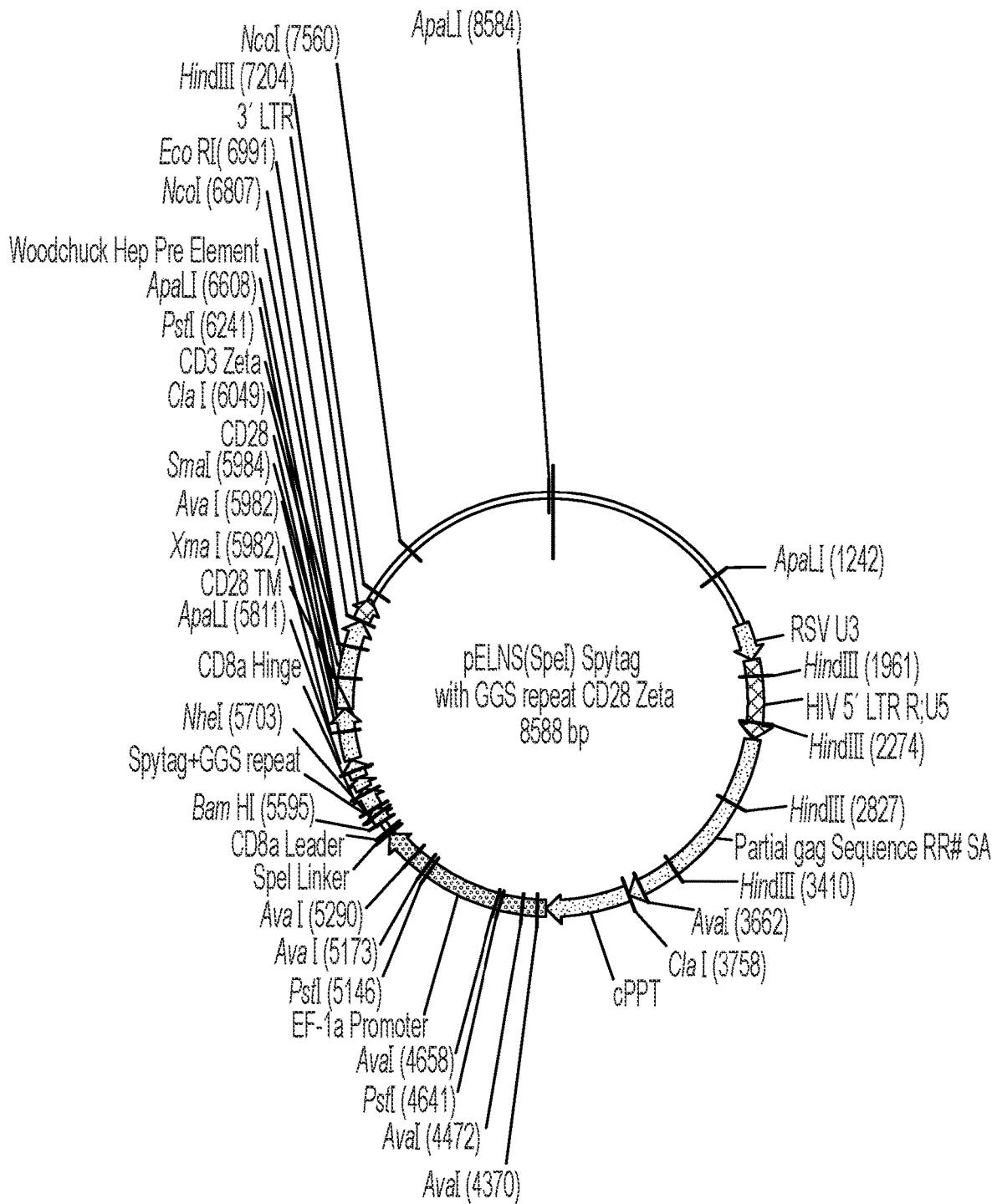
Figure 5A:
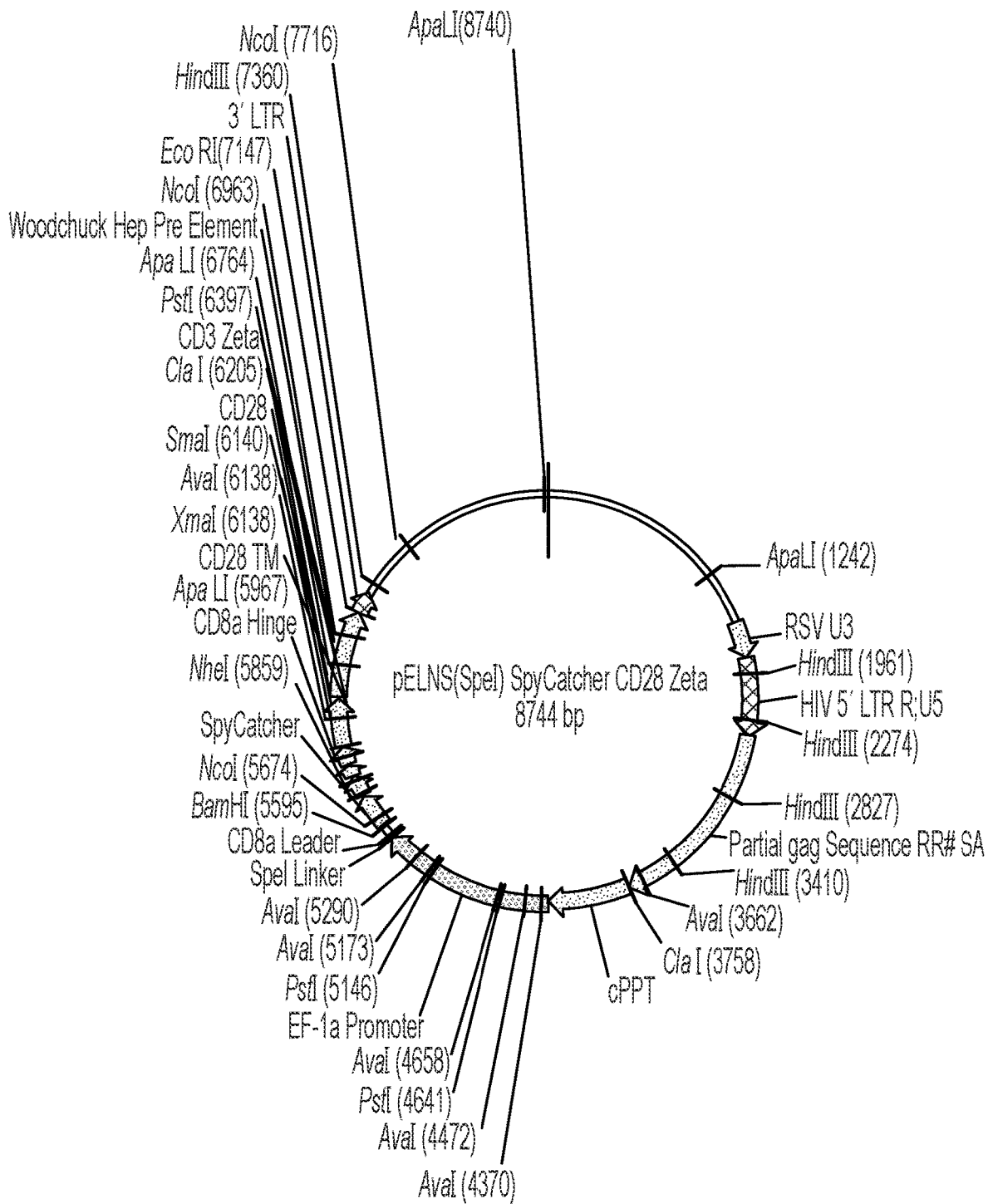
Figure 6A:
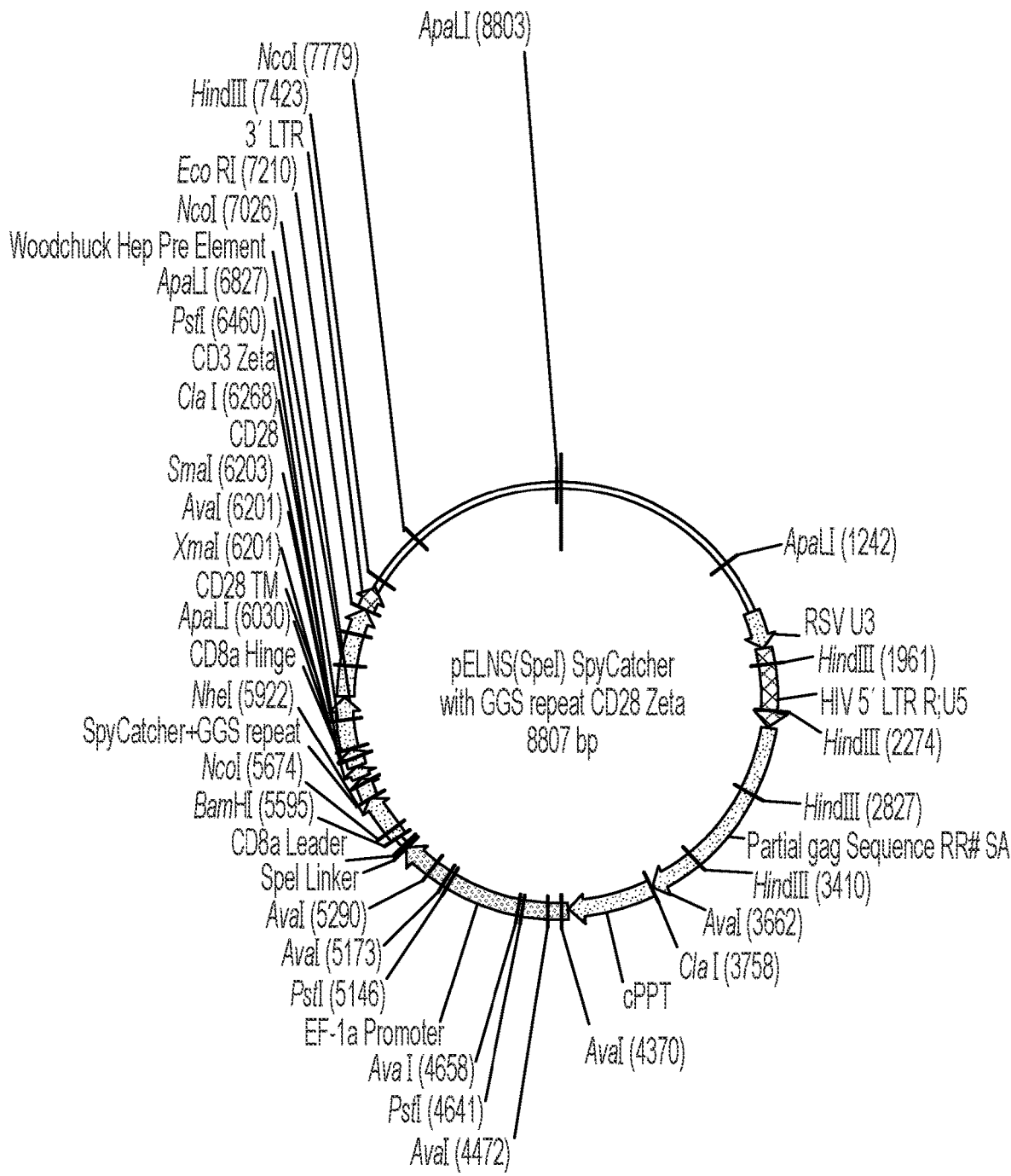
Figure 7A:
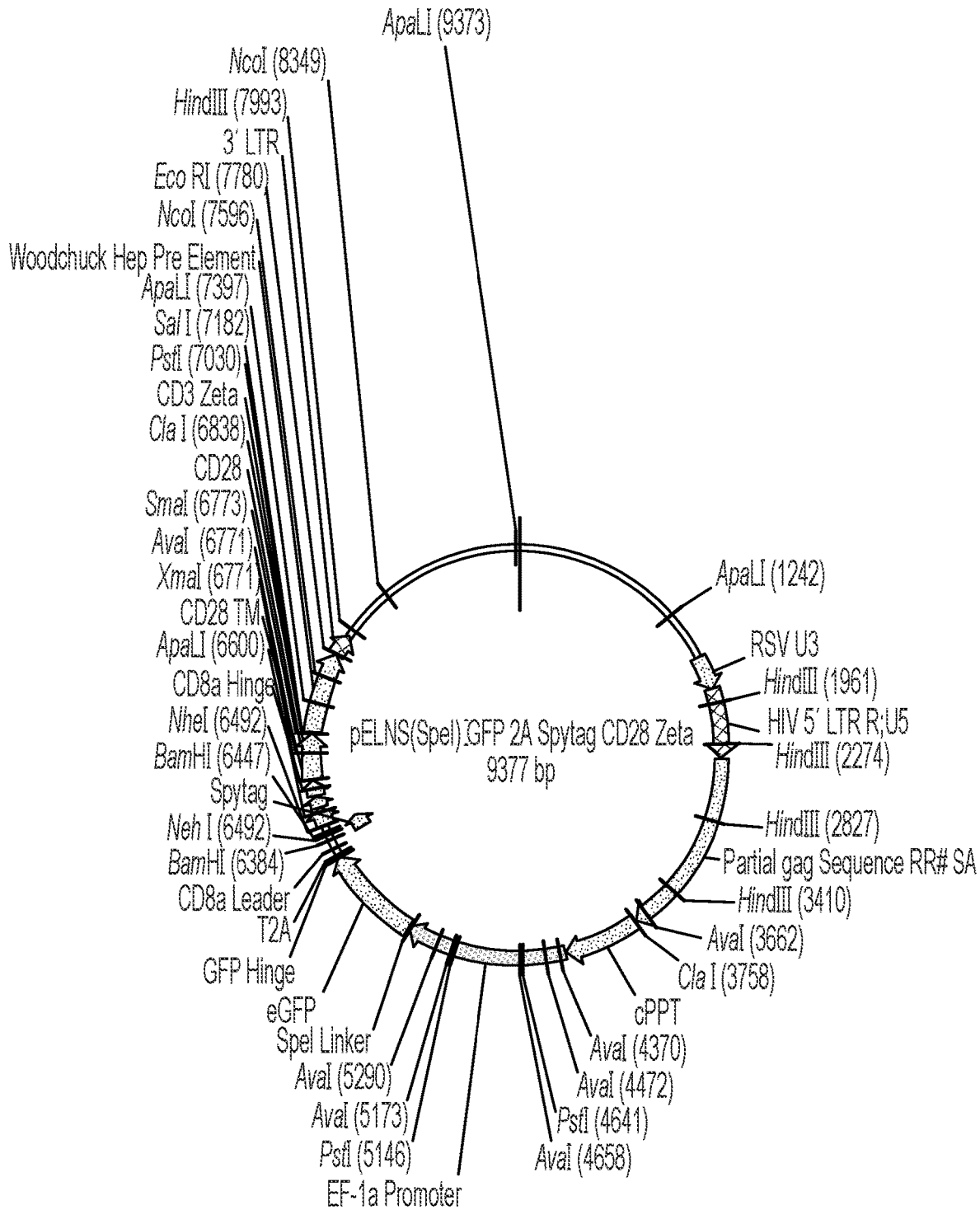
Figure 8A:
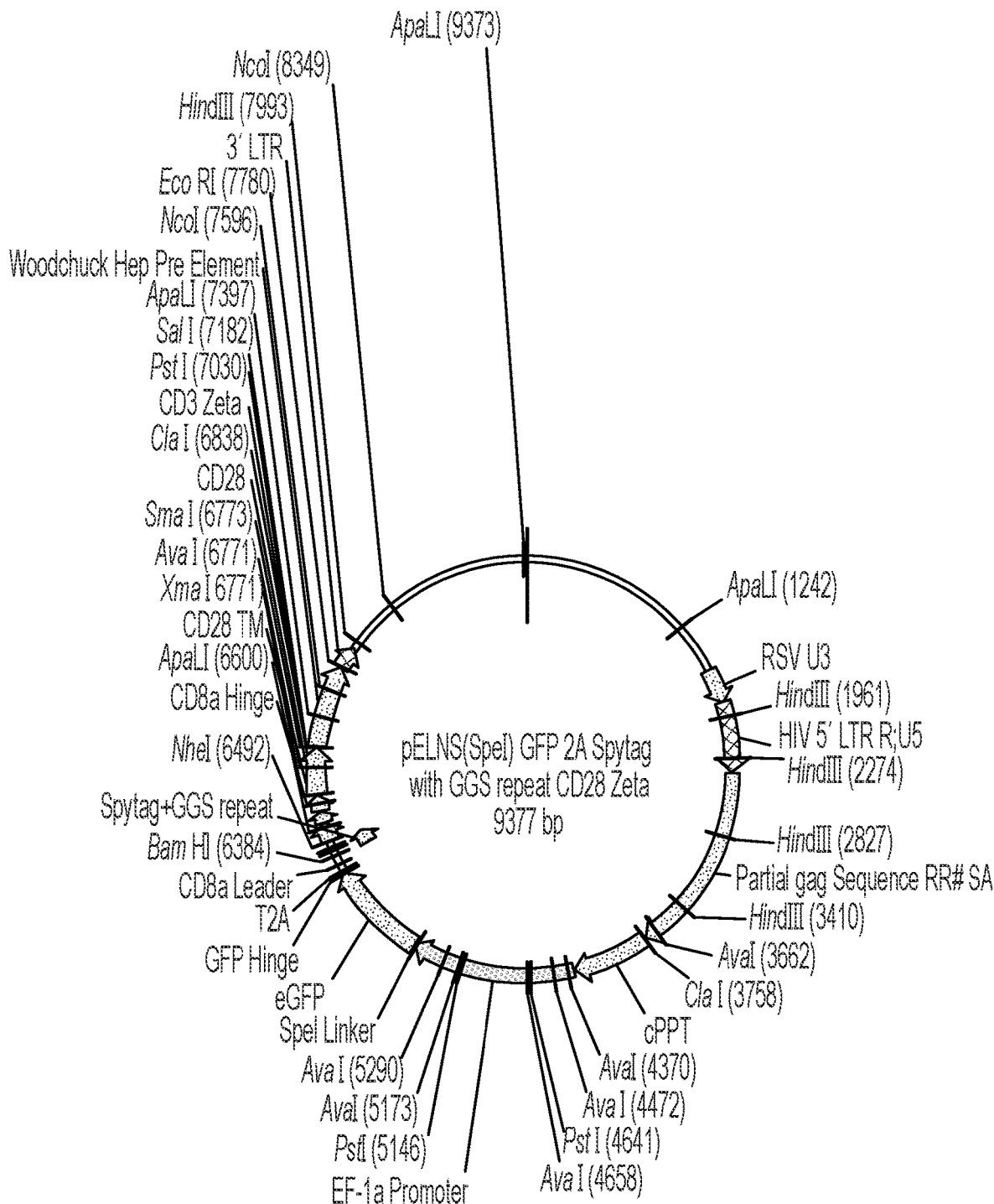
Figure 9A:
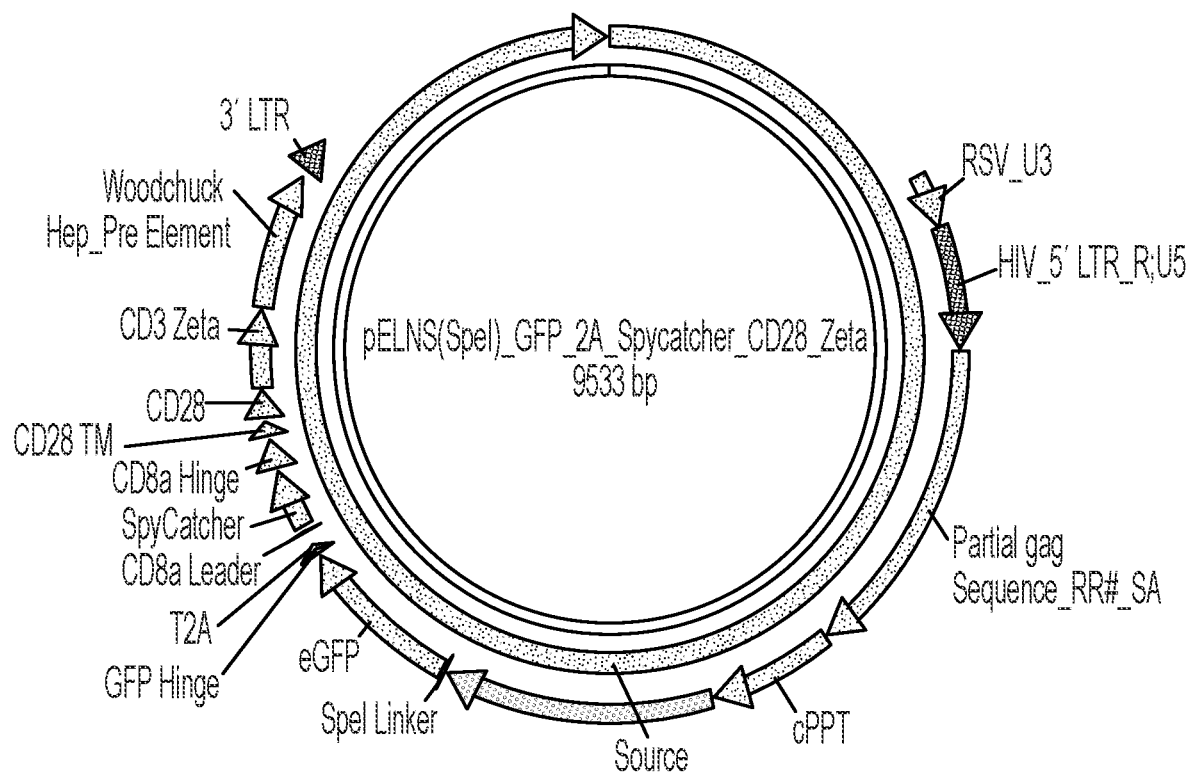
Figure 10A:
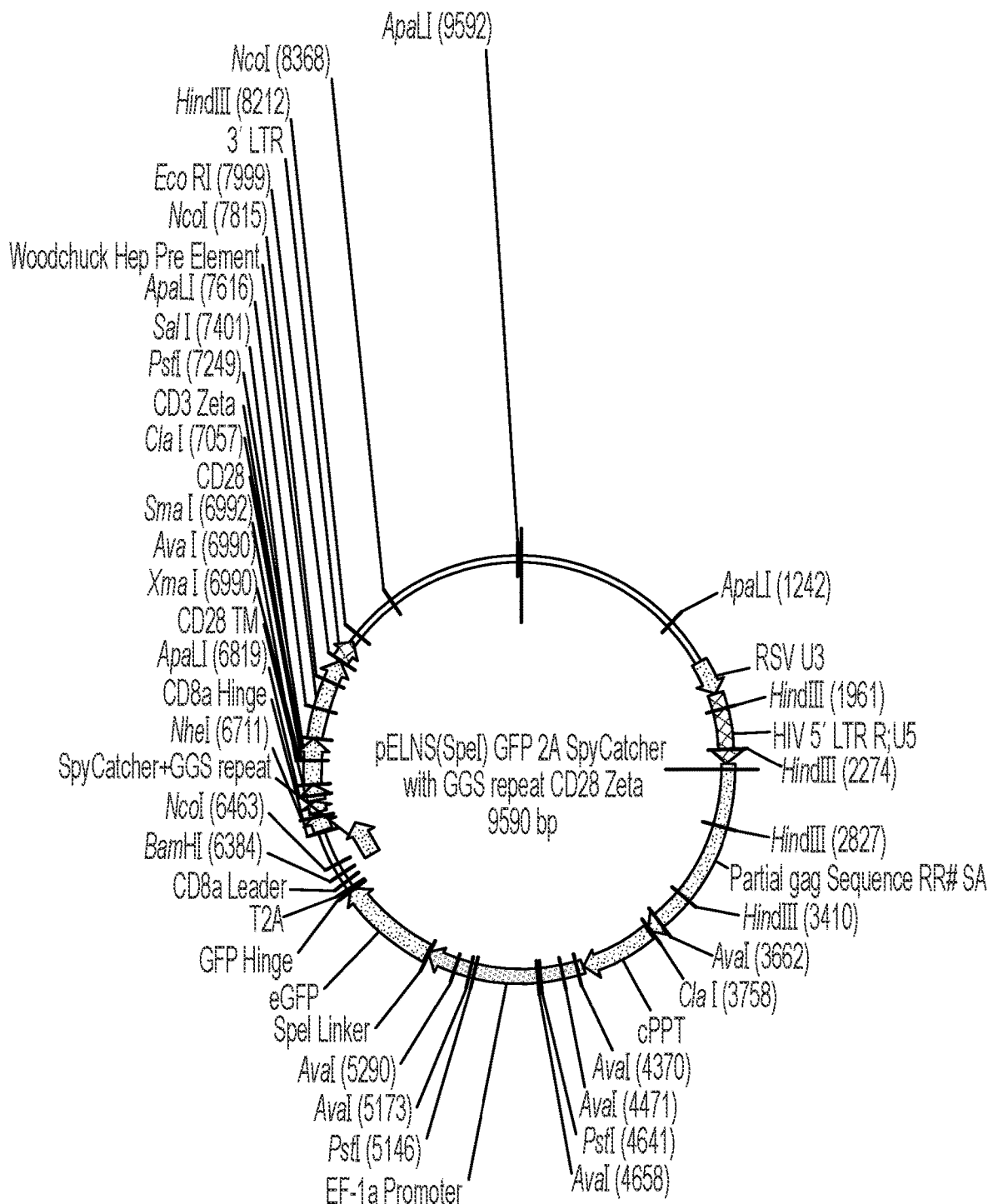

The invention relates to compositions and methods for adoptive T cell therapy useful for treating a variety of disorders including cancer, infections, and autoimmune disorders. The present invention relates to a strategy for adoptive cell transfer of T cells modified to express universal immune receptors referred herein as SpyTag and SpyCatcher universal immune receptors. The receptors of the invention are molecules that combine specificity for a desired antigen with a T cell receptor-activating intracellular domain to generate a chimeric protein that exhibits a specific immune activity. In one embodiment, the SpyTag and SpyCatcher universal immune receptors of the invention comprises an extracellular label binding domain, a transmembrane domain, and a cytoplasmic domain or otherwise an intracellular domain.

The present invention provides a universal immune receptor strategy through the incorporation of short nucleotide sequences into immune receptor constructs containing intracellular signaling components for T cell activation, a transmembrane region, and a extracellular hinge region onto which a peptide tag is fused. In one embodiment, a T cell is engineered to express SpyCatcher on its surface which can be bound by any molecule that incorporates a SpyTag moiety. In another embodiment, a T cell is engineered to express SpyTag immune receptor on its surface which can be bound by any molecule that incorporates a SpyCatcher moiety. Molecules that can be bound include but are not limited to those that may redirect the T cell against a surface antigen (e.g. antibody, scFv, receptor, ligand, aptamer, etc.) or labelling agents for T cell tracking in vivo. In addition, the reciprocal tag on the redirecting molecule (e.g. antibody) may be labeled by binding, such as through conjugation, fusion, or ligation, with a labelling agent and utilized as an antigen specific labelling agent used for diagnostics, to determine patient eligibility for a clinical trial, to determine time of maximal binding to antigen in target tissue (without residual agent in healthy tissues), and as a means of monitoring response to therapy.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation", as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is mistakenly recognized by the immune system as being foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD3, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of the tumor antigen is intended to indicate an abnormal level of expression of the tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The terms "SpyTag" and "SpyCatcher" refer to a convenient protein coupling tool that overcomes the generally weak protein-protein interaction (with "Spy" referring to the bacterium *Streptococcus pyogenes*). The SpyTag/SpyCatcher system is ideal for binding, labeling or immobilizing proteins as it creates irreversible peptide ligations. SpyTag is a genetically encoded peptide that forms a spontaneous amide bond upon binding its genetically encoded partner SpyCatcher. SpyTag reacts with SpyCatcher under a wide range of conditions and the after reaction the product is extremely stable (Zachari et al., 2012, PNAS vol. 109:12, pp. 690-69'7)

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an WIC Class I molecule loaded with a peptide, an anti-CD3 antibody, a superagonist anti-CD28 antibody, and a superagonist anti-CD2 antibody.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Current gene-engineered cellular therapy is restricted in antigen specificity, patient accessibility, and tumor or cell type. An alternative to creating a CAR, which has a fixed antigen specificity, is to create a universal T cell receptor that allows the specificity of the T cell receptor to be changed on demand. This is achieved by engineering T cells that express a unique peptide or protein tag, which can be labeled post-translationally with a complementary binding partner that is fused or attached to a targeting ligand (e.g. antibody, antibody binding domain, protein scaffold, aptamer, receptor, etc.), imaging agent, hapten, enzyme, etc. The benefits of creating a single engineered universal T cell that can subsequently be labeled with any targeting ligand includes, but is not limited to, the ability to create large panels of T cells very rapidly and easily, prepare individual T cells with multiple specificities, and change T cell specificity over time.

The present invention relates to an innovative technological strategy that incorporates TCR and co-stimulatory signals and allows single transfected T-cells to have near infinite antigen specificities. For this purpose, T cells have been equipped with a universal immune receptor redirected against any molecule that incorporates the complementary SpyTag or SpyCatcher moiety. The SpyTag or SpyCatcher moiety can be attached or fused to any antigen-specific molecules including; monoclonal antibodies, scFvs or other tumor specific ligands.

SpyCatcher and SpyTag represent a unique binding pair that form irreversible covalent bonds with each other. The SpyCatcher/Tag system is based on the immunoglobulin-like collagen adhesion domain (CnaB2) of *Streptococcus pyogenes*. Specifically, CnaB2 was recently split into to two complementary fragments, such that the first fragment (SpyCatcher) is able to rapidly bind and form a covalent linkage with the second fragment (SpyTag). The irreversible binding provided by this system, or similar systems capable of forming an intermolecular covalent linkage, can improve the stability of the interaction between the universal T cell receptor and its binding partner.

The present invention provides compositions and methods for treating diseases or disorders associated with expression of an antigen, including but not limited to viral antigens, tumor antigens, self-antigens, and the like. In one embodiment, the invention provides compositions and methods for treating cancer, as well as other diseases. The cancer may be a hematological malignancy, a solid tumor, a primary or a metastasizing tumor. Other diseases treatable using the compositions and methods of the invention include viral, bacterial and parasitic infections as well as autoimmune diseases.

In one embodiment, the invention provides a cell (e.g., T cell) engineered to express on its surface a universal immune receptor being a SpyCatcher or SpyTag which can be bound by any molecule that incorporates a SpyTag or SpyCatcher moiety, respectively. In one embodiment, the invention provides a method of treating a mammal in need thereof. The method comprises administering to the mammal an effective amount of the engineered cell as described herein. In one embodiment, the SpyCatcher or SpyTag is fused to an extra cellular hinge region, a transmembrane domain and an intracellular T cell signaling domain. Preferably, the SpyCatcher or SpyTag comprises a covalent binding to a reciprocal tag (i.e. a SpyTag or a SpyCatcher moiety, respectively) that is bound to a molecule. The molecule can be, but is not limited to, an antigen-specific antibody, an imaging/labeling agent, an aptamer or a receptor.

Non-limiting examples of labeling agent include myc-tag, FLAG-tag, His-tag, HA-tag, fluorescent proteins (e.g. green fluorescent protein (GFP)), fluorophores (e.g. tetramethyl-rhodamine (TRITC), fluorescein isothiocyanate (FITC)), dinitrophenol, peridinin chlorophyll protein complex, green fluorescent protein, phycoerythrin (PE), histidine, biotin, streptavidin, avidin, horse radish peroxidase, palmitoylation, nitrosylation, alkalanine phosphatase, glucose oxidase, Glutathione S-transferase (GST), maltose binding protein, radioisotopes, and any types of compounds used for radioisotope labeling including 1,4,7,10-tetraazacyclododecane-1,4,7,10-tetraacetic acid (also known as DOTA), diethylene triamine pentaacetic acid (DTPA), and 1,4,7-triazacyclononane-1,4,7-triacetic acid (NOTA). The invention further encompasses the use of known protein-protein interactions, complementary oligonucleotides, and receptor-ligand interactions.

In some embodiments, the present invention is directed to a retroviral or lentiviral vector encoding a SpyCatcher or a SpyTag that is stably integrated into a T cell and stably expressed therein. In other embodiments, the present invention is directed to an RNA or DNA encoding SpyCatcher or a SpyTag that is transfected into a T cell and transiently expressed therein.

The universal immune receptor platform of the invention (SpyCatcher or SpyTag) represents a universal approach for the targeting of gene-modified T cells to diverse and multiple antigens via interaction with a reciprocal tag (SpyTag or a SpyCatcher moiety, respectively) having antigen-binding molecules, either simultaneously or sequentially. The platform of the invention is applicable with virtually any molecule including but not limited to ligands, protein scaffolds, peptides, receptors, labeling agents, oligonucleotides, aptamers, antibodies, scFvs and/or single chain TCRs. The universal immune receptors the invention represent a new platform for the rapid screening and generation of redirected T cells with function against virtually any antigen for which a specific targeting agent exists, and thus holds potential for widespread application.

Compositions

The present invention provides a type of universal immune receptor comprising an extracellular and intracellular domain. The extracellular domain comprises a unique binding element otherwise referred to as an extracellular binding domain. In some embodiments, the extracellular domain also comprises a hinge region. The intracellular domain or otherwise the cytoplasmic domain comprises a costimulatory signaling region and a zeta chain portion. The costimulatory signaling region refers to a portion of the universal immune receptor comprising the intracellular domain of a costimulatory molecule. Costimulatory molecules are cell surface molecules other than antigens receptors or their ligands that are required for an efficient response of lymphocytes to antigen.

Between the extracellular domain and the transmembrane domain of the universal immune receptor, or between the cytoplasmic domain and the transmembrane domain of the universal immune receptor, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

The present invention includes retroviral and lentiviral vector constructs capable of expressing a universal immune receptor that can be directly transduced into a cell. The present invention also includes an RNA or DNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the gene to be expressed, and a polyA tail, typically 50-2000 bases in length. RNA so produced can efficiently transfect different kinds of cells. In one embodiment, the template includes sequences for the universal immune receptor.

Polynucleotide vectors can be prepared that encode the universal immune receptor. Cell lines can then be engineered to express the universal immune receptor, and cells expressing the universal immune receptor can be isolated and used in the methods disclosed herein.

The cells expressing the universal immune receptor may be formulated for administration to a subject using techniques known to the skilled artisan. Formulations of the cells expressing the universal immune receptor may include pharmaceutically acceptable excipient(s). Excipients included in the formulations will have different purposes depending, for example, on the nature of the label, the cell composition, and the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubricating agents.

Preferably, the universal immune receptor comprises an extracellular domain, a transmembrane domain and a cytoplasmic domain. The extracellular domain and transmembrane domain can be derived from any desired source of such domains.

Extracellular Label Binding Domain

The extracellular domain of the universal immune receptor of the present invention comprises SpyTag or SpyCatcher. In one embodiment, SpyTag or SpyCatcher is associated with its reciprocal tag, i.e. SpyCatcher or SpyTag, respectively, which can be bound to any molecule of interest. In one embodiment, the extracellular domain or reciprocal tag may consist of an Ig heavy chain which may in turn be covalently associated with Ig light chain by virtue of the presence of CH1 and hinge regions, or may become covalently associated with other Ig heavy/light chain complexes by virtue of the presence of hinge, CH2 and CH3 domains. In the latter case, the heavy/light chain complex that becomes joined to the chimeric construct may constitute an antibody with a specificity distinct from the antibody specificity of the chimeric construct. Depending on the function of the antibody, the desired structure and the signal transduction, the entire chain may be used or a truncated chain may be used, where all or a part of the CH1, CH2, or CH3 domains may be removed or all or part of the hinge region may be removed.

The present invention is based upon a universal strategy of adoptive T cell therapy using the SpyCatcher or SpyTag system that binds any molecule that comprises the reciprocal tag: SpyTag or SpyCatcher, respectively. Any molecule capable of being bound, such as fused, conjugated, ligated or labeled, with a SpyTag or a SpyCatcher moiety is encompassed in the present invention. For example, the molecule of the present invention encompasses a protein (an antibody, antibody fragment, scFv, protein scaffold, a receptor, a ligand), peptide, oligonucleotides, an imaging/labeling agent and the like. Examples of other types of labels useful in the present invention include myc-tag, FLAG-tag, His-tag, HA-tag, fluorescent protein (e.g. green fluorescent protein (GFP)), fluorophore (e.g. Tetramethylrhodamine (TRITC), fluorescein isothiocyanate (FITC)), dinitrophenol, peridinin chlorophyll protein complex, green fluorescent protein, biotin, phycoerythrin (PE), histidine, streptavidin, avidin, horse radish peroxidase, palmitoylation, nitrosylation, alkalanine phosphatase, glucose oxidase, Glutathione S-transferase (GST), maltose binding protein, fluorescein and any types of fluorescent materials including quantum dot nanocrystals, radioisotopes, and any types of compounds used for radioisotope labeling including, 1,4,7,10-tetraaza-cyclododecane-1,4,7,10-tetraacetic acid (DOTA), diethylene triamine pentaacetic acid (DTPA), and 1,4,7-triazacyclononane-1,4,7-triacetic acid (NOTA).

In one embodiment, the universal immune receptor of the invention comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen moiety domain in the universal immune receptor of the invention include those associated with viral, bacterial and parasitic infections, autoimmune disease and cancer cells.

In one embodiment, a retroviral or lentiviral vector comprises a universal immune receptor designed to express a SpyTag or SpyCatcher on the T cell surface, which can be bound to any molecule that incorporates a SpyTag or a SpyCatcher moiety, respectively. In one embodiment, the molecule comprises a target- or antigen-specific binding element. The binding domain may be chosen to recognize a target, ligand, or antigen that acts as a cell surface marker on target cells associated with a particular disease or disorder. In some embodiments, the antigen can be associated with specific hyperproliferative disorders. In certain aspects, the hyperproliferative disorder antigens of the present invention are derived from cancers including, but not limited to, primary or metastatic melanoma, mesothelioma, thymoma, lymphoma, sarcoma, lung cancer, liver cancer, non-Hodgkin's lymphoma, Hodgkin's lymphoma, leukemias, uterine cancer, cervical cancer, bladder cancer, kidney cancer and adenocarcinomas such as breast cancer, prostate cancer, ovarian cancer, pancreatic cancer, and the like. In general, the cancer may be any type of cancer as long as the cancerous tumor has a cell surface antigen that may be recognized by the present SpyTag/SpyCatcher universal immune receptor system.

The present invention is not limited to universal immune receptors directed to tumor antigens. Rather any target, ligand, or antigen associated with a disease or disorder may be targeted by the universal immune receptor of the invention. For example, in one embodiment, the universal immune receptor of the invention is targeted to a viral antigen. In another embodiment, the universal immune receptor of the invention is targeted to a self-antigen. Self-antigens are antigens normally tolerated by a healthy subject, but induce an adaptive immune response in autoimmune disorders. For example, epidermal cadherin is a self-antigen that induces an autoimmune response in pemphigus vulgaris. Other non-limiting self-antigens (listed with their associated autoimmune disorder) which are useful to be targeted by the composition of the invention, include pancreatic (3-cell antigen (insulin-dependent diabetes mellitus), acetylcholine receptor (Myasthenia gravis), thyroid-stimulating hormone receptor (Graves' disease), insulin receptor (hypoglycemia), glycoprotein IIb/IIIa (immune thrombocytopenic purpura), Rh blood group antigens (autoimmune hemolytic anemia), rheumatoid factor IgG complexes (rheumatoid arthritis), and myelin basic protein (experimental autoimmune encephalomyelitis, multiple sclerosis).

Transmembrane Domain

With respect to the transmembrane domain, the SpyTag/SpyCatcher universal immune receptor of the present invention can be designed to comprise a transmembrane domain that is fused to the extracellular domain that is bound to the SpyTag/SpyCatcher system. In one embodiment, the transmembrane domain that naturally is associated with another the domain in the universal immune receptor is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the universal immune receptor. A glycine-serine doublet provides a particularly suitable linker.

Cytoplasmic Domain

The cytoplasmic domain or otherwise the intracellular signaling domain of the SpyTag/SpyCatcher universal immune receptor of the invention is responsible for activation of at least one of the normal effector functions of the immune cell in which the universal immune receptor has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein that transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the universal immune receptor of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the universal immune receptor of the invention comprises a cytoplasmic signaling sequence derived from CD3 zeta.

In a preferred embodiment, the cytoplasmic domain of the universal immune receptor can be designed to comprise the CD3-zeta signaling domain by itself or combined with any other desired cytoplasmic domain(s) useful in the context of the universal immune receptor of the invention. For example, the cytoplasmic domain of the universal immune receptor can comprise a CD3 zeta chain portion and a costimulatory signaling region. The costimulatory signaling region refers to a portion of the universal immune receptor comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD3, CD7, LIGHT, NKG2C, B7-H3, and a ligand that specifically binds with CD83, and the like. Thus, while the invention is exemplified primarily with CD28 and 4-1BB as the co-stimulatory signaling element, other costimulatory elements are within the scope of the invention.

The cytoplasmic signaling sequences within the cytoplasmic signaling portion of the universal immune receptor of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain is designed to comprise the signaling domain of CD3-zeta. In another embodiment, the cytoplasmic domain is designed to comprise any combination of CD3-zeta, CD28, 4-1BB, and the like.

In one embodiment, the SpyTag/SpyCatcher universal immune receptor may substantially lack a cytoplasmic domain or the cytoplasmic domain may substantially lack signaling capacity. In such an embodiment, the SpyTag/SpyCatcher universal immune receptor may serve as an anchoring molecule to attach tagged proteins, including but not limited to antibodies, cytokines and imaging moieties, to the T cell surface.

Labeling of Molecules

The present invention encompasses a SpyTag/SpyCatcher universal immune receptor directed to a labeled molecule with a reciprocal SpyTag/SpyCatcher moiety. The molecule of interest can be labeled by any method known in the art. For example, in one embodiment, a composition comprising the labeled molecule is bound to the universal immune receptor. The molecule may be, for example, any molecule comprising an antigen binding domain or fragment thereof, such as an antibody, an antibody fragment, and a scFv, a peptide, a protein scaffold, a nucleic acid, aptamer, ribozyme, small molecule, and the like. In some aspects, the molecule of interest lacks a label but still interacts with the universal immune receptor. For example, in one embodiment, a composition comprising the molecule of interest lacks a label, while a second composition comprising the universal immune receptor contains the label.

Any known set of molecules may be used to target the SpyTag/SpyCatcher universal immune receptor to an antigen of interest. Non-limiting examples of molecules include any molecule comprising an antigen binding domain or fragment thereof, such as an antibody, an antibody fragment, and a scFv, a peptide, a protein scaffold, an oligonucleotide, a small molecule, and a ligand. Well-known examples of labels that can be bound, such as fused, conjugated, or ligated, or attached to the molecule include myc-tag, FLAG-tag, His-tag, HA-tag, fluorescent protein (e.g. green fluorescent protein (GFP)), a fluorophore (e.g. tetramethylrhodamine (TRITC), fluorescein isothiocyanate (FITC)), dinitrophenol, peridinin chlorophyll protein complex, green fluorescent protein, biotin, phycoerythrin (PE), histidine, streptavidin, avidin, horse radish peroxidase, palmitoylation, nitrosylation, alkalanine phosphatase, glucose oxidase, Glutathione S-transferase (GST), maltose binding protein, any types of fluorescent materials including quantum dot nanocrystals, radioisotopes, and any types of compounds used for radioisotope labeling including, 1,4,7,10-tetraazacyclododecane-1,4,7,10-tetraacetic acid (DOTA), diethylene triamine pentaacetic acid (DTPA), and 1,4,7-triazacyclononane-1,4,7-triacetic acid (NOTA).

Labeling of the molecules with any of such labels may be performed directly or indirectly. The label may be conjugated to the molecule using techniques such as chemical coupling and chemical cross-linkers. Alternatively, polynucleotide vectors can be prepared that encode the labeled molecules as fusion proteins. Cell lines can then be engineered to express the labeled molecule, and the labeled molecule can be isolated from culture media, purified and used in the methods disclosed herein. A labeled amino acid, labeled peptide, labeled protein, or molecular reporter may also be ligated to the molecule via expressed protein ligation (e.g. using sortase, inteins, etc.).

The labeled molecule may be formulated for administration to a subject using techniques known to the skilled artisan. Formulations of the labeled molecule may include pharmaceutically acceptable excipient(s). Excipients included in the formulations will have different purposes depending, for example, on the nature of the label, the antigen binding composition, and the mode of administration. Examples of generally used excipients include, without limitation: saline, buffered saline, dextrose, water-for-infection, glycerol, ethanol, and combinations thereof, stabilizing agents, solubilizing agents and surfactants, buffers and preservatives, tonicity agents, bulking agents, and lubricating agents.

In another embodiment, the universal immune receptor comprises an extracellular domain that binds to an unlabeled intermediate, which in turn binds the molecule or labeled molecule.

Vectors

The present invention encompasses a DNA construct comprising the sequence of a SpyTag/SpyCatcher universal immune receptor, wherein the sequence comprises the nucleic acid sequence of an extracellular domain operably linked to the nucleic acid sequence of an intracellular domain. In one embodiment, the extracellular domain comprises a SpyTag domain. In another embodiment, the extracellular domain comprises a SpyCatcher domain. An exemplary intracellular domain that can be used in the universal immune receptor of the invention includes but is not limited to the intracellular domain of CD3-zeta, CD28, 4-1BB, and the like. In some instances, the universal immune receptor can comprise any combination of CD3-zeta, CD28, 4-1BB, and the like.

In one embodiment, the universal immune receptor of the invention comprises a SpyCatcher or SpyTag domain, a human CD8 alpha hinge and transmembrane domain, and a CD28 and CD3-zeta signaling domains.

The nucleic acid sequences coding for the desired molecules can be obtained using recombinant methods known in the art, using standard techniques. Alternatively, the gene of interest can be produced synthetically.

The present invention also provides vectors in which a DNA of the present invention is inserted (e.g. DNA encoding a SpyTag or a SpyCatcher domain). Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding universal immune receptors is typically achieved by operably linking a nucleic acid encoding the universal immune receptor (e.g. SpyTag/SpyCatcher) polypeptide or portions thereof to a promoter, and incorporating the construct into an expression vector. The vectors can be suitable for replication and integration in eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a universal immune receptor polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

RNA Transfection

In one embodiment, the genetically modified T cells of the invention are modified through the introduction of RNA. In one embodiment, an in vitro transcribed SpyTag or SpyCatcher universal immune receptor RNA can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is the universal immune receptor of the present invention. For example, the template for the RNA of the universal immune receptor comprises an extracellular domain comprising a label binding domain; a transmembrane domain comprising the hinge and transmembrane domain of CD8a; and a cytoplasmic domain comprises the signaling domain of CD3-zeta.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA that is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100 T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as *E. coli* polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Genetically Modified T Cells

In some embodiments, the SpyTag or SpyCatcher universal immune receptor sequences are delivered into cells using a retroviral or lentiviral vector. Universal immune receptor-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In other embodiments, the SpyTag or SpyCatcher universal immune receptor sequences are delivered into cells using in vitro transcribed mRNA. In vitro transcribed mRNA universal immune receptor can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell. In some embodiments, the modified T cells are labeled and can be traced in vivo once transferred to a subject.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the universal immune receptor mRNAs with different structures and combination of their domains. For example, varying of different intracellular effector/costimulator domains on multiple universal immune receptors in the same cell allows determination of the structure of the receptor combinations which assess the highest level of cytotoxicity against multi-antigenic targets—after the universal immune receptors are associated with a reciprocal tag that is attached to an antigen-binding element- and at the same time lowest cytotoxicity toward normal cells.

One advantage of RNA transfection methods of the invention is that RNA transfection is essentially transient and a vector-free: An RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. Preferably, it is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct can be delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of T Cells

Prior to expansion and genetic modification of the T cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL gradient or by counterflow centrifugal elutriation. A specific subpopulation of T cells, such as $CD3^+$, $CD28^+$, $CD4^+$, $CD8^+$, $CD45RA^+$, and $CD45RO^+$T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immune-compromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5 \times 10^6$/ml. In other embodiments, the concentration used can be from about $1 \times 10^5$/ml to $1 \times 10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

Whether prior to or after genetic modification of the T cells to express a desirable universal immune receptor, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4$^+$) that is greater than the cytotoxic or suppressor T cell population ($T_C$, CD8$^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

The present invention encompasses a cell (e.g., T cell) modified to express a universal immune receptor that combines a SpyTag or SpyCatcher domain with an intracellular domain of a T cell receptor. In some instances, the universal immune receptor further comprises an intracellular domain of one or more co-stimulatory molecule. Therefore, in some instances, the modified T cell can elicit a universal immune receptor-mediated T-cell response.

The invention provides the use of a universal immune receptor to redirect the specificity of a primary T cell to any given molecule that incorporates a SpyTag or SpyCatcher moiety. Thus, the present invention also provides a method for stimulating a T cell-mediated immune response to a target cell population or tissue in a mammal comprising the steps of tagging/labeling the target antigen (with a SpyTag or SpyCatcher moiety for instance) and administering to the mammal a T cell that expresses a universal immune receptor, wherein the universal immune receptor comprises a binding moiety that specifically interacts with the tagged/labeled target, an intracellular domain of a TCR (e.g., intracellular domain of human CD3zeta), and a costimulatory signaling region.

In one embodiment, tagging/labeling of the target molecule comprises administering to the mammal a composition which comprises a tagged and/or a labeled molecule. Administration of the T cell and the tagged/labeled molecule may occur in any order. For example, in one embodiment, the labeled molecule is administered to the mammal prior to administration of the T cell. In another embodiment, the T cell is administered to the mammal prior to administration of the tagged/labeled antigen. In another embodiment, the universal immune receptor may be bound to tagged/labeled molecule prior to administration of the T cell to the mammal.

The tagged/labeled molecule or compositions comprising the tagged/labeled molecule may be administered to a subject using modes and techniques known to the skilled artisan. Exemplary modes include, but are not limited to subcutaneously, intradermally, intratumorally, intranodally, intramedullary, intramuscularly, by intravenous (i. v.) injection, intra-arterial, intracardiac, intra-articular, intrasynovial, intracranial, intraspinal, intrathecal or intraperitoneally. In one embodiment, the labeled compositions are administered to a patient by intradermal or subcutaneous injection. In another embodiment, the labeled compositions of the present invention are preferably administered by i.v. injection. The tagged/labeled molecule or compositions comprising the tagged/labeled molecule may be injected directly into a tumor, lymph node, or site of infection. The tagged/labeled molecule or compositions comprising the tagged/labeled molecule are administered in an amount which is effective for tagging/labeling the target antigen and is effective for treating the patient. The particular amount administered to the subject will vary between wide limits, depending upon the location, source, identity, extent and severity of the disorder, the age and condition of the individual to be treated, etc.

In one embodiment, the present invention includes a type of cellular therapy where T cells are genetically modified to express a SpyTag or SpyCatcher universal immune receptor. The SpyTag or SpyCatcher is associated with its reciprocal tag: SpyCatcher or SpyTag, which is bound, such as fused, labeled, ligated or conjugated, to a molecule comprising an antigen-binding domain. The universal immune receptor system is then administered to a recipient in need thereof. In another embodiment, the SpyTag- or SpyCatcher-bound molecule is administered to the mammal prior to the genetically modified cell. In yet another embodiment, the universal immune receptor is bound to the SpyTag- or the SpyCatcher-bound molecule prior to administering the genetically modified cell to the mammal The administered cell is able to kill tumor cells in the recipient.

While the data disclosed herein specifically disclose lentiviral vectors encoding a SpyCatcher domain, along with human CD8a hinge and transmembrane domain, and human CD28 and CD3zeta signaling domains, the invention should be construed to include any number of variations for each of the components of the construct as described elsewhere herein.

The present invention also provides a method of simultaneously targeting a plurality of targets. For example, in one embodiment, a plurality of molecules are tagged/labeled, either directly or indirectly with SpyCatcher/SpyTag. For example, in one embodiment, a plurality of molecules are bound, such as labeled, conjugated, ligated or fused, with a SpyCatcher/SpyTag, specific for each of the plurality of molecules, is administered to the mammal. Administration of a genetically modified T cell expressing a universal immune receptor comprising the reciprocal tag (SpyTag/SpyCatcher) allows for the targeting of the modified T cells to each of the plurality of reciprocally tagged molecules. In one embodiment, the method comprises administering a plurality of SpyTag- or SpyCatcher-bound molecules to the mammal prior to administering the genetically modified cell to the mammal. In such an embodiment, the universal immune receptor may bind the plurality of SpyTag- or SpyCatcher-bound molecules. In another embodiment, the method comprises binding the universal immune receptor with a plurality of SpyTag- or SpyCatcher-bound molecules prior to administering the genetically modified cell to the mammal.

In another embodiment, a plurality of molecules are targeted by multi-specific T cells. For example, genetically modified T cells expressing a SpyCatcher/SpyTag universal immune receptor are bound with a plurality of molecules that are bound, such as labeled, conjugated, ligated or fused, with the reciprocal SpyCatcher/SpyTag, specific for each of the plurality of molecules. These multi-specific T cells are then administered to the mammal. Administration of genetically modified multi-specific T cells allows for the targeting of the modified T cells to each of the plurality of reciprocally tagged molecules.

The present invention also provides a method of sequential targeting of a plurality of targets. For example, in one embodiment, a first molecule is tagged/labeled, either directly or indirectly. For example, in one embodiment, a first SpyTag or SpyCatcher tagged molecule, specific for a first antigen, is administered to the mammal. In one embodiment, the method comprises administering a genetically modified T cell expressing a universal immune receptor comprising a complementary SpyTag or SpyCatcher binding domain binds the first tagged molecule, thereby targeting the T cell to the first antigen. In one embodiment, the method comprises tagging/labeling a second molecule, either directly or indirectly. For example, in one embodiment, a second tagged molecule (such as a second SpyTag or SpyCatcher-tagged molecule), specific for a second antigen, is administered to the mammal. Genetically modified T cells expressing the universal immune receptor comprising a SpyTag or SpyCatcher domain bind the second tagged molecule and is thus directed to the second antigen. In one embodiment, the method comprises sequentially administering a plurality of SpyTag- or SpyCatcher-bound molecules to the mammal prior to administering the genetically modified cell to the mammal. In another embodiment, the method comprises allowing sufficient time to elapse between administration of the first and second tagged molecules, to allow for clearance of cells expressing the first antigen prior to directing the T cell to the second antigen. In yet another embodiment, the method comprises sequentially binding the universal immune receptor with a plurality of SpyTag- or SpyCatcher-bound molecules prior to administering the genetically modified cell to the mammal. As would be understood by those skilled in the art, the method of the invention encompasses further iterations for the targeting of additional target antigens.

In one embodiment, the present invention provides a method of using a universal immune receptor to target a tagged antigen for treating cancer. Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the SpyTag or SpyCatcher universal immune receptors of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases). In one embodiment, the present invention provides a method of using the universal immune receptor to target an antigen associated with a virus, bacteria, parasite, or other infection in order to treat the infection.

In one embodiment, the present invention provides a method of using the SpyTag or SpyCatcher universal immune receptor to target a self-antigen to treat an autoimmune disorder. In one embodiment, the method comprises genetically modifying an immunosuppressive T regulatory cell to express a universal immune receptor comprising a SpyTag or SpyCatcher domain. In one embodiment comprises tagging a molecule comprising a self-antigen binding domain with a reciprocal tag (SpyCatcher or SpyTag, respectively) and administering a T regulatory cell modified to express a universal immune receptor comprising a SpyTag or SpyCatcher domain. In one embodiment, targeting of the T regulatory cell to the self-antigen reduces the autoimmune response directed to the self-antigen. For example, in one embodiment, activation of the genetically modified T regulatory cell via binding to the targeted self-antigen reduces cytolytic T cell proliferation. Non-limiting examples of autoimmune disorders treatable by way of the present invention includes multiple sclerosis, inflammatory bowel disease, Crohn's disease, ulcerative colitis, graft-versus-host disease, rheumatoid arthritis, psoriasis, dermatitis, autoimmune type I diabetes, systemic lupus erythematosus, Hashimoto's thyroiditis, myasthenia gravis, and the like. As it would be understood by the skilled artisan, the present invention is useful for treating any autoimmune disorder characterized by an autoimmune response against a self-antigen. The present invention encompasses treatment of autoimmune disorders where the self-antigen is currently known, and where the self-antigen is elucidated in the future.

However, the invention should not be construed to be limited to solely to the antigen targets and diseases disclosed herein. Rather, the invention should be construed to include any antigenic target that is associated with a disease where a universal immune receptor can be used to treat the disease.

The universal immune receptor-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a universal immune receptor to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a universal immune receptor disclosed herein. The universal immune receptor-modified cell can be administered to a mammalian recipient to provide a therapeutic benefit. The mammalian recipient may be a human and the universal immune receptor-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the universal immune receptor-modified T cells of the invention are used in the treatment of cancer. In certain embodiments, the cells of the invention are used in the treatment of patients at risk for developing cancer. Thus, the present invention provides methods for the treatment or prevention of cancer comprising administering to a subject in need thereof, a therapeutically effective amount of the universal immune receptor-modified T cells of the invention.

The SpyTag or SpyCatcher universal immune receptor-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludarabine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. Strategies for T cell dosing and scheduling have been discussed (Ertl et al, 2011, Cancer Res, 71:3175-81; Junghans, 2010, Journal of Translational Medicine, 8:55).

Screening

In one embodiment, the present invention provides a method for screening potential antigen binding compositions, including for example, antibodies, peptides, oligonucleotides, ribozymes, aptamers, and the like. According to one embodiment of the present invention, a T cell modified to express a universal immune receptor comprising a SpyTag or SpyCatcher binding domain is used to screen reciprocally tagged compositions (i.e tagged with a SpyCatcher or SpyTag moiety respectively) for the ability of the composition to bind to the target antigen. In one embodiment, the screening system of the invention is used for diagnostics, to determine patient eligibility on trial, to determine time of maximal binding to antigen in target tissue (without residual agent in healthy tissues), and as a means of monitoring response to therapy. In one embodiment, a cell based assay comprising the universal immune receptor-expressing modified T cell is used to screen compositions. In one embodiment, the assay comprises administering a tagged composition to the assay and detecting a detectable response induced by the T cell. For example, in one embodiment, the assay comprises detecting the activation of the T cell. In another embodiment, the assay comprises detecting the level of secreted cytokines. In one embodiment, the target antigen, for which an antigen binding composition is sought, is immobilized on a surface, for example a cell culture plate or a bead. In another embodiment, the assay comprises a cell expressing the target antigen.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in these experiments are now described.

SpyCatcher and SpyTag Immune Receptor Construction

Four plasmids were ordered from Geneart containing the following sequences:

SpyTag, SpyTag-GGS, SpyCatcher, and SpyCatcher-GGS. Plasmids were digested with NheI and BamHI and bands corresponding to the SpyTag and SpyCatcher inserts were gel purified (Qiagen). The inserts were ligated into both pELNS and pELNS-GFP (both third generation self-inactivating lentiviral expression vectors, containing human CD3z or CD28-CD3z signaling endodomains, under an EF-1a promoter) using Rapid DNA Ligation Kit (Roche).

Recombinant Lentivirus Production

High-titer replication-defective lentiviral vectors were produced and concentrated as previously described (Song D G. et al., Cancer Res. 71:4617-27; Perez E. et al., Clin Immunol. 2005; 115:26-32). Briefly, 293T human embryonic kidney cells were transfected with pVSV-G (VSV glycoprotein expression plasmid), pRSV.REV (Rev expression plasmid), pMDLg/p.RRE (Gag/Pol expression plasmid), and pELNS transfer plasmid using Express Inn (Open Biosytems). The viral supernatant was harvested at 24 and 48 h posttransfection. Viral particles were concentrated and resuspended in 0.5 ml by ultracentrifugation for 2.5 h at 25,000 rpm with a Beckman SW28 rotor (Beckman Coulter, Fullerton, Calif.).

T Cells

Primary human CD4+ and CD8+ T cells were isolated from healthy volunteer donors following leukapheresis by negative selection, and purchased from the Human Immunology Core at University of Pennsylvania. All specimens were collected under a University Institutional Review Board-approved protocol, and written informed consent was obtained from each donor. CD4+ and CD8+ T cells were mixed at a 1:1 ratio and cultured in complete media (RPMI 1640 supplemented with 10% heat inactivated fetal bovine serum (FBS), 100 U/ml penicillin, 100 ug/ml streptomycin sulfate, 10-mM HEPES), and stimulated with anti-CD3 and anti-CD28 mAbs coated beads (Invitrogen) as described. 24 hr after activation, T cells were transduced with 50 μl of both 24 and 48 h lentiviral vectors since the MOI of each was unknown. Human recombinant interleukin-2 (IL-2; Novartis) was added every other day to 50 IU/ml final concentration and a 0.5-1×106 cells/ml cell density was maintained.

Production of SpyCatcher and SpyTag Proteins pSRTA plasmids containing A24-Protein G-SpyTag-Sortase or L17-Protein Z-SpyCatcher-Sortase and pEVOL-pBpF (Addgene) were co-transformed into T7 Expression Crystal Competent Cells (New England Biolabs). Bacterial cell starter cultures were grown in 2 mL of lysogeny broth (LB) for 4-6 h. The starter cultures were then used to inoculate 250 ml autoinduction media (Amresco) containing 50 mg/L ampicillin, 25 mg/L chloramphenicol, 0.1% arabinose, and 300 μM L-benzophenylalanine (BPA)(Bachem). Cultures were allowed to grown for 24-36 hours.

Bacterial cultures were centrifugally pelleted in 50 mL Falcon tubes at 5,500×g for 20 min. Pellets were resuspended in 4 mL B-PER Lysis buffer (Pierce) containing 50 μg/mL lysozyme, 1 μg/mL DNase, and ½ a tablet of cOmplete EDTA-free protease inhibitor (Sigma-Aldrich). Lysates were rotated at room temperature for 1 hr and subsequently centrifuged at 16,000 g for 10 min. Supernatants were combined and 9 mL of supernatant was incubated with 1 mL of TALON Metal Affinity Resin (Clontech) in a 10 mL Poly-Prep chromatography column (Bio-Rad) while rotated. Flow through was allowed to pass through the column and beads were washed three times with 10 mL 1×DPBS (Corning).

Conjugation and/or cleavage was carried out using either triglycine or triglycine-FAM. Briefly, the beads were resuspended in 1 mL 1×DPBS containing 250 μM triglycine or 250 μM triglycine-FAM and 50 μM $CaCl_2$. Columns were incubated at 37 C overnight to allow for sortease cleavage. Afterward, 0.2 mL 1×DPB was added and columns were eluted.

The proteins were further purified using RP-HPLC (Varian Prostar). A C8 300 Å 5 μm column (Agilent) was used. The proteins were eluted at 1.75 ml/min using a mixture of water and acetonitrile (both containing 0.1% TFA). The collected fractions were dried using a vacuum centrifugation concentrator (Labconco) and reconstituted in 1×DPBS. Protein concentration was determined using a NanoDrop (Thermo Scientific).

T Cell Labeling Using A24-Protein G-SpyTag-FAM and L17-Protein Z-SpyCatcher-FAM

T cells between days 14 and 22 post-transduction were collected and titers were measured using a Coulter Counter (Beckman Coulter). Cells were aliquoted into FACS tubes to a total cell count of $1.5×10^5$ cells. 1 mL of FACS buffer (2% heat inactivated fetal bovine serum in 1×PBS) was added to each tube and spun down at 1,200 rpm for 5 min. Media was removed from tubes and cells were washed once with FACS buffer. 100 μL of A24-Protein G-SpyTag-FAM or L17-Protein Z-SpyCatcher-FAM diluted to specified concentrations in 1×DPBS was added to the tubes and cells were resuspended. FACS tubes were placed at 4 C for 1 h. Cells were pelleted, washed three times with FACS buffer, and suspended in a final volume of 100 μL. FACS analysis of FAM labeled cells (GFP channel) was performed.

Functional Testing of SpyTag and SpyCatcher Immune Receptor Expressing T Cells

100 μL of varying concentrations of A24-Protein G-SpyTag and L17-Protein Z-SpyCatcher was added to wells in ELISA plates (Thermo Scientific). Proteins were allowed to passively adsorb to the plate overnight at 4 C. T cells between days 14 and 22 post-transduction were collected and titers were measured using a Coulter Counter (Beckman Coulter). Cells were spun down at 1,200 rpm for 5 min and resuspended in complete media to a final titer of $0.5×10^6$ cells/mL. Immediately prior to cell addition, ELISA plates were washed three times with 1×DPBS. 200 μL of cells was added to each well. The plates were incubated at 37 C and 5% $CO_2$ for 24 h. After incubation, plates were spun at 1,200 rpm for 5 min. 130 μL of supernatant was removed from each well, transferred to a new 96-well plate, and stored at −20C until further use. Supernatants were tested for Human INF-γ using an ELISA kit following standard protocol (Biolegend).

The results of the experiments are now described.

Figure 11:
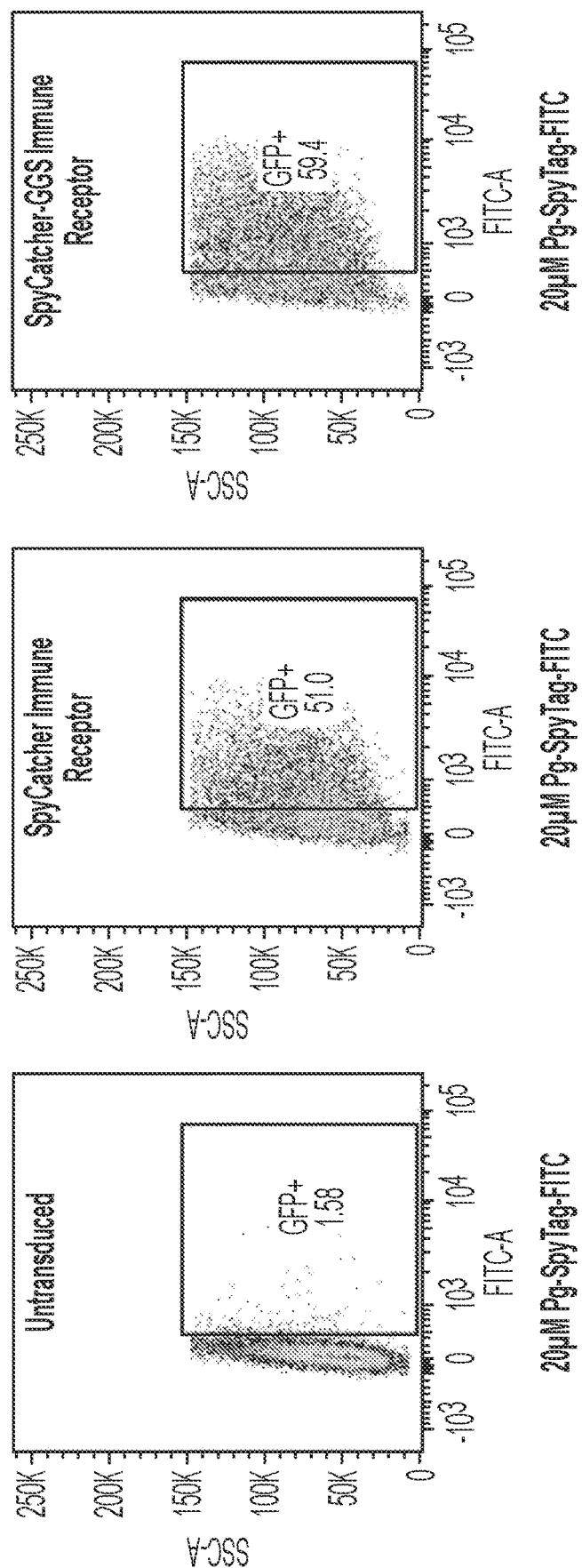
FIG. 11 is a series of graphs depicting the preliminary detection of SpyCatcher and SpyCatcher-GGS immune receptor expression using A24-Protein G-SpyTag-FITC.
Figure 12:
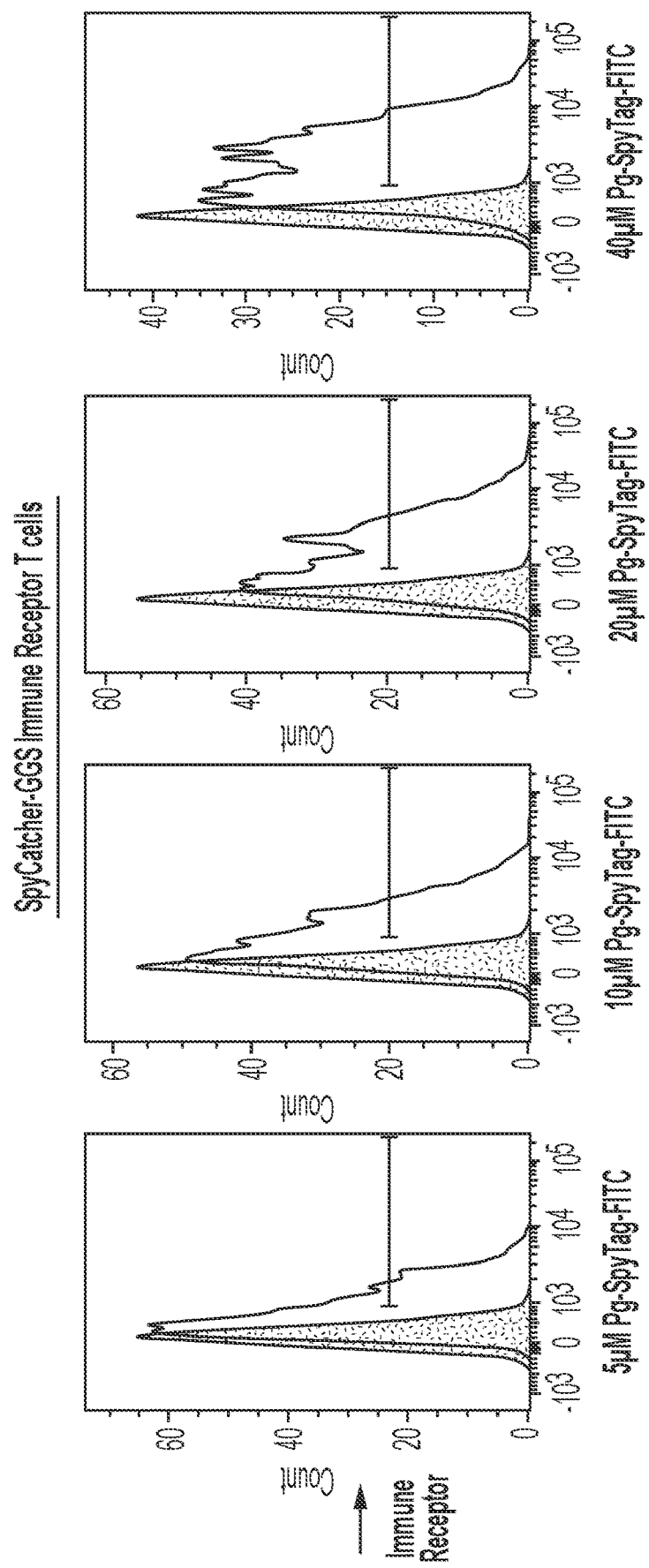
FIG. 12 is a series of graphs depicting the expression of SpyCatcher-GGS Immune Receptors T cells. The untransduced control (Grey histogram) and the SpyCatcher-GGS immune receptor expression (open histogram) were detected via A24-Protein G-SpyTag-FITC using FACS.
Figure 13:
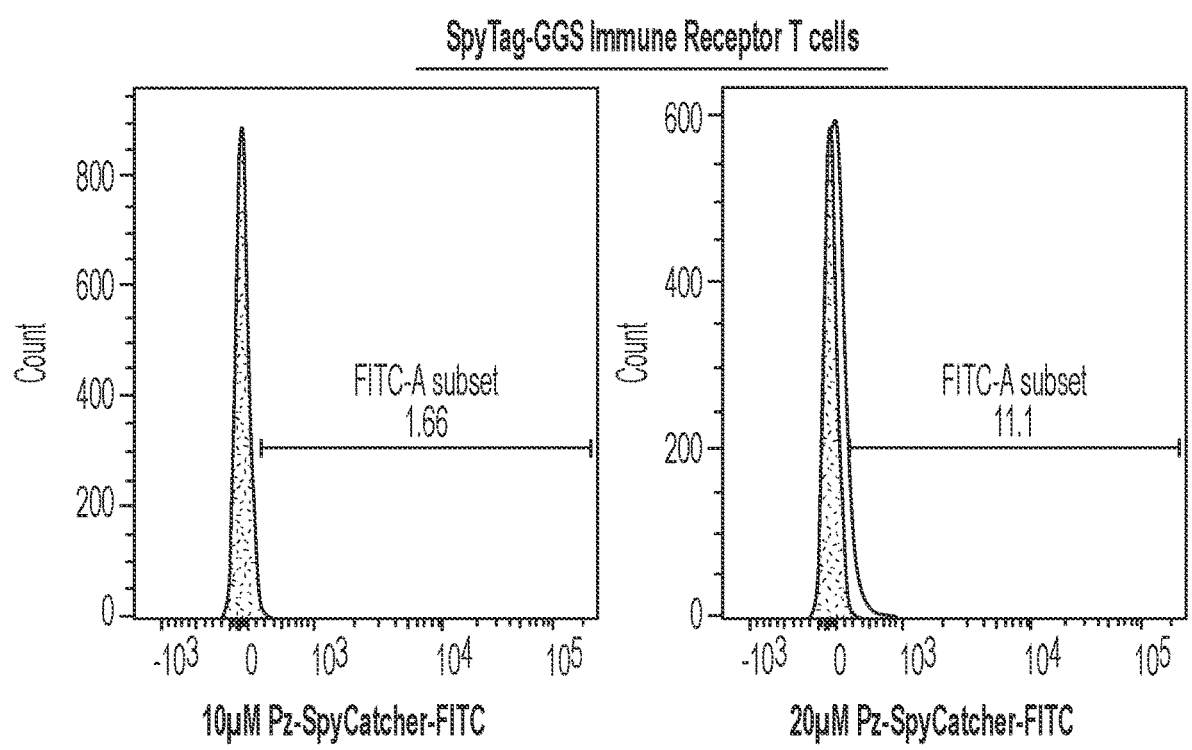
FIG. 13 is a series of graphs depicting the expression of SpyTag-GGS Immune Receptors T cells. The untransduced control (Grey histogram) and the SpyTag-GGS immune receptor expression (open histogram) were detected via L17-Protein Z-SpyCatcher-FITC using FACS.

A significant increase in cellular fluorescence was observed for cells transduced with the SpyCatcher/SpyTag Universal Immune Receptor, compared with untransduced cells, following incubation with the reciprocal SpyCatcher/SpyTag, which was fused to Protein G or Protein Z and labeled with FAM (FIG. 11). These findings confirm the specific interaction between the universal immune receptor and the reciprocal SpyCatcher/SpyTag. Consistent with these findings, the extent of labeling of Universal Immune Receptor T cells increased with dose of the FAM-labeled, reciprocal SpyCatcher/SpyTag construct, regardless of whether the universal immune receptor consisted of SpyCatcher or SpyTag (FIGS. 12 and 13). However, preliminary evidence suggests that cell labeling with the reciprocal SpyCatcher/SpyTag construct is more robust when T cells express a SpyCatcher Universal Immune Receptor (FIG. 12), as compared to the SpyTag Universal Immune receptor (FIG. 13).

Figure 14:
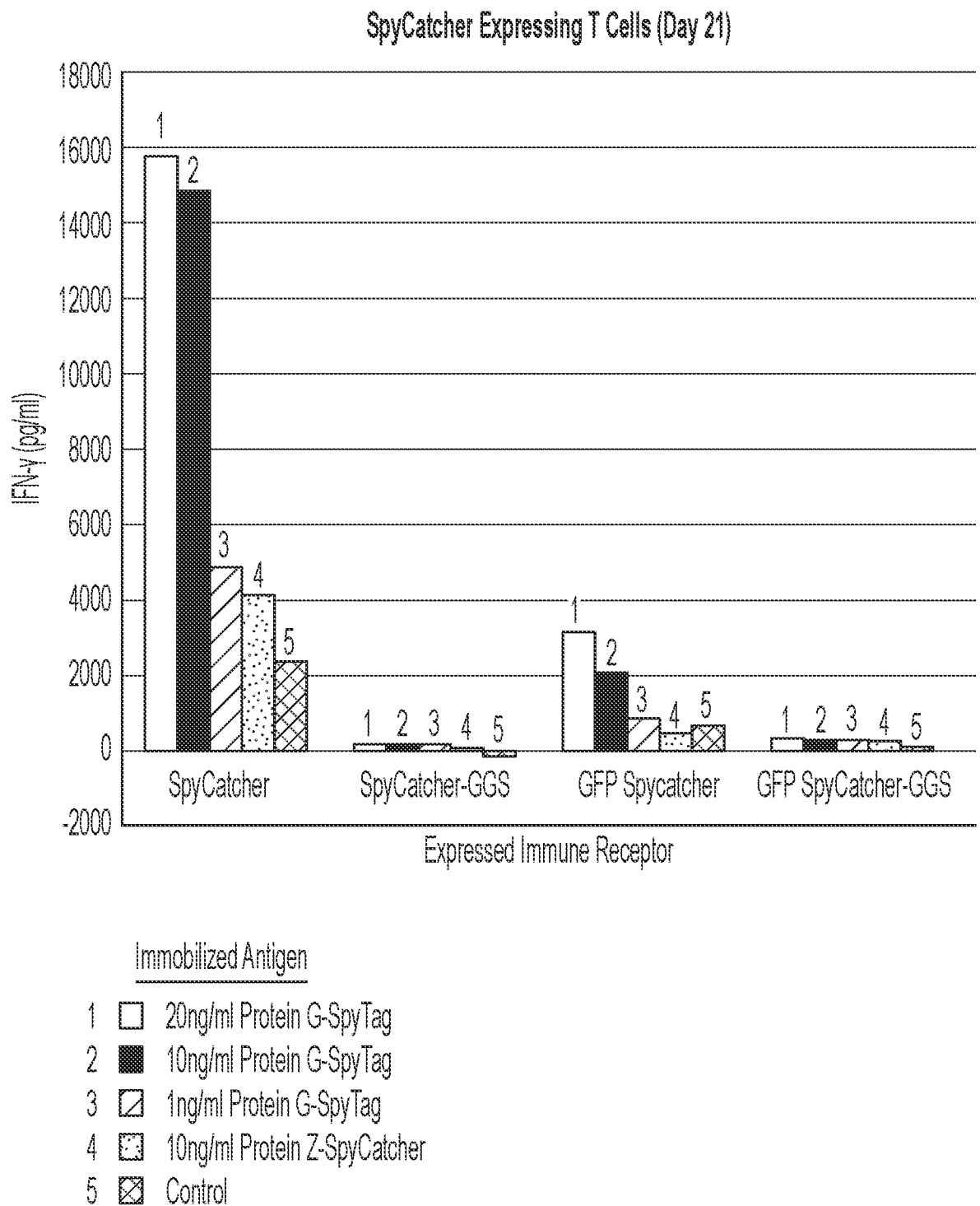
FIG. 14 is a series of histograms depicting the functional testing of Stag-IR and SC-IR T cells using Cell ELISA.

It was found that T cells expressing the SpyCatcher Universal Immune Receptor exhibited dose dependent activation, indicated by secretion of IFNγ, upon binding to the SpyTag-coated ELISA plates (FIG. 14). Activation was significantly reduced in universal immune receptors that possessed an additional GGS linker between SpyCatcher and the hinge region. A lower level of T cell activation was also observed when T cells were engineered to express GFP in addition to the SpyCatcher Universal Immune Receptor, both with and without the GGS linker.

As seen in FIG. 11, primary human T cells engineered to express a SpyCatcher Immune Receptor are capable of binding soluble FITC labeled, SpyTag-Protein-g conjugate (Pg-SpyTag-FITC) as assessed by flow cytometry. SpyCatcher Immune Receptors constructed with or without a GGS linker were capable of binding Pg-SpyTag-FITC. Untransduced control T cells from the same donor do not bind Pg-SpyTag-FITC.

As seen in FIG. 12, primary human T cells engineered to express a SpyCatcher Immune Receptor are capable of binding soluble FITC labeled, SpyTag-Protein-g conjugate (Pg-SpyTag-FITC) at various concentrations (5-40 uM), with concentration dependent binding. Negative control untransduced T cells labeled at the 40 uM concentration are shown in the gray histograms.

As seen in FIG. 13, primary human T cells engineered to express a SpyTag Immune Receptor bind soluble FITC labeled, SpyCatcher-Protein-g conjugate (Pg-SpyTag-FITC) at the 20 uM concentration. Unlabeled T cells are shown in the gray histograms.

As seen in FIG. 14, SpyCatcher Immune Receptor expressing T cells secrete IFNγ in response to plate bound A24-Protein G-SpyTag. The level of IFNγ secreted by SpyCatcher Immune Receptor expressing T cells was dependent upon the amount of A24-Protein G-SpyTag immobilized to the surface of the plate. IFNγ secretion was also detected in supernatants of stimulated SpyCatcher Immune Receptor expressing T cells when a GFP tag was incorporated into the overall construct. SpyTag expressing T cells do not secrete IFNγ in response to plate bound A24-Protein G-SpyTag or L17-Protein Z-SpyCatcher. These results revealed that the SpyCatcher Immune Receptor has increased activity compared to the SpyTag Immune Receptor.

Figure 15A:
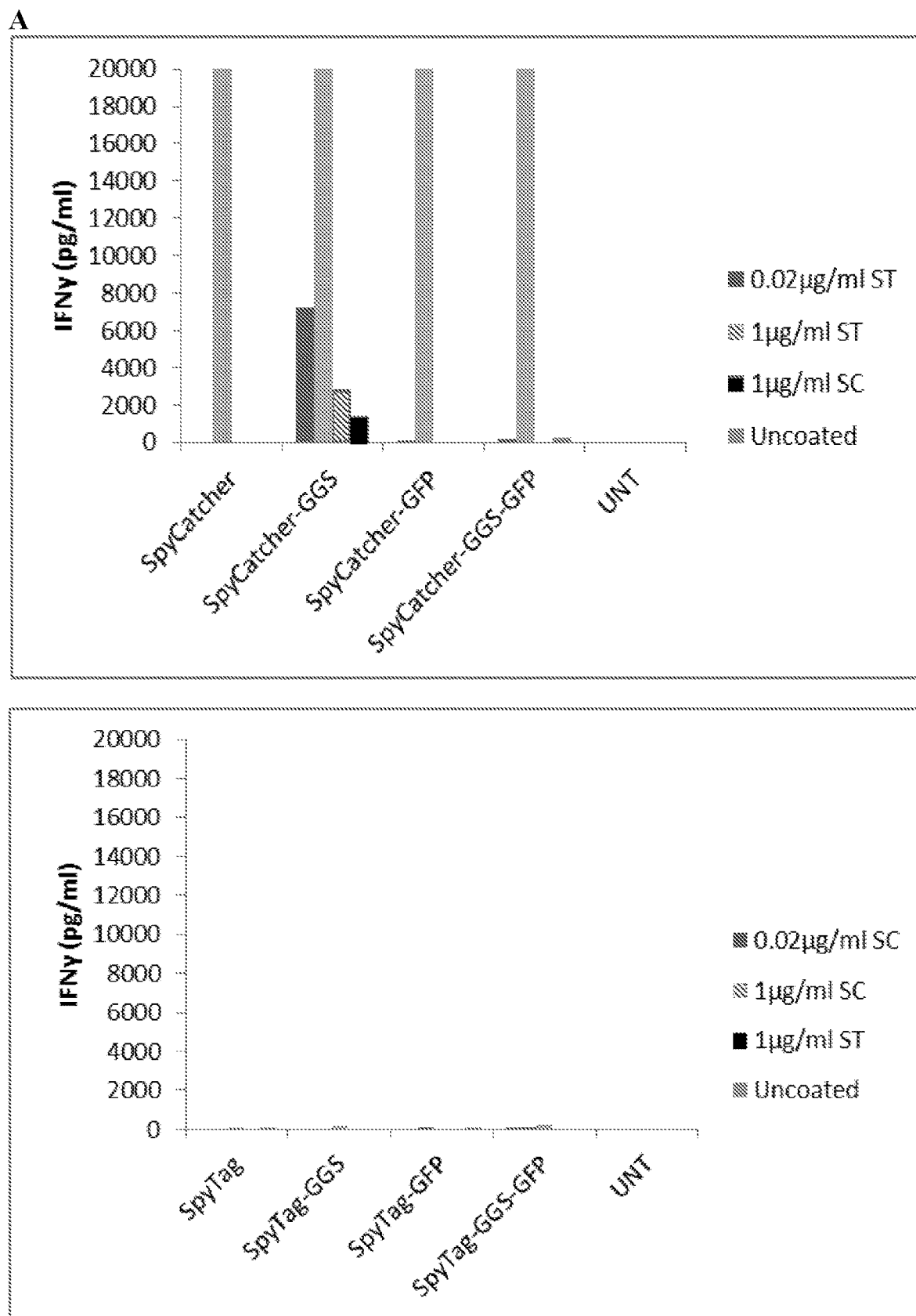
FIGS. 15A-15B are a series of histograms depicting the functional testing of SpyCatcher and SpyTag Immune Receptors.
Figure 15B:
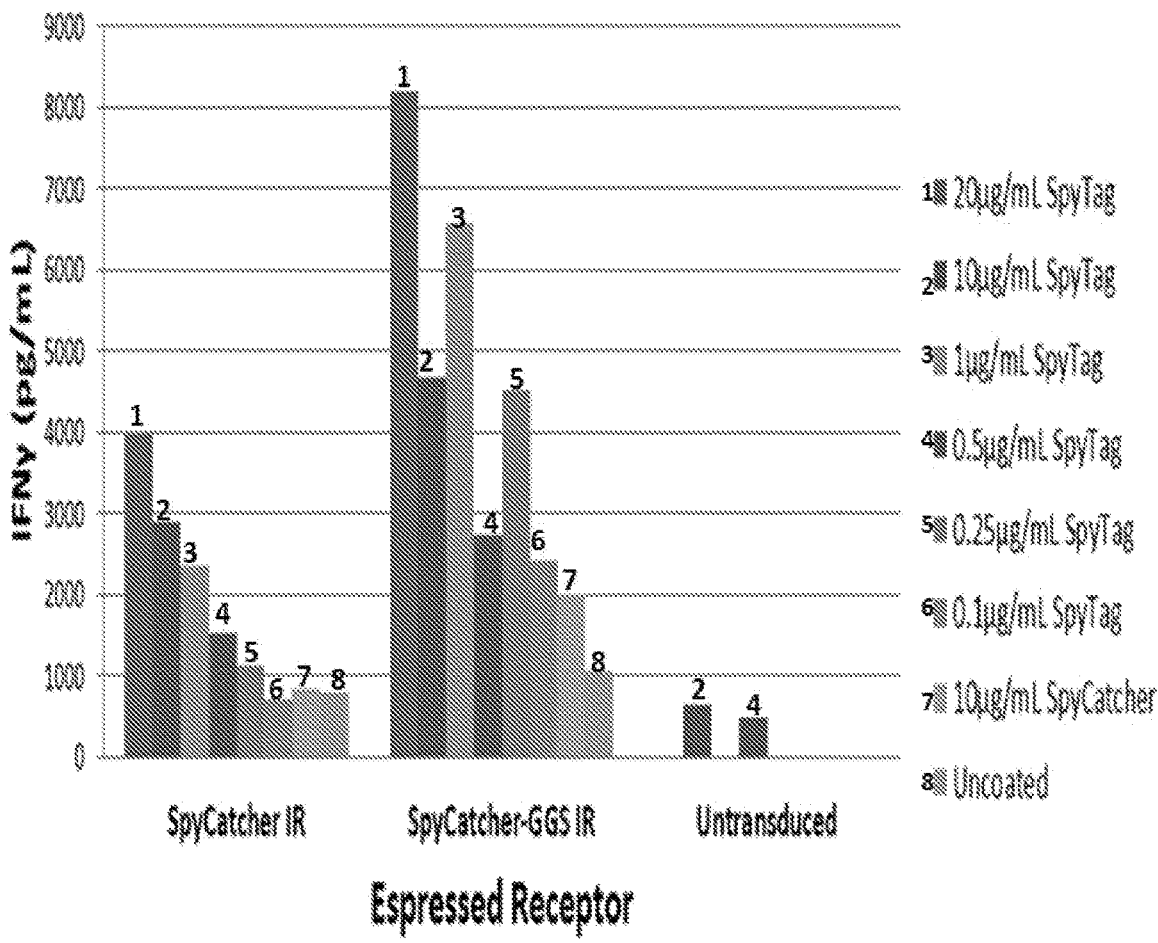

As seen in FIG. 15A, SpyCatcher expressing T cells secrete IFNγ in response to plate bound A24-Protein G-SpyTag at a 1 ug/mL concentration. SpyCatcher expressing T cells do not secrete IFNγ in response to plate bound L17-Protein Z-SpyCatcher. SpyTag expressing T cells do not secrete IFNγ in response to plate bound A24-Protein G-SpyTag or L17-Protein Z-SpyCatcher. These results revealed that the T cells engineered to express the SpyCatcher Immune receptor are conferred with the ability to bind and respond against SpyTag protein. As seen in FIG. 15B, SpyCatcher expressing T cells secrete IFNγ in response to plate bound A24-Protein G-SpyTag in a dose dependent manner. By comparison, untransduced T cells from the same donor do not produce high levels of IFNγ in response to plate bound A24-Protein G-SpyTag.

Figure 16B:
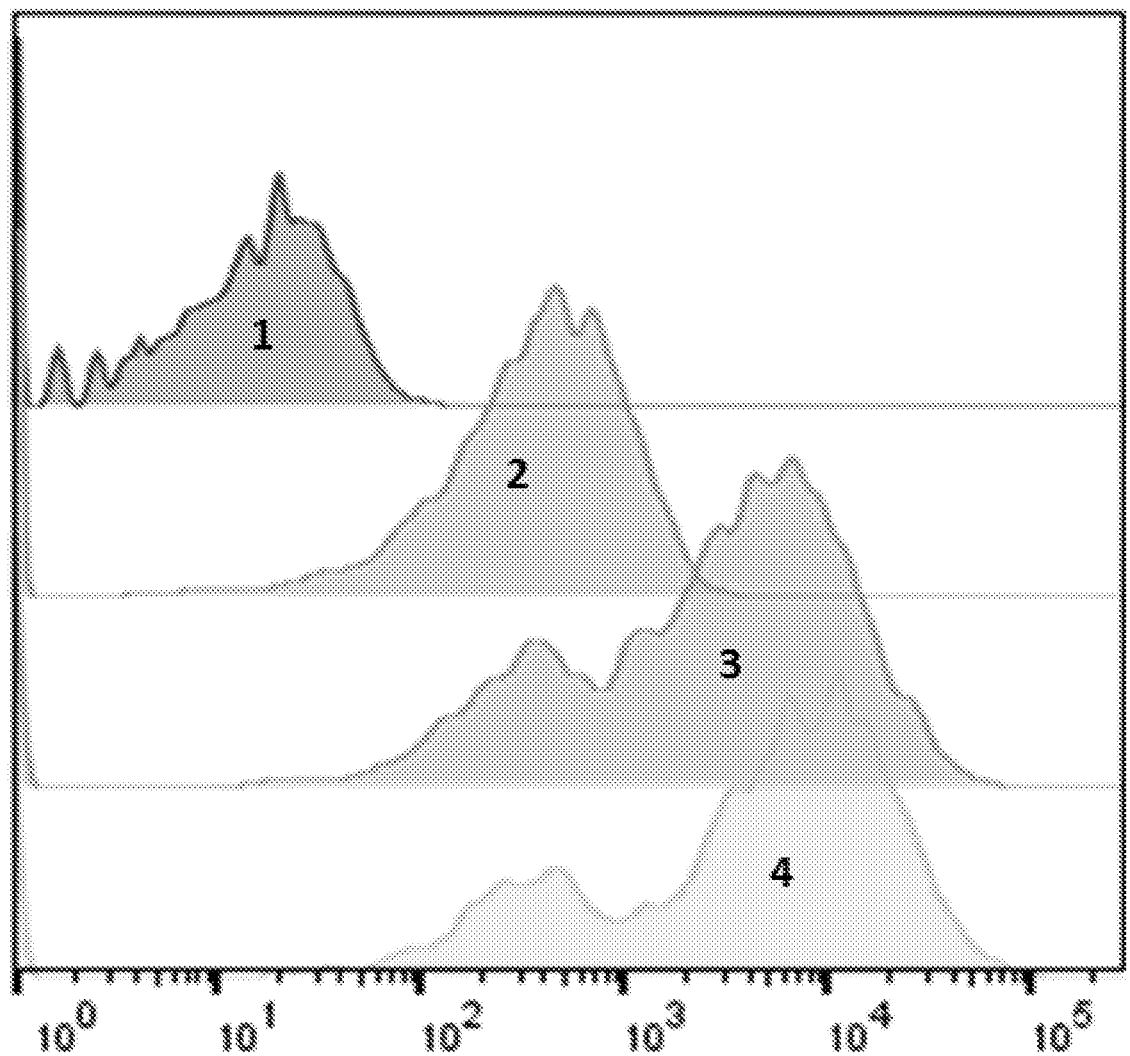

As shown in FIGS. 16A-16B, SpyCatcher T cells were labeled with Protein G-SpyTag and Biotin-Herceptin. Primary human T cells were transduced with lentivirus containing GFP and SpyCatcher immune receptor. Day 9 post activation, T cells were taken and labeled with SpyTag-Protein G, followed by biotin-herceptin and streptavidin-APC. Staining of cells was determined by flow cytometric analysis gating on live cells. Herceptin is known in the art as a monoclonal antibody that selectively binds with high affinity to the human epidermal growth factor receptor 2 (HER2), known to be overexpressed in about 30% of breast cancers.

As shown in FIG. 17, pre-targeting Her2+ tumor cells with Herceptin-SpyTag leads to lysis by SpyCatcher T cells. Her2+ luciferase+tumor cells were incubated with varying amounts of Herceptin-SpyTag for 1 hour at 37 C, washed twice, and plated at a density of 1×10$^4$ cells per well in a 96 well plate. 1×10$^5$ SpyCatcher T cells (75% receptor expressing) were added to each well and incubated for 20 hours at 37 C. Luciferase activity was measured and specific lysis was calculated compared to tumor only control.

Figure 18A:
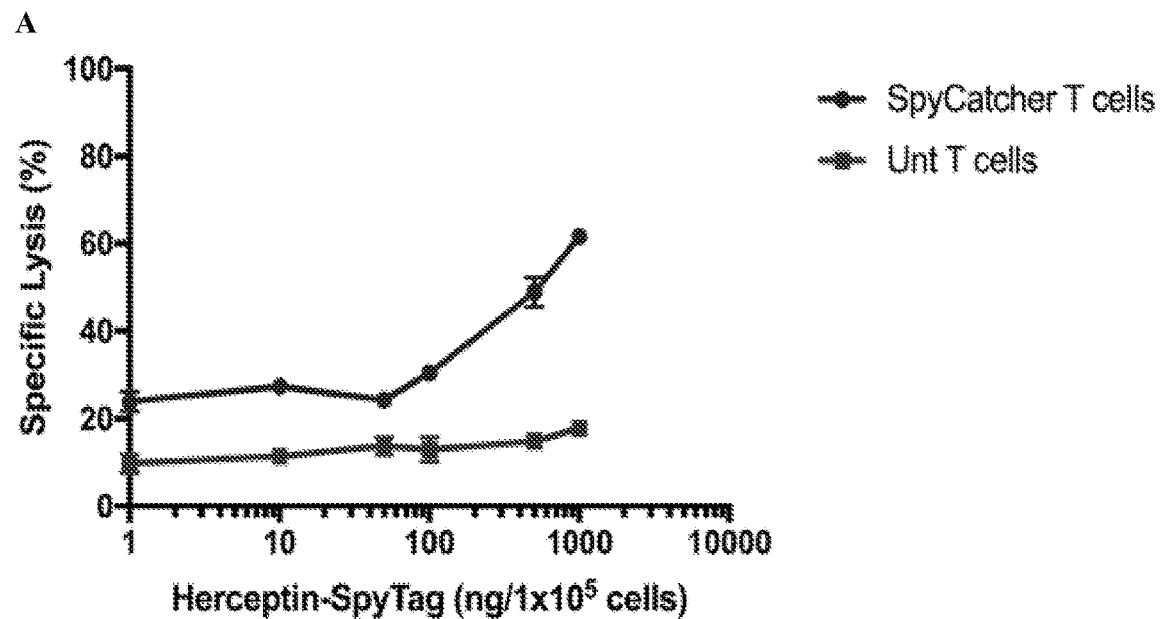
FIGS. 18A-18B are a series of graphs showing that pre-arming SpyCatcher T cells with Herceptin-SpyTag leads to dose dependent lysis of SKBR3 tumor cells.
Figure 18B:
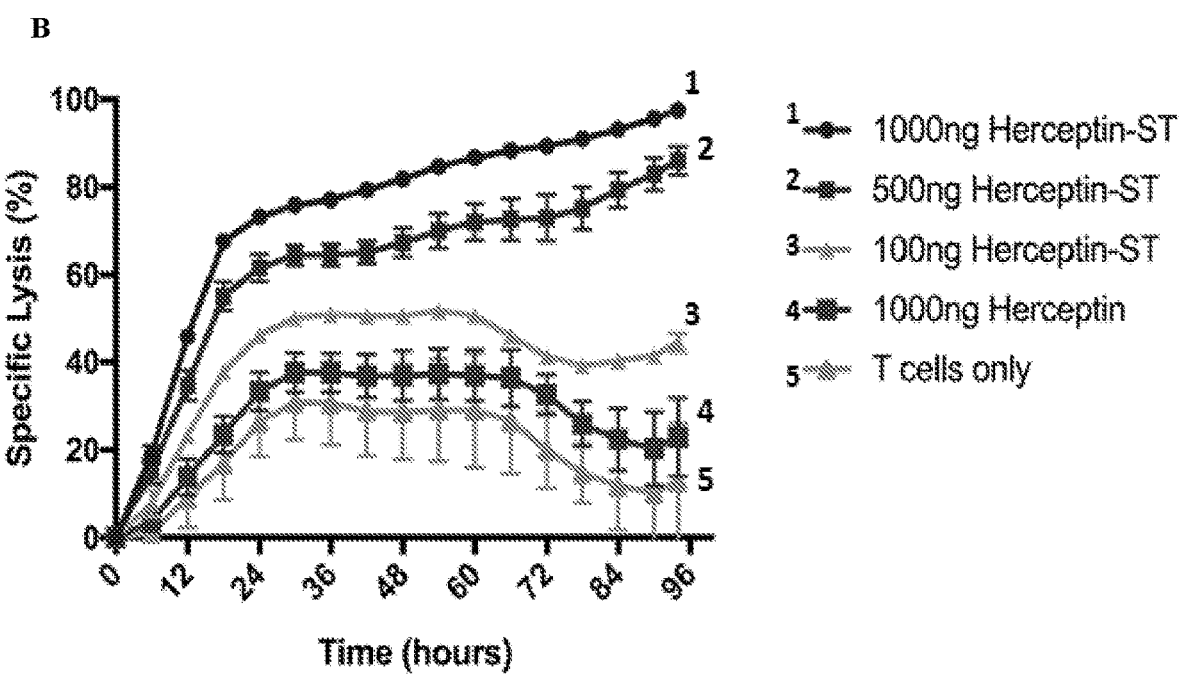

As shown in FIGS. 18A-18B, pre-arming SpyCatcher T cells with Herceptin-SpyTag leads to dose dependent lysis of SKBR3 tumor cells. xCellegence plates were seeded with 1×10$^4$ SKBR3 cells/well and baseline reading was allowed to establish overnight, with measurement intervals set at 20 minutes. SpyCatcher T cells (75% receptor positive) were incubated with varying amounts of Herceptin-SpyTag for 1 hour at 37 C, washed, and added to wells at a density of 1×10$^5$ cells/well. Measurements were continued for 4 days. xCellegence software was used to normalize readings and calculate specific lysis values compared to tumor only control.

As shown in FIG. 19, arming and targeting with Herceptin-SpyTag can be combined. Tumor cells were incubated with Herceptin-SpyTag (100 ng/1×10$^5$ cells), washed, and seeded in a 96 well plate at 1×10$^4$ cells/well. SpyCatcher T cells (75% receptor expressing) were incubated with varying concentrations of Herceptin-SpyTag, washed, and added to each well at a density of 1×10$^5$ cells/well. Luciferase activity was measured and specific lysis was calculated compared to tumor only control.

Table 1 below summarizes the sequence identifiers for the eight different of SpyCatcher/SpyTag Immune Receptor constructs of the present invention (FIGS. 3B, 4B, 5B, 6B, 7B, 8B, 9B, 10B).

TABLE 1

Sequence identifiers for the present SpyCatcher/SpyTag constructs

| SEQ ID NO: | IDENTITY |
|---|---|
| SEQ ID NO: 1 | pELNS(SpeI)-GFP-SpyTag-CD28-Zeta, nucleic acid sequence |
| SEQ ID NO: 2 | pELNS(SpeI)-GFP-SpyTag-CD28-Zeta, amino acid sequence |
| SEQ ID NO: 3 | pELNS(SpeI)-GFP-SpyTag-GGS-CD28-Zeta, nucleic acid sequence |
| SEQ ID NO: 4 | pELNS(SpeI)-GFP-SpyTag-GGS-CD28-Zeta, amino acid sequence |
| SEQ ID NO: 5 | pELNS(SpeI)-SpyCatcher-CD28-Zeta, nucleic acid sequence |
| SEQ ID NO: 6 | pELNS(SpeI)-SpyCatcher-CD28-Zeta, amino acid sequence |
| SEQ ID NO: 7 | pELNS(SpeI)-SpyCatcher-GGS-CD28-Zeta, nucleic acid sequence |
| SEQ ID NO: 8 | pELNS(SpeI)-SpyCatcher-GGS-CD28-Zeta, amino acid sequence |
| SEQ ID NO: 9 | pELNS(SpeI)-SpyTag-CD28-Zeta, nucleic acid sequence |
| SEQ ID NO: 10 | pELNS(SpeI)-SpyTag-CD28-Zeta, amino acid sequence |
| SEQ ID NO: 11 | pELNS(SpeI)-SpyTag-GGS-CD28-Zeta, nucleic acid sequence |
| SEQ ID NO: 12 | pELNS(SpeI)-SpyTag-GGS-CD28-Zeta, amino acid sequence |
| SEQ ID NO: 13 | pELNS(SpeI)-GFP-SpyCatcher-CD28-Zeta, nucleic acid sequence |

TABLE 1-continued

Sequence identifiers for the present SpyCatcher/SpyTag constructs

| SEQ ID NO: | IDENTITY |
|---|---|
| SEQ ID NO: 14 | pELNS(SpeI)-GFP-SpyCatcher-CD28-Zeta amino acid sequence |
| SEQ ID NO: 15 | pELNS(SpeI)-GFP-SpyCatcher-GGS-CD28-Zeta, nucleic acid sequence |
| SEQ ID NO: 16 | pELNS(SpeI)-GFP-SpyCatcher-GGS-CD28-Zeta, amino acid sequence |

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A nucleic acid molecule encoding a universal immune receptor fusion protein comprising, in order, a SpyCatcher extracellular binding domain, a CD8a extracellular hinge region, a CD8a transmembrane domain, a 4-1BB costimulatory molecule and a CD3-zeta intracellular signaling domain.

2. A universal immune receptor fusion protein comprising, in order, a SpyCatcher extracellular binding domain, a CD8a extracellular hinge region, a CD8a transmembrane domain, a 4-1BB costimulatory molecule and a CD3-zeta intracellular signaling domain.

3. A cell comprising a nucleic acid molecule encoding the universal immune receptor fusion protein of claim 2.

4. The cell of claim 3 wherein the cell is an immune cell.

5. The cell of claim 3, wherein the cell is selected from the group consisting of a T cell, a Natural Killer (NK) cell, a cytotoxic T lymphocyte (CTL), a macrophage, a stem cell, and a regulatory T cell.

6. The cell of claim 4, wherein the cell is activated when the isolated universal immune receptor fusion protein forms a covalent bond with a fusion protein comprising SpyTag and a targeting ligand.

7. The cell of claim 6, wherein the targeting ligand is selected from; an oligonucleotide, an antibody, an antibody fragment, a scFv, a protein scaffold, a peptide, a ligand, an aptamer, a labelling agent, a tumor antigen, a self-antigen, a viral antigen, and any combination thereof.

8. A vector comprising the nucleic acid molecule of claim 1.

9. A method for stimulating a universal immune receptor-mediated immune response in a mammal, the method comprising administering to a mammal an effective amount of the cells of claim 4.

10. The method of claim 9, wherein the universal immune receptor-mediated immune response is stimulated when the isolated universal immune receptor fusion protein forms a covalent bond with a fusion protein comprising SpyTag and a targeting ligand.

11. The method of claim 10, wherein the targeting ligand molecule is selected from; an oligonucleotide, an antibody, an antibody fragment, a scFv, a protein scaffold, a peptide, a ligand, an aptamer, a labelling agent, a tumor antigen, a self-antigen, a viral antigen, and any combination thereof.

12. The method of claim 11, wherein the targeting ligand is an antibody.

13. The method of claim 9, wherein the cells are T cells, Natural Killer (NK) cells, cytotoxic T lymphocytes (CTL), macrophages, a stem cells, or regulatory T cells.

14. The method of claim 9, wherein the method comprises administering the fusion protein comprising SpyTag to the mammal prior to administering the cells.

15. The method of claim 9, wherein the method comprises administering a plurality of the fusion proteins comprising SpyTag to the mammal prior to administering the cells.

16. The method of claim 9, wherein the method comprises binding the universal immune receptor fusion protein with the fusion protein comprising SpyTag prior to administering the cells to the mammal.

17. The method of claim 9, wherein the cells are autologous cells.

18. The method of claim 9, wherein the mammal is treated for a disorder selected from the group consisting of a viral, a bacterial and a parasitic infection, an autoimmune disease and a cancer.

19. The method of claim 9, wherein the mammal is treated for a cancer.

20. The method of claim 9, wherein the mammal is a human.

* * * * *

UNITED STATES PATENT AND TRADEMARK OFFICE
CERTIFICATE OF CORRECTION

| | | |
|---|---|---|
| PATENT NO. | : 11,377,481 B2 | Page 1 of 1 |
| APPLICATION NO. | : 16/064875 | |
| DATED | : July 5, 2022 | |
| INVENTOR(S) | : Powell et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 797 days.

Signed and Sealed this
Seventh Day of January, 2025

Derrick Brent
*Acting Director of the United States Patent and Trademark Office*

SEQUENCE LISTING

```
<160> NUMBER OF SEQ ID NOS: 16

<210> SEQ ID NO 1
<211> LENGTH: 1587
<212> TYPE: DNA
<213> ORGANISM: Artificial Sequence
<220> FEATURE:
<223> OTHER INFORMATION: Artificially Synthesized

<400> SEQUENCE: 1
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagaga     720
tctggcagcg gagagggcag aggaagtctt ctaacatgcg gtgacgtgga ggagaatccc     780
ggccctagaa tggccttacc agtgaccgcc ttgctcctgc cgctggcctt gctgctccac     840
gccgccaggc cgggatccgc ccacattgtg atggtggacg cctacaagcc caccaaggct     900
agcaccacga cgccagcgcc gcgaccacca acaccggcgc ccaccatcgc gtcgcagccc     960
ctgtccctgc gcccagaggc gtgccggcca gcggcggggg cgcagtgcac acgagggg    1020 ctggacttcg cctgtgattt ttgggtgctg gtggtggttg gtggagtcct ggcttgctat    1080
agcttgctag taacagtggc ctttattatt ttctgggtga ggagtaagag gagcaggctc    1140
ctgcacagtg actacatgaa catgactccc cgccgccccg gcccacccg caagcattac    1200 cagccctatg ccccaccacg cgacttcgca gcctatcgct ccatcgatag agtgaagttc    1260
agcaggagcg cagacgcccc cgcgtaccag cagggccaga accagctcta taacgagctc    1320
aatctaggac gaagagagga gtacgatgtt ttggacaaga cgtggccg ggaccctgag    1380 atggggggaa agccgagaag gaagaaccct caggaaggcc tgtacaatga actgcagaaa    1440
gataagatgg cggaggccta cagtgagatt gggatgaaag gcgagcgccg gaggggcaag    1500
gggcacgatg gcctttacca gggtctcagt acagccacca aggacaccta cgacgccctt    1560
```
cacatgcagg ccctgccccc tcgctaa                                                    1587

<210> SEQ ID NO 2
<211> LENGTH: 528
<212> TYPE: PRT
<213> ORGANISM: Artificial Sequence
<220> FEATURE:
<223> OTHER INFORMATION: Artificially Synthesized

<400> SEQUENCE: 2

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Arg
225                 230                 235                 240

Ser Gly Ser Gly Glu Gly Arg Gly Ser Leu Leu Thr Cys Gly Asp Val
                245                 250                 255

Glu Glu Asn Pro Gly Pro Arg Met Ala Leu Pro Val Thr Ala Leu Leu
            260                 265                 270

Leu Pro Leu Ala Leu Leu Leu His Ala Ala Arg Pro Gly Ser Ala His
        275                 280                 285

Ile Val Met Val Asp Ala Tyr Lys Pro Thr Lys Ala Ser Thr Thr Thr
290                 295                 300

Pro Ala Pro Arg Pro Pro Thr Pro Ala Pro Thr Ile Ala Ser Gln Pro
305                 310                 315                 320

Leu Ser Leu Arg Pro Glu Ala Cys Arg Pro Ala Ala Gly Gly Ala Val
                325                 330                 335

His Thr Arg Gly Leu Asp Phe Ala Cys Asp Phe Trp Val Leu Val Val
            340                 345                 350

| | | | | | | | | | | | | |
|---|---|---|---|---|---|---|---|---|---|---|---|---|
|Val|Gly|Gly|Val|Leu|Ala|Cys|Tyr|Ser|Leu|Leu|Val|Thr|Val|Ala|Phe|
| | |355| | | |360| | | |365| | | | | |

| | | | | | | | | | | | |
|---|---|---|---|---|---|---|---|---|---|---|---|
|Ile|Ile|Phe|Trp|Val|Arg|Ser|Lys|Arg|Ser|Arg|Leu|Leu|His|Ser|Asp|
| | |370| | | |375| | | |380| | | | | |

| | | | | | | | | | | | |
|---|---|---|---|---|---|---|---|---|---|---|---|
|Tyr|Met|Asn|Met|Thr|Pro|Arg|Arg|Pro|Gly|Pro|Thr|Arg|Lys|His|Tyr|
|385| | | |390| | | |395| | | |400| | | |

| | | | | | | | | | | | |
|---|---|---|---|---|---|---|---|---|---|---|---|
|Gln|Pro|Tyr|Ala|Pro|Pro|Arg|Asp|Phe|Ala|Ala|Tyr|Arg|Ser|Ile|Asp|
| | | |405| | | |410| | | |415| | | | |

| | | | | | | | | | | | |
|---|---|---|---|---|---|---|---|---|---|---|---|
|Arg|Val|Lys|Phe|Ser|Arg|Ser|Ala|Asp|Ala|Pro|Ala|Tyr|Gln|Gln|Gly|
| | | |420| | | |425| | | |430| | | | |

| | | | | | | | | | | | |
|---|---|---|---|---|---|---|---|---|---|---|---|
|Gln|Asn|Gln|Leu|Tyr|Asn|Glu|Leu|Asn|Leu|Gly|Arg|Arg|Glu|Glu|Tyr|
| | |435| | | |440| | | |445| | | | | |

| | | | | | | | | | | | |
|---|---|---|---|---|---|---|---|---|---|---|---|
|Asp|Val|Leu|Asp|Lys|Arg|Arg|Gly|Arg|Asp|Pro|Glu|Met|Gly|Gly|Lys|
| | |450| | | |455| | | |460| | | | | |

| | | | | | | | | | | | |
|---|---|---|---|---|---|---|---|---|---|---|---|
|Pro|Arg|Arg|Lys|Asn|Pro|Gln|Glu|Gly|Leu|Tyr|Asn|Glu|Leu|Gln|Lys|
|465| | | |470| | | |475| | | |480| | | |

| | | | | | | | | | | | |
|---|---|---|---|---|---|---|---|---|---|---|---|
|Asp|Lys|Met|Ala|Glu|Ala|Tyr|Ser|Glu|Ile|Gly|Met|Lys|Gly|Glu|Arg|
| | | |485| | | |490| | | |495| | | | |

| | | | | | | | | | | | |
|---|---|---|---|---|---|---|---|---|---|---|---|
|Arg|Arg|Gly|Lys|Gly|His|Asp|Gly|Leu|Tyr|Gln|Gly|Leu|Ser|Thr|Ala|
| | |500| | | |505| | | |510| | | | | |

| | | | | | | | | | | | |
|---|---|---|---|---|---|---|---|---|---|---|---|
|Thr|Lys|Asp|Thr|Tyr|Asp|Ala|Leu|His|Met|Gln|Ala|Leu|Pro|Pro|Arg|
| | |515| | | |520| | | |525| | | | | |

<210> SEQ ID NO 3
<211> LENGTH: 1650
<212> TYPE: DNA
<213> ORGANISM: Artificial Sequence
<220> FEATURE:
<223> OTHER INFORMATION: Artificially Synthesized

<400> SEQUENCE: 3

```
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagaga     720
tctggcagcg gagagggcag aggaagtctt ctaacatgcg gtgacgtgga ggagaatccc     780
ggccctagaa tggccttacc agtgaccgcc ttgctcctgc cgctggcctt gctgctccac     840
gccgccaggc cggatccgc ccacatcgtg atggtggacg cctacaagcc caccaagggc     900
ggcagcggcg gcagcggcgg cagcggcggc agcggcggca gcggcggcag cggcggcagc     960
gctagcacca cgacgccagc gccgcgacca ccaacaccgg cgcccaccat cgcgtcgcag    1020
cccctgtccc tgcgcccaga ggcgtgccgg ccagcggcgg ggggcgcagt gcacacgagg    1080
```

-continued

```
gggctggact tcgcctgtga tttttgggtg ctggtggtgg ttggtggagt cctggcttgc   1140
tatagcttgc tagtaacagt ggcctttatt attttctggg tgaggagtaa gaggagcagg   1200
ctcctgcaca gtgactacat gaacatgact ccccgccgcc ccgggcccac ccgcaagcat   1260
taccagccct atgccccacc acgcgacttc gcagcctatc gctccatcga tagagtgaag   1320
ttcagcagga gcgcagacgc ccccgcgtac cagcagggcc agaaccagct ctataacgag   1380
ctcaatctag gacgaagaga ggagtacgat gttttggaca agagacgtgg ccgggaccct   1440
gagatggggg gaaagccgag aaggaagaac cctcaggaag gcctgtacaa tgaactgcag   1500
aaagataaga tggcggaggc ctacagtgag attgggatga aggcgagcg ccggaggggc   1560 aaggggcacg atggccttta ccagggtctc agtacagcca ccaaggacac ctacgacgcc   1620
cttcacatgc aggccctgcc ccctcgctaa                                    1650
```

<210> SEQ ID NO 4
<211> LENGTH: 549
<212> TYPE: PRT
<213> ORGANISM: Artificial Sequence
<220> FEATURE:
<223> OTHER INFORMATION: Artificially Synthesized

<400> SEQUENCE: 4

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Arg
225                 230                 235                 240

Ser Gly Ser Gly Glu Gly Arg Gly Ser Leu Leu Thr Cys Gly Asp Val
                245                 250                 255

Glu Glu Asn Pro Gly Pro Arg Met Ala Leu Pro Val Thr Ala Leu Leu
```

```
                260                 265                 270
Leu Pro Leu Ala Leu Leu His Ala Ala Arg Pro Gly Ser Ala His
            275                 280                 285
Ile Val Met Val Asp Ala Tyr Lys Pro Thr Lys Gly Gly Ser Gly Gly
            290                 295                 300
Ser Gly Gly Ser Gly Gly Ser Gly Gly Ser Gly Gly Ser Gly Gly Ser
305                 310                 315                 320
Ala Ser Thr Thr Thr Pro Ala Pro Arg Pro Thr Pro Ala Pro Thr
                325                 330                 335
Ile Ala Ser Gln Pro Leu Ser Leu Arg Pro Glu Ala Cys Arg Pro Ala
            340                 345                 350
Ala Gly Gly Ala Val His Thr Arg Gly Leu Asp Phe Ala Cys Asp Phe
            355                 360                 365
Trp Val Leu Val Val Val Gly Gly Val Leu Ala Cys Tyr Ser Leu Leu
    370                 375                 380
Val Thr Val Ala Phe Ile Ile Phe Trp Val Arg Ser Lys Arg Ser Arg
385                 390                 395                 400
Leu Leu His Ser Asp Tyr Met Asn Met Thr Pro Arg Arg Pro Gly Pro
                405                 410                 415
Thr Arg Lys His Tyr Gln Pro Tyr Ala Pro Pro Arg Asp Phe Ala Ala
                420                 425                 430
Tyr Arg Ser Ile Asp Arg Val Lys Phe Ser Arg Ser Ala Asp Ala Pro
            435                 440                 445
Ala Tyr Gln Gln Gly Gln Asn Gln Leu Tyr Asn Glu Leu Asn Leu Gly
            450                 455                 460
Arg Arg Glu Glu Tyr Asp Val Leu Asp Lys Arg Arg Gly Arg Asp Pro
465                 470                 475                 480
Glu Met Gly Gly Lys Pro Arg Arg Lys Asn Pro Gln Glu Gly Leu Tyr
                485                 490                 495
Asn Glu Leu Gln Lys Asp Lys Met Ala Glu Ala Tyr Ser Glu Ile Gly
                500                 505                 510
Met Lys Gly Glu Arg Arg Arg Gly Lys Gly His Asp Gly Leu Tyr Gln
            515                 520                 525
Gly Leu Ser Thr Ala Thr Lys Asp Thr Tyr Asp Ala Leu His Met Gln
            530                 535                 540
Ala Leu Pro Pro Arg
545

<210> SEQ ID NO 5
<211> LENGTH: 1017
<212> TYPE: DNA
<213> ORGANISM: Artificial Sequence
<220> FEATURE:
<223> OTHER INFORMATION: Artificially Synthesized

<400> SEQUENCE: 5
atggccttac cagtgaccgc cttgctcctg ccgctggcct tgctgctcca cgccgccagg    60
ccgggatccg gaagcggaga tagcgccacc cacatcaagt tcagcaagcg ggacgaggac   120
ggcaaagagc tggctggcgc caccatggaa ctgcgggata gcagcggcaa gaccatcagc   180
acctggatca gcgacggcca ggtcaaagac ttctacctgt accccggcaa gtacaccttc   240
gtggaaacag ccgcccctga cggctatgag gtggccacag ccatcaccttc accgtgaac   300 gagcagggac aggtcacagt gaacggcgct agcaccacga cgccagcgcc gcgaccacca   360
acaccggcgc ccaccatcgc gtcgcagccc ctgtccctgc gcccagaggc gtgccggcca   420
```

```
gcggcggggg gcgcagtgca cacgaggggg ctggacttcg cctgtgattt ttgggtgctg    480
gtggtggttg gtggagtcct ggcttgctat agcttgctag taacagtggc ctttattatt    540
ttctgggtga ggagtaagag gagcaggctc ctgcacagtg actacatgaa catgactccc    600
cgccgccccg ggcccacccg caagcattac cagccctatg ccccaccacg cgacttcgca    660
gcctatcgct ccatcgatag agtgaagttc agcaggagcg cagacgcccc cgcgtaccag    720
cagggccaga accagctcta taacgagctc aatctaggac gaagagagga gtacgatgtt    780
ttggacaaga gacgtggccg ggaccctgag atggggggaa agccgagaag gaagaaccct    840
caggaaggcc tgtacaatga actgcagaaa gataagatgg cggaggccta cagtgagatt    900
gggatgaaag gcgagcgccg gaggggcaag gggcacgatg gcctttacca gggtctcagt    960
acagccacca aggacaccta cgacgccctt cacatgcagg ccctgccccc tcgctaa     1017
```

<210> SEQ ID NO 6
<211> LENGTH: 338
<212> TYPE: PRT
<213> ORGANISM: Artificial Sequence
<220> FEATURE:
<223> OTHER INFORMATION: Artificially Synthesized

<400> SEQUENCE: 6

```
Met Ala Leu Pro Val Thr Ala Leu Leu Pro Leu Ala Leu Leu Leu
1               5                   10                  15

His Ala Ala Arg Pro Gly Ser Gly Ser Gly Asp Ser Ala Thr His Ile
                20                  25                  30

Lys Phe Ser Lys Arg Asp Glu Asp Gly Lys Glu Leu Ala Gly Ala Thr
            35                  40                  45

Met Glu Leu Arg Asp Ser Ser Gly Lys Thr Ile Ser Thr Trp Ile Ser
        50                  55                  60

Asp Gly Gln Val Lys Asp Phe Tyr Leu Tyr Pro Gly Lys Tyr Thr Phe
65                  70                  75                  80

Val Glu Thr Ala Ala Pro Asp Gly Tyr Glu Val Ala Thr Ala Ile Thr
                85                  90                  95

Phe Thr Val Asn Glu Gln Gly Gln Val Thr Val Asn Gly Ala Ser Thr
            100                 105                 110

Thr Thr Pro Ala Pro Arg Pro Pro Thr Pro Ala Pro Thr Ile Ala Ser
        115                 120                 125

Gln Pro Leu Ser Leu Arg Pro Glu Ala Cys Arg Pro Ala Ala Gly Gly
    130                 135                 140

Ala Val His Thr Arg Gly Leu Asp Phe Ala Cys Asp Phe Trp Val Leu
145                 150                 155                 160

Val Val Val Gly Gly Val Leu Ala Cys Tyr Ser Leu Leu Val Thr Val
                165                 170                 175

Ala Phe Ile Ile Phe Trp Val Arg Ser Lys Arg Ser Arg Leu Leu His
            180                 185                 190

Ser Asp Tyr Met Asn Met Thr Pro Arg Arg Pro Gly Pro Thr Arg Lys
        195                 200                 205

His Tyr Gln Pro Tyr Ala Pro Pro Arg Asp Phe Ala Ala Tyr Arg Ser
    210                 215                 220

Ile Asp Arg Val Lys Phe Ser Arg Ser Ala Asp Ala Pro Ala Tyr Gln
225                 230                 235                 240

Gln Gly Gln Asn Gln Leu Tyr Asn Glu Leu Asn Leu Gly Arg Arg Glu
                245                 250                 255
```

```
Glu Tyr Asp Val Leu Asp Lys Arg Arg Gly Arg Asp Pro Glu Met Gly
            260                 265                 270

Gly Lys Pro Arg Lys Asn Pro Gln Glu Gly Leu Tyr Asn Glu Leu
        275                 280                 285

Gln Lys Asp Lys Met Ala Glu Ala Tyr Ser Glu Ile Gly Met Lys Gly
        290                 295                 300

Glu Arg Arg Arg Gly Lys Gly His Asp Gly Leu Tyr Gln Gly Leu Ser
305                 310                 315                 320

Thr Ala Thr Lys Asp Thr Tyr Asp Ala Leu His Met Gln Ala Leu Pro
                325                 330                 335

Pro Arg

<210> SEQ ID NO 7
<211> LENGTH: 1080
<212> TYPE: DNA
<213> ORGANISM: Artificial Sequence
<220> FEATURE:
<223> OTHER INFORMATION: Artificially Synthesized

<400> SEQUENCE: 7
atggccttac cagtgaccgc cttgctcctg ccgctggcct tgctgctcca cgccgccagg      60
ccgggatccg gaagcggcga tagcgccacc cacatcaagt tcagcaagcg ggacgaggac     120
ggcaaagagc tggctggcgc caccatggaa ctgcgggaca gcagcggcaa gaccatcagc     180
acctggatca gcgacggcca ggtcaaagac ttctacctgt accccggcaa gtacaccttc     240
gtggaaacag ccgcccctga cggctacgag gtggccacag ccatcacctt caccgtgaac     300
gagcagggac aggtcacagt gaacggcggc ggcagcggcg gcagcggcgg cagcggcggc     360
agcggcggca gcggcggcag cggcggcagc gctagcacca cgacgccagc gccgcgacca     420
ccaacaccgg cgcccaccat cgcgtcgcag cccctgtccc tgcgcccaga ggcgtgccgg     480
ccagcggcgg gggcgcagt gcacacgagg gggctggact cgcctgtga ttttgggtg       540 ctggtggtgg ttggtggagt cctggcttgc tatagcttgc tagtaacagt ggcctttatt     600
attttctggg tgaggagtaa gaggagcagg ctcctgcaca gtgactacat gaacatgact     660
ccccgccgcc ccgggcccac ccgcaagcat taccagccct atgcccccac acgcgacttc     720
gcagcctatc gctccatcga tagagtgaag ttcagcagga gcgcagacgc ccccgcgtac     780
cagcagggcc agaaccagct ctataacgag ctcaatctag gacgaagaga ggagtacgat     840
gttttggaca gagacgtggc ccggaccct gagatggggg gaaagccgag aaggaagaac      900
cctcaggaag gcctgtacaa tgaactgcag aaagataaga tggcggaggc ctacagtgag     960
attgggatga aggcgagcg ccggagggc aaggggcacg atggccttta ccagggtctc      1020
agtacagcca ccaaggacac ctacgacgcc ttcacatgc aggccctgcc ccctcgctaa      1080

<210> SEQ ID NO 8
<211> LENGTH: 359
<212> TYPE: PRT
<213> ORGANISM: Artificial Sequence
<220> FEATURE:
<223> OTHER INFORMATION: Artificially Synthesized

<400> SEQUENCE: 8

Met Ala Leu Pro Val Thr Ala Leu Leu Leu Pro Leu Ala Leu Leu Leu
1               5                   10                  15

His Ala Ala Arg Pro Gly Ser Gly Ser Gly Asp Ser Ala Thr His Ile
            20                  25                  30
```

Lys Phe Ser Lys Arg Asp Glu Asp Gly Lys Glu Leu Ala Gly Ala Thr
            35                  40                  45

Met Glu Leu Arg Asp Ser Ser Gly Lys Thr Ile Ser Thr Trp Ile Ser
 50                  55                  60

Asp Gly Gln Val Lys Asp Phe Tyr Leu Tyr Pro Gly Lys Tyr Thr Phe
 65                  70                  75                  80

Val Glu Thr Ala Ala Pro Asp Gly Tyr Glu Val Ala Thr Ala Ile Thr
                 85                  90                  95

Phe Thr Val Asn Glu Gln Gly Gln Val Thr Val Asn Gly Gly Gly Ser
                100                 105                 110

Gly Gly Ser Gly Gly Ser Gly Gly Ser Gly Gly Ser Gly Gly Ser Gly
            115                 120                 125

Gly Ser Ala Ser Thr Thr Thr Pro Ala Pro Arg Pro Pro Thr Pro Ala
130                 135                 140

Pro Thr Ile Ala Ser Gln Pro Leu Ser Leu Arg Pro Glu Ala Cys Arg
145                 150                 155                 160

Pro Ala Ala Gly Gly Ala Val His Thr Arg Gly Leu Asp Phe Ala Cys
                165                 170                 175

Asp Phe Trp Val Leu Val Val Gly Gly Val Leu Ala Cys Tyr Ser
            180                 185                 190

Leu Leu Val Thr Val Ala Phe Ile Ile Phe Trp Val Arg Ser Lys Arg
            195                 200                 205

Ser Arg Leu Leu His Ser Asp Tyr Met Asn Met Thr Pro Arg Arg Pro
210                 215                 220

Gly Pro Thr Arg Lys His Tyr Gln Pro Tyr Ala Pro Pro Arg Asp Phe
225                 230                 235                 240

Ala Ala Tyr Arg Ser Ile Asp Arg Val Lys Phe Ser Arg Ser Ala Asp
                245                 250                 255

Ala Pro Ala Tyr Gln Gln Gly Gln Asn Gln Leu Tyr Asn Glu Leu Asn
                260                 265                 270

Leu Gly Arg Arg Glu Glu Tyr Asp Val Leu Asp Lys Arg Gly Arg
275                 280                 285

Asp Pro Glu Met Gly Gly Lys Pro Arg Arg Lys Asn Pro Gln Glu Gly
290                 295                 300

Leu Tyr Asn Glu Leu Gln Lys Asp Lys Met Ala Glu Ala Tyr Ser Glu
305                 310                 315                 320

Ile Gly Met Lys Gly Glu Arg Arg Arg Gly Lys Gly His Asp Gly Leu
                325                 330                 335

Tyr Gln Gly Leu Ser Thr Ala Thr Lys Asp Thr Tyr Asp Ala Leu His
            340                 345                 350

Met Gln Ala Leu Pro Pro Arg
        355

<210> SEQ ID NO 9
<211> LENGTH: 798
<212> TYPE: DNA
<213> ORGANISM: Artificial Sequence
<220> FEATURE:
<223> OTHER INFORMATION: Artificially Synthesized

<400> SEQUENCE: 9
atggcctrac cagtgaccgc cttgctcctg ccgctggcct tgctgctcca cgccgccagg    60
ccgggatccg cccacattgt gatggtggac gcctacaagc ccaccaaggc tagcaccacg   120
acgccagcgc cgcgaccacc aacaccggcg cccaccatcg cgtcgcagcc cctgtccctg   180

```
cgcccagagg cgtgccggcc agcggcgggg ggcgcagtgc acacgagggg gctggacttc    240
gcctgtgatt tttgggtgct ggtggtggtt ggtggagtcc tggcttgcta tagcttgcta    300
gtaacagtgg cctttattat tttctgggtg aggagtaaga ggagcaggct cctgcacagt    360
gactacatga acatgactcc ccgccgcccc gggcccaccc gcaagcatta ccagccctat    420
gccccaccac gcgacttcgc agcctatcgc tccatcgata gagtgaagtt cagcaggagc    480
gcagacgccc ccgcgtacca gcagggccag aaccagctct ataacgagct caatctagga    540
cgaagagagg agtacgatgt tttggacaag agacgtggcc gggaccctga gatgggggga    600
aagccgagaa ggaagaaccc tcaggaaggc ctgtacaatg aactgcagaa agataagatg    660
gcggaggcct acagtgagat tgggatgaaa ggcgagcgcc ggaggggcaa ggggcacgat    720
ggcctttacc agggtctcag tacagccacc aaggacacct acgacgccct tcacatgcag    780
gccctgcccc ctcgctaa                                                  798
```

<210> SEQ ID NO 10
<211> LENGTH: 265
<212> TYPE: PRT
<213> ORGANISM: Artificial Sequence
<220> FEATURE:
<223> OTHER INFORMATION: Artificially Synthesized

<400> SEQUENCE: 10

```
Met Ala Leu Pro Val Thr Ala Leu Leu Pro Leu Ala Leu Leu Leu
1               5                   10                  15

His Ala Ala Arg Pro Gly Ser Ala His Ile Val Met Val Asp Ala Tyr
            20                  25                  30

Lys Pro Thr Lys Ala Ser Thr Thr Thr Pro Ala Pro Arg Pro Pro Thr
        35                  40                  45

Pro Ala Pro Thr Ile Ala Ser Gln Pro Leu Ser Leu Arg Pro Glu Ala
    50                  55                  60

Cys Arg Pro Ala Ala Gly Gly Ala Val His Thr Arg Gly Leu Asp Phe
65                  70                  75                  80

Ala Cys Asp Phe Trp Val Leu Val Val Gly Gly Val Leu Ala Cys
                85                  90                  95

Tyr Ser Leu Leu Val Thr Val Ala Phe Ile Ile Phe Trp Val Arg Ser
                100                 105                 110

Lys Arg Ser Arg Leu Leu His Ser Asp Tyr Met Asn Met Thr Pro Arg
            115                 120                 125

Arg Pro Gly Pro Thr Arg Lys His Tyr Gln Pro Tyr Ala Pro Pro Arg
        130                 135                 140

Asp Phe Ala Ala Tyr Arg Ser Ile Asp Arg Val Lys Phe Ser Arg Ser
145                 150                 155                 160

Ala Asp Ala Pro Ala Tyr Gln Gln Gly Gln Asn Gln Leu Tyr Asn Glu
                165                 170                 175

Leu Asn Leu Gly Arg Arg Glu Glu Tyr Asp Val Leu Asp Lys Arg Arg
            180                 185                 190

Gly Arg Asp Pro Glu Met Gly Gly Lys Pro Arg Arg Lys Asn Pro Gln
        195                 200                 205

Glu Gly Leu Tyr Asn Glu Leu Gln Lys Asp Lys Met Ala Glu Ala Tyr
    210                 215                 220

Ser Glu Ile Gly Met Lys Gly Glu Arg Arg Arg Gly Lys Gly His Asp
225                 230                 235                 240

Gly Leu Tyr Gln Gly Leu Ser Thr Ala Thr Lys Asp Thr Tyr Asp Ala
                245                 250                 255
```

```
Leu His Met Gln Ala Leu Pro Pro Arg
            260                 265

<210> SEQ ID NO 11
<211> LENGTH: 861
<212> TYPE: DNA
<213> ORGANISM: Artificial Sequence
<220> FEATURE:
<223> OTHER INFORMATION: Artificially Synthesized

<400> SEQUENCE: 11
atggccttac cagtgaccgc cttgctcctg ccgctggcct tgctgctcca cgccgccagg      60
ccgggatccg cccacatcgt gatggtggac gcctacaagc ccaccaaggg cggcagcggc     120
ggcagcggcg gcagcggcgg cagcggcggc agcggcggca gcggcggcag cgctagcacc     180
acgacgccag cgccgcgacc accaacaccg gcgcccacca tcgcgtcgca gcccctgtcc     240
ctgcgcccag aggcgtgccg gccagcggcg ggggcgcag tgcacacgag ggggctggac      300
ttcgcctgtg attttgggt gctggtgtg gttggtggag tcctggcttg ctatagcttg       360
ctagtaacag tggcctttat tattttctgg gtgaggagta agaggagcag gctcctgcac     420
agtgactaca tgaacatgac tccccgccgc cccgggccca cccgcaagca ttaccagccc     480
tatgccccac cacgcgactt cgcagcctat cgctccatcg atagagtgaa gttcagcagg     540
agcgcagacg ccccgcgta ccagcagggc cagaaccagc tctataacga gctcaatcta     600
ggacgaagag aggagtacga tgttttggac aagagacgtg gccgggaccc tgagatgggg     660
ggaaagccga gaaggaagaa ccctcaggaa ggcctgtaca tgaactgca gaaagataag     720 atggcggagg cctacagtga gattgggatg aaaggcgagc gccggagggg caaggggcac     780
gatggccttt accagggtct cagtacagcc accaaggaca cctacgacgc ccttcacatg     840
caggccctgc ccctcgcta a                                                 861

<210> SEQ ID NO 12
<211> LENGTH: 286
<212> TYPE: PRT
<213> ORGANISM: Artificial Sequence
<220> FEATURE:
<223> OTHER INFORMATION: Artificially Synthesized

<400> SEQUENCE: 12

Met Ala Leu Pro Val Thr Ala Leu Leu Leu Pro Leu Ala Leu Leu Leu
1               5                   10                  15

His Ala Ala Arg Pro Gly Ser Ala His Ile Val Met Val Asp Ala Tyr
            20                  25                  30

Lys Pro Thr Lys Gly Gly Ser Gly Gly Ser Gly Gly Ser Gly Gly Ser
        35                  40                  45

Gly Gly Ser Gly Gly Ser Gly Gly Ser Ala Ser Thr Thr Thr Pro Ala
    50                  55                  60

Pro Arg Pro Pro Thr Pro Ala Pro Thr Ile Ala Ser Gln Pro Leu Ser
65                  70                  75                  80

Leu Arg Pro Glu Ala Cys Arg Pro Ala Ala Gly Gly Ala Val His Thr
                85                  90                  95

Arg Gly Leu Asp Phe Ala Cys Asp Phe Trp Val Leu Val Val Val Gly
            100                 105                 110

Gly Val Leu Ala Cys Tyr Ser Leu Leu Val Thr Val Ala Phe Ile Ile
        115                 120                 125

Phe Trp Val Arg Ser Lys Arg Ser Arg Leu Leu His Ser Asp Tyr Met
```

```
                  130               135               140
Asn Met Thr Pro Arg Arg Pro Gly Pro Thr Arg Lys His Tyr Gln Pro
145                 150               155                 160

Tyr Ala Pro Pro Arg Asp Phe Ala Ala Tyr Arg Ser Ile Asp Arg Val
                165                 170                 175

Lys Phe Ser Arg Ser Ala Asp Ala Pro Ala Tyr Gln Gln Gly Gln Asn
            180                 185                 190

Gln Leu Tyr Asn Glu Leu Asn Leu Gly Arg Arg Glu Glu Tyr Asp Val
            195                 200                 205

Leu Asp Lys Arg Arg Gly Arg Asp Pro Glu Met Gly Gly Lys Pro Arg
210                 215                 220

Arg Lys Asn Pro Gln Glu Gly Leu Tyr Asn Glu Leu Gln Lys Asp Lys
225                 230                 235                 240

Met Ala Glu Ala Tyr Ser Glu Ile Gly Met Lys Gly Glu Arg Arg Arg
                245                 250                 255

Gly Lys Gly His Asp Gly Leu Tyr Gln Gly Leu Ser Thr Ala Thr Lys
            260                 265                 270

Asp Thr Tyr Asp Ala Leu His Met Gln Ala Leu Pro Pro Arg
            275                 280                 285

<210> SEQ ID NO 13
<211> LENGTH: 1806
<212> TYPE: DNA
<213> ORGANISM: Artificial Sequence
<220> FEATURE:
<223> OTHER INFORMATION: Artificially Synthesized

<400> SEQUENCE: 13
```

| | | |
|---|---|---|
| atggtgagca agggcgagga gctgttcacc ggggtggtgc ccatcctggt cgagctggac | 60 |
| ggcgacgtaa acggccacaa gttcagcgtg tccggcgagg gcgagggcga tgccacctac | 120 |
| ggcaagctga ccctgaagtt catctgcacc accggcaagc tgcccgtgcc ctggcccacc | 180 |
| ctcgtgacca ccctgaccta cggcgtgcag tgcttcagcc gctaccccga ccacatgaag | 240 |
| cagcacgact tcttcaagtc cgccatgccc gaaggctacg tccaggagcg caccatcttc | 300 |
| ttcaaggacg acggcaacta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaactacaa cagccacaac gtctatatca tggccgacaa gcagaagaac | 480 |
| ggcatcaagg tgaacttcaa gatccgccac aacatcgagg acggcagcgt gcagctcgcc | 540 |
| gaccactacc agcagaacac ccccatcggc gacggccccg tgctgctgcc cgacaaccac | 600 |
| tacctgagca cccagtccgc cctgagcaaa gaccccaacg agaagcgcga tcacatggtc | 660 |
| ctgctggagt tcgtgaccgc cgccgggatc actctcggca tggacgagct gtacaagaga | 720 |
| tctggcagcg agagggcag aggaagtctt ctaacatgcg gtgacgtgga ggagaatccc | 780 |
| ggccctagaa tggccttacc agtgaccgcc ttgctcctgc cgctggcctt gctgctccac | 840 |
| gccgccaggc cgggatccgg aagcggagat agcgccaccc acatcaagtt cagcaagcgg | 900 |
| gacgaggacg gcaaagagct ggctggcgcc accatggaac tgcgggatag cagcggcaag | 960 |
| accatcagca cctggatcag cgacggccag gtcaaagact tctacctgta ccccggcaag | 1020 |
| tacaccttcg tggaaacagc cgcccctgac ggctatgagg tggccacagc catcaccttc | 1080 |
| accgtgaacg agcagggaca ggtcacagtg aacggcgcta gcaccacgac gccagcgccg | 1140 |
| cgaccaccaa caccggcgcc caccatcgcg tcgcagcccc tgtccctgcg cccagaggcg | 1200 |

-continued

```
tgccggccag cggcgggggg cgcagtgcac acgaggggc tggacttcgc ctgtgatttt    1260
tgggtgctgg tggtggttgg tggagtcctg gcttgctata gcttgctagt aacagtggcc    1320
tttattattt tctgggtgag gagtaagagg agcaggctcc tgcacagtga ctacatgaac    1380
atgactcccc gccgcccgg gcccaccccgc aagcattacc agcctatgc cccaccacgc    1440 gacttcgcag cctatcgctc catcgataga gtgaagttca gcaggagcgc agacgccccc    1500
gcgtaccagc agggccagaa ccagctctat aacgagctca atctaggacg aagagaggag    1560
tacgatgttt tggacaagag acgtggccgg gaccctgaga tgggggggaaa gccgagaagg    1620 aagaaccctc aggaaggcct gtacaatgaa ctgcagaaag ataagatggc ggaggcctac    1680
agtgagattg ggatgaaagg cgagcgccgg aggggcaagg ggcacgatgg cctttaccag    1740
ggtctcagta cagccaccaa ggacacctac gacgcccttc acatgcaggc cctgccccct    1800
cgctaa                                                                1806
```

<210> SEQ ID NO 14
<211> LENGTH: 601
<212> TYPE: PRT
<213> ORGANISM: Artificial Sequence
<220> FEATURE:
<223> OTHER INFORMATION: Artificially Synthesized

<400> SEQUENCE: 14

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Arg
225                 230                 235                 240

Ser Gly Ser Gly Glu Gly Arg Gly Ser Leu Leu Thr Cys Gly Asp Val
                245                 250                 255
```

Glu Glu Asn Pro Gly Pro Arg Met Ala Leu Pro Val Thr Ala Leu Leu
            260                 265                 270

Leu Pro Leu Ala Leu Leu His Ala Ala Arg Pro Gly Ser Gly Ser
        275                 280                 285

Gly Asp Ser Ala Thr His Ile Lys Phe Ser Lys Arg Asp Glu Asp Gly
        290                 295                 300

Lys Glu Leu Ala Gly Ala Thr Met Glu Leu Arg Asp Ser Ser Gly Lys
305                 310                 315                 320

Thr Ile Ser Thr Trp Ile Ser Asp Gly Gln Val Lys Asp Phe Tyr Leu
                325                 330                 335

Tyr Pro Gly Lys Tyr Thr Phe Val Glu Thr Ala Ala Pro Asp Gly Tyr
            340                 345                 350

Glu Val Ala Thr Ala Ile Thr Phe Thr Val Asn Glu Gln Gly Gln Val
        355                 360                 365

Thr Val Asn Gly Ala Ser Thr Thr Pro Ala Pro Arg Pro Pro Thr
370                 375                 380

Pro Ala Pro Thr Ile Ala Ser Gln Pro Leu Ser Leu Arg Pro Glu Ala
385                 390                 395                 400

Cys Arg Pro Ala Ala Gly Gly Ala Val His Thr Arg Gly Leu Asp Phe
                405                 410                 415

Ala Cys Asp Phe Trp Val Leu Val Val Gly Gly Val Leu Ala Cys
            420                 425                 430

Tyr Ser Leu Leu Val Thr Val Ala Phe Ile Ile Phe Trp Val Arg Ser
        435                 440                 445

Lys Arg Ser Arg Leu Leu His Ser Asp Tyr Met Asn Met Thr Pro Arg
450                 455                 460

Arg Pro Gly Pro Thr Arg Lys His Tyr Gln Pro Tyr Ala Pro Pro Arg
465                 470                 475                 480

Asp Phe Ala Ala Tyr Arg Ser Ile Asp Arg Val Lys Phe Ser Arg Ser
                485                 490                 495

Ala Asp Ala Pro Ala Tyr Gln Gln Gly Gln Asn Gln Leu Tyr Asn Glu
            500                 505                 510

Leu Asn Leu Gly Arg Arg Glu Glu Tyr Asp Val Leu Asp Lys Arg Arg
        515                 520                 525

Gly Arg Asp Pro Glu Met Gly Gly Lys Pro Arg Arg Lys Asn Pro Gln
530                 535                 540

Glu Gly Leu Tyr Asn Glu Leu Gln Lys Asp Lys Met Ala Glu Ala Tyr
545                 550                 555                 560

Ser Glu Ile Gly Met Lys Gly Glu Arg Arg Gly Lys Gly His Asp
                565                 570                 575

Gly Leu Tyr Gln Gly Leu Ser Thr Ala Thr Lys Asp Thr Tyr Asp Ala
        580                 585                 590

Leu His Met Gln Ala Leu Pro Pro Arg
595                 600

<210> SEQ ID NO 15
<211> LENGTH: 1869
<212> TYPE: DNA
<213> ORGANISM: Artificial Sequence
<220> FEATURE:
<223> OTHER INFORMATION: Artificially Synthesized

<400> SEQUENCE: 15
atggtgagca agggcgagga gctgttcacc ggggtggtgc ccatcctggt cgagctggac      60

```
ggcgacgtaa acggccacaa gttcagcgtg tccggcgagg gcgagggcga tgccacctac    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
cagcacgact tcttcaagtc cgccatgccc gaaggctacg tccaggagcg caccatcttc    300
ttcaaggacg acggcaacta caagacccgc gccgaggtga agttcgaggg cgacaccctg    360
gtgaaccgca tcgagctgaa gggcatcgac ttcaaggagg acggcaacat cctggggcac    420
aagctggagt acaactacaa cagccacaac gtctatatca tggccgacaa gcagaagaac    480
ggcatcaagg tgaacttcaa gatccgccac aacatcgagg acggcagcgt gcagctcgcc    540
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagaga    720
tctggcagcg gagagggcag aggaagtctt ctaacatgcg gtgacgtgga ggagaatccc    780
ggccctagaa tggccttacc agtgaccgcc ttgctcctgc cgctggcctt gctgctccac    840
gccgccaggc cgggatccgg aagcggcgat agcgccaccc acatcaagtt cagcaagcgg    900
gacgaggacg gcaaagagct ggctggcgcc accatgaact gcgggacag cagcggcaag    960
accatcagca cctggatcag cgacggccag gtcaaagact tctacctgta ccccggcaag   1020
tacaccttcg tggaaacagc cgcccctgac ggctacgagg tggccacagc catcaccttc   1080
accgtgaacg agcagggaca ggtcacagtg aacggcggcg gcagcggcgg cagcggcggc   1140
agcggcggca gcggcggcag cggcggcagc ggcggcagcg ctagcaccac gacgccagcg   1200
ccgcgaccac caacaccggc gcccaccatc gcgtcgcagc ccctgtccct gcgcccagag   1260
gcgtgccggc cagcggcggg gggcgcagtg cacacgaggg gctggacttc gcctgtgat   1320
ttttgggtgc tggtggtggt tggtggagtc ctggcttgct atagcttgct agtaacagtg   1380
gcctttatta ttttctgggt gaggagtaag aggagcaggc cctgcacag tgactacatg    1440
aacatgactc cccgccgccc cgggcccacc cgcaagcatt accagcccta tgccccacca   1500
cgcgacttcg cagcctatcg ctccatcgat agagtgaagt tcagcaggag cgcagacgcc   1560
cccgcgtacc agcagggcca gaaccagctc tataacgagc tcaatctagg acgaagagag   1620
gagtacgatg ttttggacaa gagacgtggc cgggaccctg agatgggggg aaagccgaga   1680
aggaagaacc ctcaggaagg cctgtacaat gaactgcaga agataagat ggcggaggcc    1740
tacagtgaga ttgggatgaa aggcgagcgc cggaggggca aggggcacga tggcctttac   1800
cagggtctca gtacagccac caaggacacc tacgacgccc ttcacatgca ggccctgccc   1860
cctcgctaa                                                           1869
```

<210> SEQ ID NO 16
<211> LENGTH: 622
<212> TYPE: PRT
<213> ORGANISM: Artificial Sequence
<220> FEATURE:
<223> OTHER INFORMATION: Artificially Synthesized

<400> SEQUENCE: 16

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile

```
                35                  40                  45
Cys Thr Thr Gly Lys Leu Pro Val Pro Trp Pro Thr Leu Val Thr Thr
 50                  55                  60

Leu Thr Tyr Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                 85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
                115                 120                 125

Ile Asp Phe Lys Glu Asp Gly Asn Ile Leu Gly His Lys Leu Glu Tyr
                130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
                195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Arg
225                 230                 235                 240

Ser Gly Ser Gly Glu Gly Arg Gly Ser Leu Leu Thr Cys Gly Asp Val
                245                 250                 255

Glu Glu Asn Pro Gly Pro Arg Met Ala Leu Pro Val Thr Ala Leu Leu
                260                 265                 270

Leu Pro Leu Ala Leu Leu Leu His Ala Ala Arg Pro Gly Ser Gly Ser
                275                 280                 285

Gly Asp Ser Ala Thr His Ile Lys Phe Ser Lys Arg Asp Glu Asp Gly
                290                 295                 300

Lys Glu Leu Ala Gly Ala Thr Met Glu Leu Arg Asp Ser Ser Gly Lys
305                 310                 315                 320

Thr Ile Ser Thr Trp Ile Ser Asp Gly Gln Val Lys Asp Phe Tyr Leu
                325                 330                 335

Tyr Pro Gly Lys Tyr Thr Phe Val Glu Thr Ala Ala Pro Asp Gly Tyr
                340                 345                 350

Glu Val Ala Thr Ala Ile Thr Phe Thr Val Asn Glu Gln Gly Gln Val
                355                 360                 365

Thr Val Asn Gly Gly Gly Ser Gly Gly Ser Gly Gly Ser Gly Gly Ser
                370                 375                 380

Gly Gly Ser Gly Gly Ser Gly Gly Ser Ala Ser Thr Thr Thr Pro Ala
385                 390                 395                 400

Pro Arg Pro Pro Thr Pro Ala Pro Thr Ile Ala Ser Gln Pro Leu Ser
                405                 410                 415

Leu Arg Pro Glu Ala Cys Arg Pro Ala Ala Gly Gly Ala Val His Thr
                420                 425                 430

Arg Gly Leu Asp Phe Ala Cys Asp Phe Trp Val Leu Val Val Val Gly
                435                 440                 445

Gly Val Leu Ala Cys Tyr Ser Leu Leu Val Thr Val Ala Phe Ile Ile
                450                 455                 460
```

```
Phe Trp Val Arg Ser Lys Arg Ser Arg Leu Leu His Ser Asp Tyr Met
465                 470                 475                 480

Asn Met Thr Pro Arg Arg Pro Gly Pro Thr Arg Lys His Tyr Gln Pro
                485                 490                 495

Tyr Ala Pro Pro Arg Asp Phe Ala Ala Tyr Arg Ser Ile Asp Arg Val
            500                 505                 510

Lys Phe Ser Arg Ser Ala Asp Ala Pro Ala Tyr Gln Gln Gly Gln Asn
        515                 520                 525

Gln Leu Tyr Asn Glu Leu Asn Leu Gly Arg Arg Glu Glu Tyr Asp Val
    530                 535                 540

Leu Asp Lys Arg Arg Gly Arg Asp Pro Glu Met Gly Gly Lys Pro Arg
545                 550                 555                 560

Arg Lys Asn Pro Gln Glu Gly Leu Tyr Asn Glu Leu Gln Lys Asp Lys
                565                 570                 575

Met Ala Glu Ala Tyr Ser Glu Ile Gly Met Lys Gly Glu Arg Arg Arg
                580                 585                 590

Gly Lys Gly His Asp Gly Leu Tyr Gln Gly Leu Ser Thr Ala Thr Lys
        595                 600                 605

Asp Thr Tyr Asp Ala Leu His Met Gln Ala Leu Pro Pro Arg
    610                 615                 620
```